US012807973B2

(12) United States Patent
Chatterjee et al.

(10) Patent No.: US 12,807,973 B2
(45) Date of Patent: Nov. 24, 2026

(54) ADENO-ASSOCIATED VIRUS COMPOSITIONS AND METHODS OF USE THEREOF

(71) Applicants: City of Hope, Duarte, CA (US); Homology Medicines, Inc., Bedford, MA (US)

(72) Inventors: Saswati Chatterjee, Altadena, CA (US); Lakshmi Bugga, Arcadia, CA (US); Ka Ming Pang, Arcadia, CA (US); Jeff Lynn Ellsworth, Bedford, MA (US)

(73) Assignee: CITY OF HOPE

( * ) Notice: Subject to any disclaimer, the term of this patent is extended or adjusted under 35 U.S.C. 154(b) by 220 days.

(21) Appl. No.: 18/289,698

(22) PCT Filed: May 11, 2022

(86) PCT No.: PCT/US2022/028844

§ 371 (c)(1),
(2) Date: Nov. 6, 2023

(87) PCT Pub. No.: WO2022/241041

PCT Pub. Date: Nov. 17, 2022

(65) Prior Publication Data

US 2025/0101465 A1 Mar. 27, 2025

Related U.S. Application Data

(60) Provisional application No. 63/187,161, filed on May 11, 2021.

(51) Int. Cl.

| | |
|---|---|
| ***C12N 15/90*** | (2006.01) |
| ***A61K 48/00*** | (2006.01) |
| ***C07K 14/755*** | (2006.01) |
| ***C12N 15/86*** | (2006.01) |

(52) U.S. Cl.
CPC .......... *C12N 15/907* (2013.01); *A61K 48/005* (2013.01); *C07K 14/755* (2013.01); *C12N 15/86* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 2017/0233456 A1 | 8/2017 | Sabatino et al. | |
| 2019/0276856 A1* | 9/2019 | Chatterjee ................ | C12N 7/00 |
| 2019/0351073 A1 | 11/2019 | Laterza et al. | |

OTHER PUBLICATIONS

International Search Report mailed on Oct. 6, 2022, for PCT Application No. PCT/US2022/02884, filed May 11, 2022, 6 pages.
Smith, L.J. et al. (Sep. 2014, e-published Jun. 13, 2014). "Gene transfer properties and structural modeling of human stem cell-derived AAV," *Mol Ther* 22(9):1625-1634.
Smith, L.J. et al. (Jul. 31, 2018, e-published Jul. 17, 2018). "Stem cell-derived clade F AAVs mediate high-efficiency homologous recombination-based genome editing," *PNAS USA* 115(31):E7379-E7388.
Written Opinion mailed on Oct. 6, 2022, for PCT Application No. PCT/US2022/02884, filed May 11, 2022, 6 pages.

* cited by examiner

*Primary Examiner* — Allison M Fox
*Assistant Examiner* — Gina Pronzati
(74) *Attorney, Agent, or Firm* — Mintz, Levin, Cohn, Ferris, Glovsky and Popeo, P.C.

(57) ABSTRACT

Provided herein, inter alia, are compositions and methods related to correcting intron 22 inversion in the F8 gene using AAVHSC-mediated nuclease-free genome-editing.

14 Claims, 39 Drawing Sheets

Specification includes a Sequence Listing.

Analyses of Junction Sequences Show Seamless Insertion of the Correction Sequence at the End of Exon22 in the FVIII Gene in Primary Human LSEC FIG. 22A
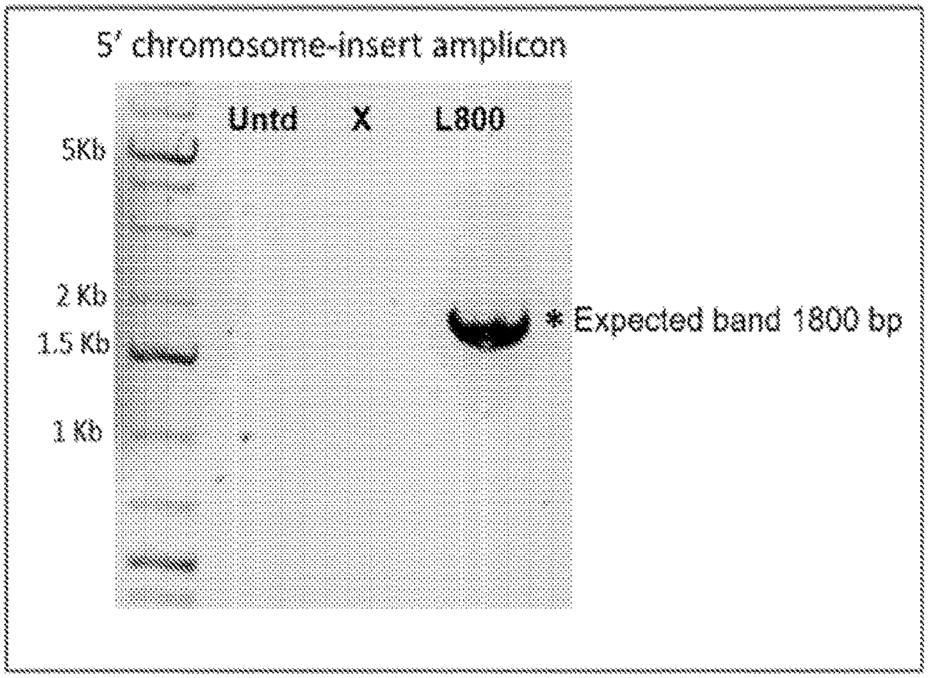
FIG. 22B
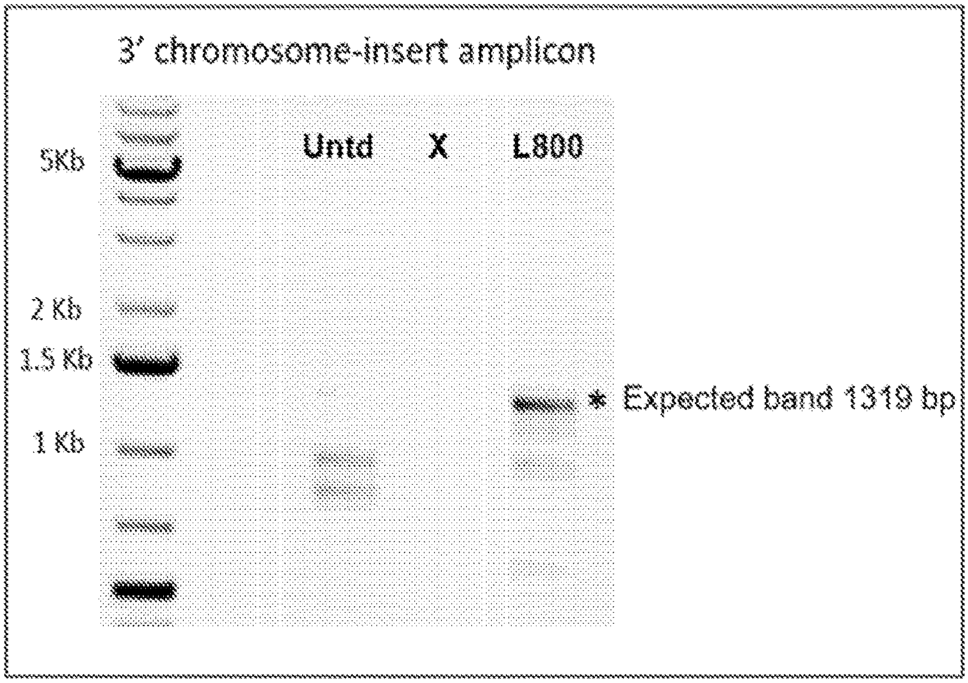
FIGS. 22A-22B

Full Length Factor VIII

| | Mean | SEM |
|---|---|---|
| Nor Untd | 3658.04 | 1422.34 |
| I22I Untd | 3039.92 | 517.43 |
| I22I AAVHSC15 L800R800 | 7644.02 | 2179.76 |

Factor VIII Light Chain

| | Mean | SEM |
|---|---|---|
| Nor Untd | 1000.15 | 511.51 |
| I22I Untd | 924.23 | 778.90 |
| I22I AAVHSC15 L800R800 | 1870.59 | 663.94 |

FLAG Tagged Full Length Factor VIII

| | Mean | SEM |
|---|---|---|
| Nor Untd | 2017.37 | 1415.16 |
| I22I Untd | 2553.05 | 1346.49 |
| I22I AAVHSC15 L800R800 | 10349.40 | 4236.32 |

FLAG Tagged FVIII Light Chain Band

| | Mean | SEM |
|---|---|---|
| Normal Untd | 1093.12 | 493.51 |
| I22I Untd | 2985.79 | 1936.17 |
| I22I AAVHSC15 (L800R800) | 4590.96 | 2483.83 |

ADENO-ASSOCIATED VIRUS COMPOSITIONS AND METHODS OF USE THEREOF

CROSS-REFERENCE TO RELATED APPLICATIONS

This application claims the benefit under 35 U.S.C. § 371 of International Application No. PCT/US2022/028844, filed May 11, 2022, which claims priority to U.S. Provisional Application No. 63/187,161, filed May 11, 2021, which are hereby incorporated by reference in its entirety.

STATEMENT OF GOVERNMENT INTEREST

This invention was made with government support under grant no. P30CA033572 awarded by the National Institutes of Health. The government has certain rights in the invention.

REFERENCE TO SEQUENCE LISTING

This application incorporates by reference a Computer Readable Form (CRF) of a Sequence Listing in ASCII text format submitted with this application, entitled 048440-813N01US SL ST25.txt, created on Nov. 19, 2024, and 31,340 bytes in size.

BACKGROUND

Factor VIII (FVILI), also known as anti-hemophilic factor, is a circulating glycoprotein that is important for normal blood clotting. Factor VIII is produced by liver sinusoidal endothelial cells and endothelial cells outside of the liver. This protein circulates in the bloodstream in an inactive form, bound to another molecule called von Willebrand factor (vWF), until an injury that damages blood vessels occurs. In response to injury, FVIII is activated and separates from vWF. The active protein, FVIIIa, interacts with another coagulation factor called factor IX to initiate a cascade of additional chemical reactions that form a blood clot.

Hemophilia A, also called factor VIII deficiency or classic hemophilia, is an inherited or spontaneous genetic disorder caused by missing or defective factor VIII. It is inherited as an X-linked recessive trait, while nearly one third of cases arise from spontaneous mutations. Clinically, hemophilia A is characterized by internal or external bleeding episodes. Individuals with more severe hemophilia suffer more severe and more frequent bleeding, while others with mild hemophilia typically suffer more minor symptoms except after surgery or serious trauma; individuals with moderate hemophilia have variable symptoms which manifest along a spectrum between severe and mild forms.

F8, the gene for FVIII is located on the long arm of chromosome X, within the Xq28 region. The gene represents 186 kb of the X chromosome. It comprises a 9 kb coding region that contains 26 exons and 25 introns. Mature FVIII is a single-chain polypeptide containing 2332 amino acids. Approximately 40% of cases of severe FVIII deficiency arise from a large inversion involving intron 22 that disrupts the F8 gene. Deletions, insertions, and point mutations account for the remaining 50-60% of the F8 defects that cause hemophilia A.

Provided herein are solutions to these and other problems in the art.

BRIEF SUMMARY

Described herein, inter alia, are compositions and methods for correcting a mutation in the F8 gene by targeted insertion.

In an aspect, provide herein is a method for correcting a mutation in an F8 gene in a cell, the method comprising transducing the cell with a replication-defective adeno-associated virus (AAV) comprising (a) an AAV capsid; and (b) a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus; wherein:

(A) the 5' homology arm consists of the nucleotide sequence set forth in SEQ. ID NO: 1 and the 3' homology arm consists of the nucleotide sequence set forth in SEQ. ID NO: 2; or (B) the 5' homology arm consists of the nucleotide sequence set forth in SEQ. ID NO: 3 and the 3' homology arm consists of the nucleotide sequence set forth in SEQ. ID NO: 4; or (C) the 5' homology arm consists of the nucleotide sequence set forth in SEQ. ID NO: 5 and the 3' homology arm consists of the nucleotide sequence set forth in SEQ. ID NO: 6; or (D) the 5' homology arm consists of the nucleotide sequence set forth in SEQ. ID NO: 7 and the 3' homology arm consists of the nucleotide sequence set forth in SEQ. ID NO: 8; or (E) the 5' homology arm consists of the nucleotide sequence set forth in SEQ. ID NO: 9 and the 3' homology arm consists of the nucleotide sequence set forth in SEQ. ID NO: 10; or (F) the 5' homology arm consists of the nucleotide sequence set forth in SEQ. ID NO: 11 and the 3' homology arm consists of the nucleotide sequence set forth in SEQ. ID NO: 12; or (G) the 5' homology arm consists of the nucleotide sequence set forth in SEQ. ID NO: 13 and the 3' homology arm consists of the nucleotide sequence set forth in SEQ. ID NO: 14; and, wherein the cell is transduced without co-transducing or co-administering an exogenous nuclease or a nucleotide sequence that encodes an exogenous nuclease.

In an aspect, provide herein is a method for correcting a mutation in an F8 gene in a cell, the method comprising transducing the cell with a replication-defective adeno-associated virus (AAV) comprising (a) an AAV capsid; and (b) a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus.

In an aspect, provide herein is a method for treating a subject having a disease or disorder associated with a mutation in an F8 gene, the method comprising administering to the subject an effective amount of a replication-defective recombinant adeno-associated virus (AAV) comprising: (a) an AAV capsid; and (b) a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus; wherein:

(A) the 5' homology arm consists of the nucleotide sequence set forth in SEQ. ID NO: 1 and the 3' homology arm consists of the nucleotide sequence set forth in SEQ. ID NO: 2; or (B) the 5' homology arm consists of the nucleotide sequence set forth in SEQ. ID NO: 3 and the 3' homology arm consists of the nucleotide sequence set forth in SEQ. ID NO: 4; or (C) the 5' homology arm consists of the nucleotide sequence set forth in SEQ. ID NO: 5 and the 3' homology arm consists of the nucleotide sequence set forth in SEQ. ID NO: 6; or (D) the 5' homology arm consists of the nucleotide sequence set forth in SEQ. ID NO: 7 and the 3' homology arm consists of the nucleotide sequence set forth in SEQ. ID NO: 8; or (E) the 5' homology arm consists of the nucleotide sequence set forth in SEQ. ID NO: 9 and the 3' homology arm consists of the nucleotide sequence set forth in SEQ. ID NO: 10; or (F) the 5' homology arm consists of the nucleotide sequence set forth in SEQ. ID NO: 11 and the 3' homology arm consists of the nucleotide sequence set forth in SEQ. ID NO: 12; or (G) the 5' homology arm consists of the nucleotide sequence set forth in SEQ. ID NO: 13 and the 3' homology arm consists of the nucleotide sequence set forth in SEQ. ID NO: 14;

wherein an exogenous nuclease or a nucleotide sequence that encodes an exogenous nuclease is not co-administered to the subject.

In an aspect, provide herein is a method for correcting a mutation in an F8 gene in a cell, the method comprising transducing the cell with a replication-defective adeno-associated virus (AAV) comprising: (a) an AAV capsid; and (b) a correction genome comprising: (i) an editing element for editing a target locus in the F8 gene; (ii) a 5' homology arm nucleotide sequence 5' to the editing element having homology to a first genomic region 5' to the target locus; (iii) a 3' homology arm nucleotide sequence 3' to the editing element having homology to a second genomic region 3' to the target locus; and (iv) an F8 coding sequence; wherein the F8 coding sequence consists of the nucleotide sequences set forth in SEQ. ID NOS: 15, 16, or 17; and, wherein the cell is transduced without co-transducing or co-administering an exogenous nuclease or a nucleotide sequence that encodes an exogenous nuclease.

In an aspect, provided herein is a method for treating a subject having a disease or disorder associated with a mutation in an F8 gene, the method comprising administering to the subject an effective amount of a replication-defective recombinant adeno-associated virus (AAV) comprising: (a) an AAV capsid; and (b) a correction genome comprising: (i) an editing element for editing a target locus in the F8 gene; (ii) a 5' homology arm nucleotide sequence 5' to the editing element having homology to a first genomic region 5' to the target locus; (iii) a 3' homology arm nucleotide sequence 3' to the editing element having homology to a second genomic region 3' to the target locus, and (iv) an F8 coding sequence, wherein the F8 coding sequence consists of the nucleotide sequences set forth in SEQ. ID NOS: 15, 16, or 17; and, wherein an exogenous nuclease or a nucleotide sequence that encodes an exogenous nuclease is not co-administered to the subject.

In an aspect, provided herein is replication-defective adeno-associated virus (AAV) comprising: (a) an AAV capsid; and (b) a correction genome comprising: (i) an editing element for editing a target locus in the F8 gene; (ii) a 5' homology arm nucleotide sequence 5' to the editing element having homology to a first genomic region 5' to the target locus; (iii) a 3' homology arm nucleotide sequence 3' to the editing element having homology to a second genomic region 3' to the target locus; and (iv) an F8 coding sequence; wherein the F8 coding sequence consists of the nucleotide sequences set forth in SEQ. ID NOS: 15, 16, or 17.

In an aspect, provided herein is a replication-defective adeno-associated virus (AAV) comprising: (a) an AAV capsid; and (b) a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus;

wherein:

(A) the 5' homology arm consists of the nucleotide sequence set forth in SEQ. ID NO: 1 and the 3' homology arm consists of the nucleotide sequence set forth in SEQ. ID NO: 2; or (B) the 5' homology arm consists of the nucleotide sequence set forth in SEQ. ID NO: 3 and the 3' homology arm consists of the nucleotide sequence set forth in SEQ. ID NO: 4; or (C) the 5' homology arm consists of the nucleotide sequence set forth in SEQ. ID NO: 5 and the 3' homology arm consists of the nucleotide sequence set forth in SEQ. ID NO: 6; or (D) the 5' homology arm consists of the nucleotide sequence set forth in SEQ. ID NO: 7 and the 3' homology arm consists of the nucleotide sequence set forth in SEQ. ID NO: 8; or (E) the 5' homology arm consists of the nucleotide sequence set forth in SEQ. ID NO: 9 and the 3' homology arm consists of the nucleotide sequence set forth in SEQ. ID NO: 10; or (F) the 5' homology arm consists of the nucleotide sequence set forth in SEQ. ID NO: 11 and the 3' homology arm consists of the nucleotide sequence set forth in SEQ. ID NO: 12; or (G) the 5' homology arm consists of the nucleotide sequence set forth in SEQ. ID NO: 13 and the 3' homology arm consists of the nucleotide sequence set forth in SEQ. ID NO: 14.

In an aspect, provided herein is a nucleic acid comprising: (i) an editing element for editing a target locus in an F8 gene; (ii) a 5' homology arm nucleotide sequence 5' to the editing element having homology to a first genomic region 5' to the target locus; (iii) a 3' homology arm nucleotide sequence 3' to the editing element having homology to a second genomic region 3' to the target locus; and, (iv) an F8 coding sequence; wherein the F8 coding sequence consists of the nucleotide sequences set forth in SEQ. ID NOS: 15, 16, or 17.

In an aspect, provided herein is a nucleic acid comprising: (i) an editing element for editing a target locus in an F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus; wherein:

(A) the 5' homology arm consists of the nucleotide sequence set forth in SEQ. ID NO: 1 and the 3' homology arm consists of the nucleotide sequence set forth in SEQ. ID NO: 2; or (B) the 5' homology arm consists of the nucleotide sequence set forth in SEQ. ID NO: 3 and the 3' homology arm consists of the nucleotide sequence set forth in SEQ. ID NO: 4; or (C) the 5' homology arm consists of the nucleotide sequence set forth in SEQ. ID NO: 5 and the 3' homology arm consists of the nucleotide sequence set forth in SEQ. ID NO: 6; or (D) the 5' homology arm consists of the nucleotide sequence set forth in SEQ. ID NO: 7 and the 3' homology arm consists of the nucleotide sequence set forth in SEQ. ID NO: 8; or (E) the 5' homology arm consists of the nucleotide sequence set forth in SEQ. ID NO: 9 and the 3' homology arm consists of the nucleotide sequence set forth in SEQ. ID NO: 10; or (F) the 5' homology arm consists of the nucleotide sequence set forth in SEQ. ID NO: 11 and the 3' homology arm consists of the nucleotide sequence set forth in SEQ. ID NO: 12; or (G) the 5' homology arm consists of the nucleotide sequence set forth in SEQ. ID NO: 13 and the 3' homology arm consists of the nucleotide sequence set forth in SEQ. ID NO: 14.

In another aspect of the methods and compositions provided herein, any of the 5' homology arms disclosed herein may be paired with any of the 3' homology arms provided herein. For example, 5' homology arm 1 (SEQ. ID NO: 1) may be paired with 3' homology arm 2 (SEQ. ID NO: 4).

The following embodiments apply to each of the foregoing aspects.

In embodiments, the 5' homology arm nucleotide sequence consists of at least 200 contiguous nucleotide sequences within SEQ. ID NO: 1. In embodiments, the 5' homology arm nucleotide sequence consists of at least 300 contiguous nucleotide sequences within SEQ. ID NO: 1. In embodiments, the 5' homology arm nucleotide sequence consists of at least 400 contiguous nucleotide sequences within SEQ. ID NO: 1. In embodiments, the 5' homology arm nucleotide sequence consists of at least 500 contiguous nucleotide sequences within SEQ. ID NO: 1. In embodiments, the 5' homology arm nucleotide sequence consists of at least 600 contiguous nucleotide sequences within SEQ. ID NO: 1. In embodiments, the 5' homology arm nucleotide sequence consists of at least 700 contiguous nucleotide sequences within SEQ. ID NO: 1. In embodiments, the 5' homology arm nucleotide sequence consists of at least 800 contiguous nucleotide sequences within SEQ. ID NO: 1. In embodiments, the 5' homology arm nucleotide sequence consists of at least 900 contiguous nucleotide sequences within SEQ. ID NO: 1. In embodiments, the 5' homology arm nucleotide sequence consists of at least 1000 contiguous nucleotide sequences within SEQ. ID NO: 1. In embodiments, the 5' homology arm nucleotide sequence consists of at least 1100 contiguous nucleotide sequences within SEQ. ID NO: 1. In embodiments, the 5' homology arm nucleotide sequence consists of at least 1200 contiguous nucleotide sequences within SEQ. ID NO: 1. In embodiments, the 5' homology arm nucleotide sequence consists of at least 1300 contiguous nucleotide sequences within SEQ. ID NO: 1. In embodiments, the 5' homology arm nucleotide sequence consists of at least 1400 contiguous nucleotide sequences within SEQ. ID NO: 1. In embodiments, the 5' homology arm nucleotide sequence consists of at least 1500 contiguous nucleotide sequences within SEQ. ID NO: 1. In embodiments, the 5' homology arm nucleotide sequence consists of at least 1600 contiguous nucleotide sequences within SEQ. ID NO: 1. In embodiments, the 5' homology arm nucleotide sequence consists of at least 1700 contiguous nucleotide sequences within SEQ. ID NO: 1. In embodiments, the 5' homology arm nucleotide sequence consists of at least 1800 contiguous nucleotide sequences within SEQ. ID NO: 1. In embodiments, the 5' homology arm nucleotide sequence consists of at least 1900 contiguous nucleotide sequences within SEQ. ID NO: 1.

In embodiments, the 3' homology arm nucleotide sequence consists of at least 200 contiguous nucleotide sequences within SEQ. ID NO: 2. In embodiments, the 3' homology arm nucleotide sequence consists of at least 300 contiguous nucleotide sequences within SEQ. ID NO: 2. In embodiments, the 3' homology arm nucleotide sequence consists of at least 400 contiguous nucleotide sequences within SEQ. ID NO: 2. In embodiments, the 3' homology arm nucleotide sequence consists of at least 500 contiguous nucleotide sequences within SEQ. ID NO: 2. In embodiments, the 3' homology arm nucleotide sequence consists of at least 600 contiguous nucleotide sequences within SEQ. ID NO: 2. In embodiments, the 3' homology arm nucleotide sequence consists of at least 700 contiguous nucleotide sequences within SEQ. ID NO: 2. In embodiments, the 3' homology arm nucleotide sequence consists of at least 800 contiguous nucleotide sequences within SEQ. ID NO: 2. In embodiments, the 3' homology arm nucleotide sequence consists of at least 900 contiguous nucleotide sequences within SEQ. ID NO: 2. In embodiments, the 3' homology arm nucleotide sequence consists of at least 1000 contiguous nucleotide sequences within SEQ. ID NO: 2. In embodiments, the 3' homology arm nucleotide sequence consists of at least 1100 contiguous nucleotide sequences within SEQ. ID NO: 2. In embodiments, the 3' homology arm nucleotide sequence consists of at least 1200 contiguous nucleotide sequences within SEQ. ID NO: 2. In embodiments, the 3' homology arm nucleotide sequence consists of at least 1300 contiguous nucleotide sequences within SEQ. ID NO: 2. In embodiments, the 3' homology arm nucleotide sequence consists of at least 1400 contiguous nucleotide sequences within SEQ. ID NO: 2. In embodiments, the 3' homology arm nucleotide sequence consists of at least 1500 contiguous nucleotide sequences within SEQ. ID NO: 2. In embodiments, the 3' homology arm nucleotide sequence consists of at least 1600 contiguous nucleotide sequences within SEQ. ID NO: 2. In embodiments, the 3' homology arm nucleotide sequence consists of at least 1700 contiguous nucleotide sequences within SEQ. ID NO: 2. In embodiments, the 3' homology arm nucleotide sequence consists of at least 1800 contiguous nucleotide sequences within SEQ. ID NO: 2. In embodiments, the 3' homology arm nucleotide sequence consists of at least 1900 contiguous nucleotide sequences within SEQ. ID NO: 2.

In embodiments, the 5' homology arm nucleotide sequence consists of at least 200 contiguous nucleotide sequences within SEQ. ID NO: 3. In embodiments, the 5' homology arm nucleotide sequence consists of at least 300 contiguous nucleotide sequences within SEQ. ID NO: 3. In embodiments, the 5' homology arm nucleotide sequence consists of at least 400 contiguous nucleotide sequences within SEQ. ID NO: 3. In embodiments, the 5' homology arm nucleotide sequence consists of at least 500 contiguous nucleotide sequences within SEQ. ID NO: 3. In embodiments, the 5' homology arm nucleotide sequence consists of at least 600 contiguous nucleotide sequences within SEQ. ID NO: 3. In embodiments, the 5' homology arm nucleotide sequence consists of at least 700 contiguous nucleotide sequences within SEQ. ID NO: 3. In embodiments, the 5' homology arm nucleotide sequence consists of at least 800 contiguous nucleotide sequences within SEQ. ID NO: 3. In embodiments, the 5' homology arm nucleotide sequence consists of at least 900 contiguous nucleotide sequences within SEQ. ID NO: 3. In embodiments, the 5' homology arm nucleotide sequence consists of at least 1000 contiguous nucleotide sequences within SEQ. ID NO: 3. In embodiments, the 5' homology arm nucleotide sequence consists of at least 1100 contiguous nucleotide sequences within SEQ. ID NO: 3. In embodiments, the 5' homology arm nucleotide sequence consists of at least 1200 contiguous nucleotide sequences within SEQ. ID NO: 3. In embodiments, the 5' homology arm nucleotide sequence consists of at least 1300 contiguous nucleotide sequences within SEQ. ID NO: 3. In embodiments, the 5' homology arm nucleotide sequence consists of at least 1400 contiguous nucleotide sequences within SEQ. ID NO: 3. In embodiments, the 5' homology arm nucleotide sequence consists of at least 1500 contiguous nucleotide sequences within SEQ. ID NO: 3. In embodiments, the 5' homology arm nucleotide sequence consists of at least 1600 contiguous nucleotide sequences within SEQ. ID NO: 3. In embodiments, the 5' homology arm nucleotide sequence consists of at least 1700 contiguous nucleotide sequences within SEQ. ID NO: 3. In embodiments, the 5' homology arm nucleotide sequence consists of at least 1800 contiguous nucleotide sequences within SEQ. ID NO: 3. In embodiments, the 5' homology arm nucleotide sequence consists of at least 1900 contiguous nucleotide sequences within SEQ. ID NO: 3.

In embodiments, the 3' homology arm nucleotide sequence consists of at least 200 contiguous nucleotide sequences within SEQ. ID NO: 4. In embodiments, the 3' homology arm nucleotide sequence consists of at least 300 contiguous nucleotide sequences within SEQ. ID NO: 4. In embodiments, the 3' homology arm nucleotide sequence consists of at least 400 contiguous nucleotide sequences within SEQ. ID NO: 4. In embodiments, the 3' homology arm nucleotide sequence consists of at least 500 contiguous nucleotide sequences within SEQ. ID NO: 4. In embodiments, the 3' homology arm nucleotide sequence consists of at least 600 contiguous nucleotide sequences within SEQ. ID NO: 4. In embodiments, the 3' homology arm nucleotide sequence consists of at least 700 contiguous nucleotide sequences within SEQ. ID NO: 4. In embodiments, the 3' homology arm nucleotide sequence consists of at least 800 contiguous nucleotide sequences within SEQ. ID NO: 4. In embodiments, the 3' homology arm nucleotide sequence consists of at least 900 contiguous nucleotide sequences within SEQ. ID NO: 4. In embodiments, the 3' homology arm nucleotide sequence consists of at least 1000 contiguous nucleotide sequences within SEQ. ID NO: 4. In embodiments, the 3' homology arm nucleotide sequence consists of at least 1100 contiguous nucleotide sequences within SEQ. ID NO: 4. In embodiments, the 3' homology arm nucleotide sequence consists of at least 1200 contiguous nucleotide sequences within SEQ. ID NO: 4. In embodiments, the 3' homology arm nucleotide sequence consists of at least 1300 contiguous nucleotide sequences within SEQ. ID NO: 4. In embodiments, the 3' homology arm nucleotide sequence consists of at least 1400 contiguous nucleotide sequences within SEQ. ID NO: 4. In embodiments, the 3' homology arm nucleotide sequence consists of at least 1500 contiguous nucleotide sequences within SEQ. ID NO: 4. In embodiments, the 3' homology arm nucleotide sequence consists of at least 1600 contiguous nucleotide sequences within SEQ. ID NO: 4. In embodiments, the 3' homology arm nucleotide sequence consists of at least 1700 contiguous nucleotide sequences within SEQ. ID NO: 4. In embodiments, the 3' homology arm nucleotide sequence consists of at least 1800 contiguous nucleotide sequences within SEQ. ID NO: 4. In embodiments, the 3' homology arm nucleotide sequence consists of at least 1900 contiguous nucleotide sequences within SEQ. ID NO: 4.

In embodiments, the 5' homology arm nucleotide sequence consists of at least 200 contiguous nucleotide sequences within SEQ. ID NO: 5. In embodiments, the 5' homology arm nucleotide sequence consists of at least 300 contiguous nucleotide sequences within SEQ. ID NO: 5. In embodiments, the 5' homology arm nucleotide sequence consists of at least 400 contiguous nucleotide sequences within SEQ. ID NO: 5. In embodiments, the 5' homology arm nucleotide sequence consists of at least 500 contiguous nucleotide sequences within SEQ. ID NO: 5. In embodiments, the 5' homology arm nucleotide sequence consists of at least 600 contiguous nucleotide sequences within SEQ. ID NO: 5. In embodiments, the 5' homology arm nucleotide sequence consists of at least 700 contiguous nucleotide sequences within SEQ. ID NO: 5. In embodiments, the 5' homology arm nucleotide sequence consists of at least 800 contiguous nucleotide sequences within SEQ. ID NO: 5. In embodiments, the 5' homology arm nucleotide sequence consists of at least 900 contiguous nucleotide sequences within SEQ. ID NO: 5. In embodiments, the 5' homology arm nucleotide sequence consists of at least 1000 contiguous nucleotide sequences within SEQ. ID NO: 5. In embodiments, the 5' homology arm nucleotide sequence consists of at least 1100 contiguous nucleotide sequences within SEQ. ID NO: 5. In embodiments, the 5' homology arm nucleotide sequence consists of at least 1200 contiguous nucleotide sequences within SEQ. ID NO: 5. In embodiments, the 5' homology arm nucleotide sequence consists of at least 1300 contiguous nucleotide sequences within SEQ. ID NO: 5. In embodiments, the 5' homology arm nucleotide sequence consists of at least 1400 contiguous nucleotide sequences within SEQ. ID NO: 5. In embodiments, the 5' homology arm nucleotide sequence consists of at least 1500 contiguous nucleotide sequences within SEQ. ID NO: 5. In embodiments, the 5' homology arm nucleotide sequence consists of at least 1600 contiguous nucleotide sequences within SEQ. ID NO: 5. In embodiments, the 5' homology arm nucleotide sequence consists of at least 1700 contiguous nucleotide sequences within SEQ. ID NO: 5. In embodiments, the 5' homology arm nucleotide sequence consists of at least 1800 contiguous nucleotide sequences within SEQ. ID NO: 5. In embodiments, the 5' homology arm nucleotide sequence consists of at least 1900 contiguous nucleotide sequences within SEQ. ID NO: 5.

In embodiments, the 3' homology arm nucleotide sequence consists of at least 200 contiguous nucleotide sequences within SEQ. ID NO: 6. In embodiments, the 3' homology arm nucleotide sequence consists of at least 300 contiguous nucleotide sequences within SEQ. ID NO: 6. In embodiments, the 3' homology arm nucleotide sequence consists of at least 400 contiguous nucleotide sequences within SEQ. ID NO: 6. In embodiments, the 3' homology arm nucleotide sequence consists of at least 500 contiguous nucleotide sequences within SEQ. ID NO: 6. In embodiments, the 3' homology arm nucleotide sequence consists of at least 600 contiguous nucleotide sequences within SEQ. ID NO: 6. In embodiments, the 3' homology arm nucleotide sequence consists of at least 700 contiguous nucleotide sequences within SEQ. ID NO: 6. In embodiments, the 3' homology arm nucleotide sequence consists of at least 800 contiguous nucleotide sequences within SEQ. ID NO: 6. In embodiments, the 3' homology arm nucleotide sequence consists of at least 900 contiguous nucleotide sequences within SEQ. ID NO: 6. In embodiments, the 3' homology arm nucleotide sequence consists of at least 1000 contiguous nucleotide sequences within SEQ. ID NO: 6. In embodiments, the 3' homology arm nucleotide sequence consists of at least 1100 contiguous nucleotide sequences within SEQ. ID NO: 6. In embodiments, the 3' homology arm nucleotide sequence consists of at least 1200 contiguous nucleotide sequences within SEQ. ID NO: 6. In embodiments, the 3' homology arm nucleotide sequence consists of at least 1300 contiguous nucleotide sequences within SEQ. ID NO: 6. In embodiments, the 3' homology arm nucleotide sequence consists of at least 1400 contiguous nucleotide sequences within SEQ. ID NO: 6. In embodiments, the 3' homology arm nucleotide sequence consists of at least 1500 contiguous nucleotide sequences within SEQ. ID NO: 6. In embodiments, the 3' homology arm nucleotide sequence consists of at least 1600 contiguous nucleotide sequences within SEQ. ID NO: 6. In embodiments, the 3' homology arm nucleotide sequence consists of at least 1700 contiguous nucleotide sequences within SEQ. ID NO: 6. In embodiments, the 3' homology arm nucleotide sequence consists of at least 1800 contiguous nucleotide sequences within SEQ. ID NO: 6. In embodiments, the 3' homology arm nucleotide sequence consists of at least 1900 contiguous nucleotide sequences within SEQ. ID NO: 6.

In embodiments, the 5' homology arm nucleotide sequence consists of at least 200 contiguous nucleotide sequences within SEQ. ID NO: 7. In embodiments, the 5' homology arm nucleotide sequence consists of at least 300 contiguous nucleotide sequences within SEQ. ID NO: 7. In embodiments, the 5' homology arm nucleotide sequence consists of at least 400 contiguous nucleotide sequences within SEQ. ID NO: 7. In embodiments, the 5' homology arm nucleotide sequence consists of at least 500 contiguous nucleotide sequences within SEQ. ID NO: 7. In embodiments, the 5' homology arm nucleotide sequence consists of at least 600 contiguous nucleotide sequences within SEQ. ID NO: 7. In embodiments, the 5' homology arm nucleotide sequence consists of at least 700 contiguous nucleotide sequences within SEQ. ID NO: 7. In embodiments, the 5' homology arm nucleotide sequence consists of at least 800 contiguous nucleotide sequences within SEQ. ID NO: 7. In embodiments, the 5' homology arm nucleotide sequence consists of at least 900 contiguous nucleotide sequences within SEQ. ID NO: 7. In embodiments, the 5' homology arm nucleotide sequence consists of at least 1000 contiguous nucleotide sequences within SEQ. ID NO: 7. In embodiments, the 5' homology arm nucleotide sequence consists of at least 1100 contiguous nucleotide sequences within SEQ. ID NO: 7. In embodiments, the 5' homology arm nucleotide sequence consists of at least 1200 contiguous nucleotide sequences within SEQ. ID NO: 7. In embodiments, the 5' homology arm nucleotide sequence consists of at least 1300 contiguous nucleotide sequences within SEQ. ID NO: 7. In embodiments, the 5' homology arm nucleotide sequence consists of at least 1400 contiguous nucleotide sequences within SEQ. ID NO: 7. In embodiments, the 5' homology arm nucleotide sequence consists of at least 1500 contiguous nucleotide sequences within SEQ. ID NO: 7. In embodiments, the 5' homology arm nucleotide sequence consists of at least 1600 contiguous nucleotide sequences within SEQ. ID NO: 7. In embodiments, the 5' homology arm nucleotide sequence consists of at least 1700 contiguous nucleotide sequences within SEQ. ID NO: 7. In embodiments, the 5' homology arm nucleotide sequence consists of at least 1800 contiguous nucleotide sequences within SEQ. ID NO: 7. In embodiments, the 5' homology arm nucleotide sequence consists of at least 1900 contiguous nucleotide sequences within SEQ. ID NO: 7.

In embodiments, the 3' homology arm nucleotide sequence consists of at least 200 contiguous nucleotide sequences within SEQ. ID NO: 8. In embodiments, the 3' homology arm nucleotide sequence consists of at least 300 contiguous nucleotide sequences within SEQ. ID NO: 8. In embodiments, the 3' homology arm nucleotide sequence consists of at least 400 contiguous nucleotide sequences within SEQ. ID NO: 8. In embodiments, the 3' homology arm nucleotide sequence consists of at least 500 contiguous nucleotide sequences within SEQ. ID NO: 8. In embodiments, the 3' homology arm nucleotide sequence consists of at least 600 contiguous nucleotide sequences within SEQ. ID NO: 8. In embodiments, the 3' homology arm nucleotide sequence consists of at least 700 contiguous nucleotide sequences within SEQ. ID NO: 8. In embodiments, the 3' homology arm nucleotide sequence consists of at least 800 contiguous nucleotide sequences within SEQ. ID NO: 8. In embodiments, the 3' homology arm nucleotide sequence consists of at least 900 contiguous nucleotide sequences within SEQ. ID NO: 8. In embodiments, the 3' homology arm nucleotide sequence consists of at least 1000 contiguous nucleotide sequences within SEQ. ID NO: 8. In embodiments, the 3' homology arm nucleotide sequence consists of at least 1100 contiguous nucleotide sequences within SEQ. ID NO: 8. In embodiments, the 3' homology arm nucleotide sequence consists of at least 1200 contiguous nucleotide sequences within SEQ. ID NO: 8. In embodiments, the 3' homology arm nucleotide sequence consists of at least 1300 contiguous nucleotide sequences within SEQ. ID NO: 8. In embodiments, the 3' homology arm nucleotide sequence consists of at least 1400 contiguous nucleotide sequences within SEQ. ID NO: 8. In embodiments, the 3' homology arm nucleotide sequence consists of at least 1500 contiguous nucleotide sequences within SEQ. ID NO: 8. In embodiments, the 3' homology arm nucleotide sequence consists of at least 1600 contiguous nucleotide sequences within SEQ. ID NO: 8. In embodiments, the 3' homology arm nucleotide sequence consists of at least 1700 contiguous nucleotide sequences within SEQ. ID NO: 8. In embodiments, the 3' homology arm nucleotide sequence consists of at least 1800 contiguous nucleotide sequences within SEQ. ID NO: 8. In embodiments, the 3' homology arm nucleotide sequence consists of at least 1900 contiguous nucleotide sequences within SEQ. ID NO: 8.

In embodiments, the 5' homology arm nucleotide sequence consists of at least 200 contiguous nucleotide sequences within SEQ. ID NO: 9. In embodiments, the 5' homology arm nucleotide sequence consists of at least 300 contiguous nucleotide sequences within SEQ. ID NO: 9. In embodiments, the 5' homology arm nucleotide sequence consists of at least 400 contiguous nucleotide sequences within SEQ. ID NO: 9. In embodiments, the 5' homology arm nucleotide sequence consists of at least 500 contiguous nucleotide sequences within SEQ. ID NO: 9. In embodiments, the 5' homology arm nucleotide sequence consists of at least 600 contiguous nucleotide sequences within SEQ. ID NO: 9. In embodiments, the 5' homology arm nucleotide sequence consists of at least 700 contiguous nucleotide sequences within SEQ. ID NO: 9. In embodiments, the 5' homology arm nucleotide sequence consists of at least 800 contiguous nucleotide sequences within SEQ. ID NO: 9. In embodiments, the 5' homology arm nucleotide sequence consists of at least 900 contiguous nucleotide sequences within SEQ. ID NO: 9. In embodiments, the 5' homology arm nucleotide sequence consists of at least 1000 contiguous nucleotide sequences within SEQ. ID NO: 9. In embodiments, the 5' homology arm nucleotide sequence consists of at least 1100 contiguous nucleotide sequences within SEQ. ID NO: 9. In embodiments, the 5' homology arm nucleotide sequence consists of at least 1200 contiguous nucleotide sequences within SEQ. ID NO: 9. In embodiments, the 5' homology arm nucleotide sequence consists of at least 1300 contiguous nucleotide sequences within SEQ. ID NO: 9. In embodiments, the 5' homology arm nucleotide sequence consists of at least 1400 contiguous nucleotide sequences within SEQ. ID NO: 9. In embodiments, the 5' homology arm nucleotide sequence consists of at least 1500 contiguous nucleotide sequences within SEQ. ID NO: 9. In embodiments, the 5' homology arm nucleotide sequence consists of at least 1600 contiguous nucleotide sequences within SEQ. ID NO: 9. In embodiments, the 5' homology arm nucleotide sequence consists of at least 1700 contiguous nucleotide sequences within SEQ. ID NO: 9. In embodiments, the 5' homology arm nucleotide sequence consists of at least 1800 contiguous nucleotide sequences within SEQ. ID NO: 9. In embodiments, the 5' homology arm nucleotide sequence consists of at least 1900 contiguous nucleotide sequences within SEQ. ID NO: 9.

In embodiments, the 3' homology arm nucleotide sequence consists of at least 200 contiguous nucleotide sequences within SEQ. ID NO: 10. In embodiments, the 3' homology arm nucleotide sequence consists of at least 300 contiguous nucleotide sequences within SEQ. ID NO: 10. In embodiments, the 3' homology arm nucleotide sequence consists of at least 400 contiguous nucleotide sequences within SEQ. ID NO: 10. In embodiments, the 3' homology arm nucleotide sequence consists of at least 500 contiguous nucleotide sequences within SEQ. ID NO: 10. In embodiments, the 3' homology arm nucleotide sequence consists of at least 600 contiguous nucleotide sequences within SEQ. ID NO: 10. In embodiments, the 3' homology arm nucleotide sequence consists of at least 700 contiguous nucleotide sequences within SEQ. ID NO: 10. In embodiments, the 3' homology arm nucleotide sequence consists of at least 800 contiguous nucleotide sequences within SEQ. ID NO: 10. In embodiments, the 3' homology arm nucleotide sequence consists of at least 900 contiguous nucleotide sequences within SEQ. ID NO: 10. In embodiments, the 3' homology arm nucleotide sequence consists of at least 1000 contiguous nucleotide sequences within SEQ. ID NO: 10. In embodiments, the 3' homology arm nucleotide sequence consists of at least 1100 contiguous nucleotide sequences within SEQ. ID NO: 10. In embodiments, the 3' homology arm nucleotide sequence consists of at least 1200 contiguous nucleotide sequences within SEQ. ID NO: 10. In embodiments, the 3' homology arm nucleotide sequence consists of at least 1300 contiguous nucleotide sequences within SEQ. ID NO: 10. In embodiments, the 3' homology arm nucleotide sequence consists of at least 1400 contiguous nucleotide sequences within SEQ. ID NO: 10. In embodiments, the 3' homology arm nucleotide sequence consists of at least 1500 contiguous nucleotide sequences within SEQ. ID NO: 10. In embodiments, the 3' homology arm nucleotide sequence consists of at least 1600 contiguous nucleotide sequences within SEQ. ID NO: 10. In embodiments, the 3' homology arm nucleotide sequence consists of at least 1700 contiguous nucleotide sequences within SEQ. ID NO: 10. In embodiments, the 3' homology arm nucleotide sequence consists of at least 1800 contiguous nucleotide sequences within SEQ. ID NO: 10. In embodiments, the 3' homology arm nucleotide sequence consists of at least 1900 contiguous nucleotide sequences within SEQ. ID NO: 10.

In embodiments, the 5' homology arm nucleotide sequence consists of at least 200 contiguous nucleotide sequences within SEQ. ID NO: 11. In embodiments, the 5' homology arm nucleotide sequence consists of at least 300 contiguous nucleotide sequences within SEQ. ID NO: 11. In embodiments, the 5' homology arm nucleotide sequence consists of at least 400 contiguous nucleotide sequences within SEQ. ID NO: 11. In embodiments, the 5' homology arm nucleotide sequence consists of at least 500 contiguous nucleotide sequences within SEQ. ID NO: 11. In embodiments, the 5' homology arm nucleotide sequence consists of at least 600 contiguous nucleotide sequences within SEQ. ID NO: 11. In embodiments, the 5' homology arm nucleotide sequence consists of at least 700 contiguous nucleotide sequences within SEQ. ID NO: 11. In embodiments, the 5' homology arm nucleotide sequence consists of at least 800 contiguous nucleotide sequences within SEQ. ID NO: 11. In embodiments, the 5' homology arm nucleotide sequence consists of at least 900 contiguous nucleotide sequences within SEQ. ID NO: 11. In embodiments, the 5' homology arm nucleotide sequence consists of at least 1000 contiguous nucleotide sequences within SEQ. ID NO: 11. In embodiments, the 5' homology arm nucleotide sequence consists of at least 1100 contiguous nucleotide sequences within SEQ. ID NO: 11. In embodiments, the 5' homology arm nucleotide sequence consists of at least 1200 contiguous nucleotide sequences within SEQ. ID NO: 11. In embodiments, the 5' homology arm nucleotide sequence consists of at least 1300 contiguous nucleotide sequences within SEQ. ID NO: 11. In embodiments, the 5' homology arm nucleotide sequence consists of at least 1400 contiguous nucleotide sequences within SEQ. ID NO: 11. In embodiments, the 5' homology arm nucleotide sequence consists of at least 1500 contiguous nucleotide sequences within SEQ. ID NO: 11. In embodiments, the 5' homology arm nucleotide sequence consists of at least 1600 contiguous nucleotide sequences within SEQ. ID NO: 11. In embodiments, the 5' homology arm nucleotide sequence consists of at least 1700 contiguous nucleotide sequences within SEQ. ID NO: 11. In embodiments, the 5' homology arm nucleotide sequence consists of at least 1800 contiguous nucleotide sequences within SEQ. ID NO: 11. In embodiments, the 5' homology arm nucleotide sequence consists of at least 1900 contiguous nucleotide sequences within SEQ. ID NO: 11.

In embodiments, the 3' homology arm nucleotide sequence consists of at least 200 contiguous nucleotide sequences within SEQ. ID NO: 12. In embodiments, the 3' homology arm nucleotide sequence consists of at least 300 contiguous nucleotide sequences within SEQ. ID NO: 12. In embodiments, the 3' homology arm nucleotide sequence consists of at least 400 contiguous nucleotide sequences within SEQ. ID NO: 12. In embodiments, the 3' homology arm nucleotide sequence consists of at least 500 contiguous nucleotide sequences within SEQ. ID NO: 12. In embodiments, the 3' homology arm nucleotide sequence consists of at least 600 contiguous nucleotide sequences within SEQ. ID NO: 12. In embodiments, the 3' homology arm nucleotide sequence consists of at least 700 contiguous nucleotide sequences within SEQ. ID NO: 12. In embodiments, the 3' homology arm nucleotide sequence consists of at least 800 contiguous nucleotide sequences within SEQ. ID NO: 12. In embodiments, the 3' homology arm nucleotide sequence consists of at least 900 contiguous nucleotide sequences within SEQ. ID NO: 12. In embodiments, the 3' homology arm nucleotide sequence consists of at least 1000 contiguous nucleotide sequences within SEQ. ID NO: 12. In embodiments, the 3' homology arm nucleotide sequence consists of at least 1100 contiguous nucleotide sequences within SEQ. ID NO: 12. In embodiments, the 3' homology arm nucleotide sequence consists of at least 1200 contiguous nucleotide sequences within SEQ. ID NO: 12. In embodiments, the 3' homology arm nucleotide sequence consists of at least 1300 contiguous nucleotide sequences within SEQ. ID NO: 12. In embodiments, the 3' homology arm nucleotide sequence consists of at least 1400 contiguous nucleotide sequences within SEQ. ID NO: 12. In embodiments, the 3' homology arm nucleotide sequence consists of at least 1500 contiguous nucleotide sequences within SEQ. ID NO: 12. In embodiments, the 3' homology arm nucleotide sequence consists of at least 1600 contiguous nucleotide sequences within SEQ. ID NO: 12. In embodiments, the 3' homology arm nucleotide sequence consists of at least 1700 contiguous nucleotide sequences within SEQ. ID NO: 12. In embodiments, the 3' homology arm nucleotide sequence consists of at least 1800 contiguous nucleotide sequences within SEQ. ID NO: 12. In embodiments, the 3' homology arm nucleotide sequence consists of at least 1900 contiguous nucleotide sequences within SEQ. ID NO: 12.

In embodiments, the 5' homology arm nucleotide sequence consists of at least 200 contiguous nucleotide sequences within SEQ. ID NO: 13. In embodiments, the 5' homology arm nucleotide sequence consists of at least 300 contiguous nucleotide sequences within SEQ. ID NO: 13. In embodiments, the 5' homology arm nucleotide sequence consists of at least 400 contiguous nucleotide sequences within SEQ. ID NO: 13. In embodiments, the 5' homology arm nucleotide sequence consists of at least 500 contiguous nucleotide sequences within SEQ. ID NO: 13. In embodiments, the 5' homology arm nucleotide sequence consists of at least 600 contiguous nucleotide sequences within SEQ. ID NO: 13. In embodiments, the 5' homology arm nucleotide sequence consists of at least 700 contiguous nucleotide sequences within SEQ. ID NO: 13. In embodiments, the 5' homology arm nucleotide sequence consists of at least 800 contiguous nucleotide sequences within SEQ. ID NO: 13. In embodiments, the 5' homology arm nucleotide sequence consists of at least 900 contiguous nucleotide sequences within SEQ. ID NO: 13. In embodiments, the 5' homology arm nucleotide sequence consists of at least 1000 contiguous nucleotide sequences within SEQ. ID NO: 13. In embodiments, the 5' homology arm nucleotide sequence consists of at least 1100 contiguous nucleotide sequences within SEQ. ID NO: 13. In embodiments, the 5' homology arm nucleotide sequence consists of at least 1200 contiguous nucleotide sequences within SEQ. ID NO: 13. In embodiments, the 5' homology arm nucleotide sequence consists of at least 1300 contiguous nucleotide sequences within SEQ. ID NO: 13. In embodiments, the 5' homology arm nucleotide sequence consists of at least 1400 contiguous nucleotide sequences within SEQ. ID NO: 13. In embodiments, the 5' homology arm nucleotide sequence consists of at least 1500 contiguous nucleotide sequences within SEQ. ID NO: 13. In embodiments, the 5' homology arm nucleotide sequence consists of at least 1600 contiguous nucleotide sequences within SEQ. ID NO: 13. In embodiments, the 5' homology arm nucleotide sequence consists of at least 1700 contiguous nucleotide sequences within SEQ. ID NO: 13. In embodiments, the 5' homology arm nucleotide sequence consists of at least 1800 contiguous nucleotide sequences within SEQ. ID NO: 13. In embodiments, the 5' homology arm nucleotide sequence consists of at least 1900 contiguous nucleotide sequences within SEQ. ID NO: 13.

In embodiments, the 3' homology arm nucleotide sequence consists of at least 200 contiguous nucleotide sequences within SEQ. ID NO: 14. In embodiments, the 3' homology arm nucleotide sequence consists of at least 300 contiguous nucleotide sequences within SEQ. ID NO: 14. In embodiments, the 3' homology arm nucleotide sequence consists of at least 400 contiguous nucleotide sequences within SEQ. ID NO: 14. In embodiments, the 3' homology arm nucleotide sequence consists of at least 500 contiguous nucleotide sequences within SEQ. ID NO: 14. In embodiments, the 3' homology arm nucleotide sequence consists of at least 600 contiguous nucleotide sequences within SEQ. ID NO: 14. In embodiments, the 3' homology arm nucleotide sequence consists of at least 700 contiguous nucleotide sequences within SEQ. ID NO: 14. In embodiments, the 3' homology arm nucleotide sequence consists of at least 800 contiguous nucleotide sequences within SEQ. ID NO: 14. In embodiments, the 3' homology arm nucleotide sequence consists of at least 900 contiguous nucleotide sequences within SEQ. ID NO: 14. In embodiments, the 3' homology arm nucleotide sequence consists of at least 1000 contiguous nucleotide sequences within SEQ. ID NO: 14. In embodiments, the 3' homology arm nucleotide sequence consists of at least 1100 contiguous nucleotide sequences within SEQ. ID NO: 14. In embodiments, the 3' homology arm nucleotide sequence consists of at least 1200 contiguous nucleotide sequences within SEQ. ID NO: 14. In embodiments, the 3' homology arm nucleotide sequence consists of at least 1300 contiguous nucleotide sequences within SEQ. ID NO: 14. In embodiments, the 3' homology arm nucleotide sequence consists of at least 1400 contiguous nucleotide sequences within SEQ. ID NO: 14. In embodiments, the 3' homology arm nucleotide sequence consists of at least 1500 contiguous nucleotide sequences within SEQ. ID NO: 14. In embodiments, the 3' homology arm nucleotide sequence consists of at least 1600 contiguous nucleotide sequences within SEQ. ID NO: 14. In embodiments, the 3' homology arm nucleotide sequence consists of at least 1700 contiguous nucleotide sequences within SEQ. ID NO: 14. In embodiments, the 3' homology arm nucleotide sequence consists of at least 1800 contiguous nucleotide sequences within SEQ. ID NO: 14. In embodiments, the 3' homology arm nucleotide sequence consists of at least 1900 contiguous nucleotide sequences within SEQ. ID NO: 14.

In embodiments, any of the 5' homology arms disclosed herein may be paired with any of the 3' homology arms provided herein. For example, 5' homology arm 1 (SEQ. ID NO: 1) may be paired with 3' homology arm 2 (SEQ. ID NO: 4).

In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

These and other embodiments of the disclosure are provided in more detail herein.

Figure 1:
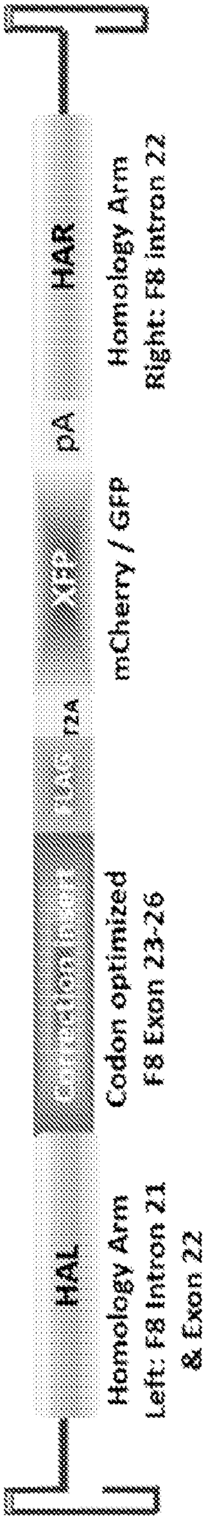
FIG. 1 illustrates the AAV correction vector for editing the I22I inversion of the FVIII gene. The vector comprises a left homology arm that targets the F8 intron 21 and exon 22 region, a codon optimized coding sequence for exons 23-26 in the F8 gene, a FLAG tag, a T2A element, an mCherry/GFP element, a polyadenylation sequence and a right homology arm that targets the F8 intron 22.
Figure 2:
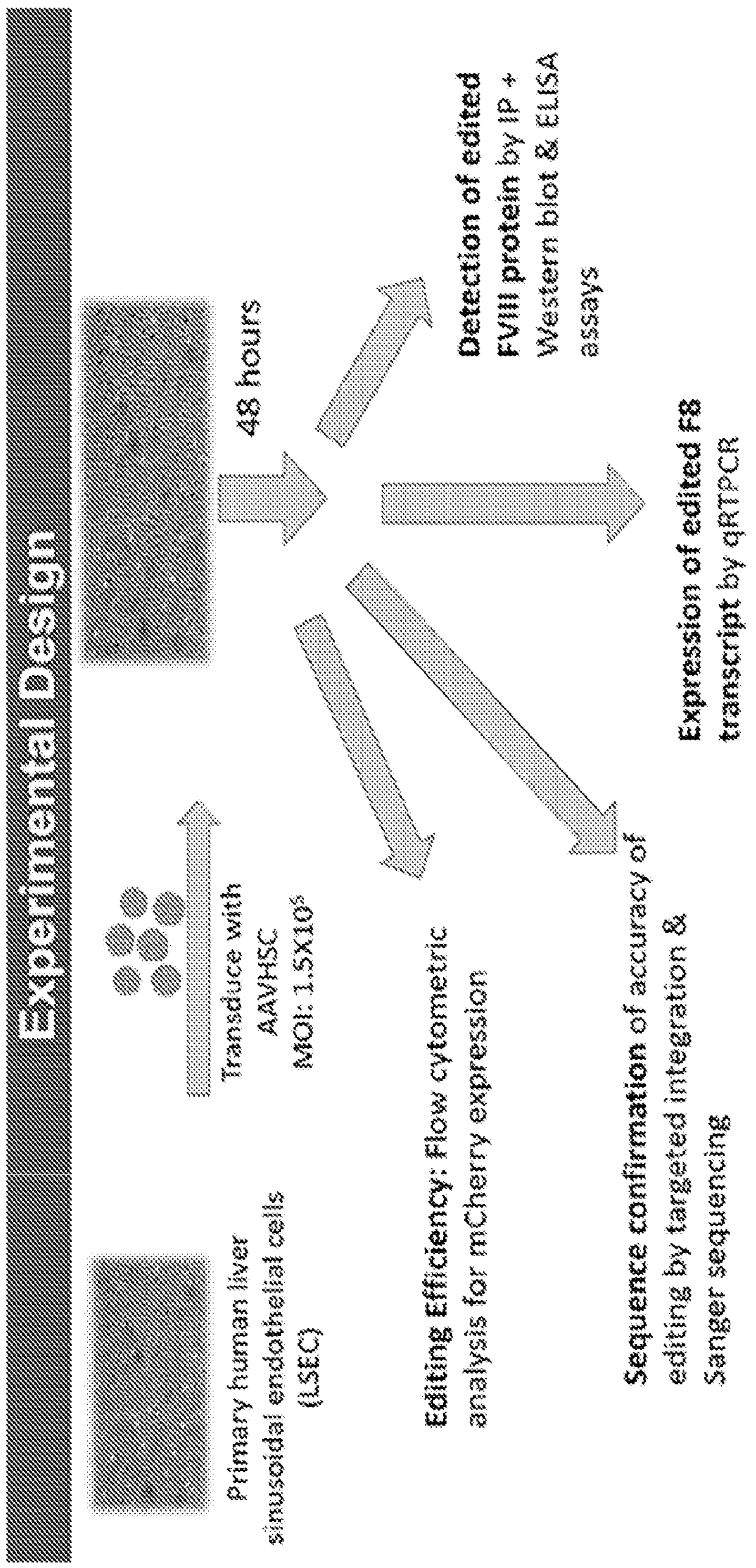
FIG. 2 illustrates the experimental design. After 48 hours of primary human liver cells transduced with AAVHSC, the results were analyzed by flow cytometric analysis for mCherry expression to quantify editing efficiency; the accuracy of editing by targeted integration was confirmed by Sanger sequencing; the expression of edited F8 transcripts were performed by qRTPCR; and detection of edited FVII protein was performed by IP, Western blot and ELISA assays.
Figure 3:
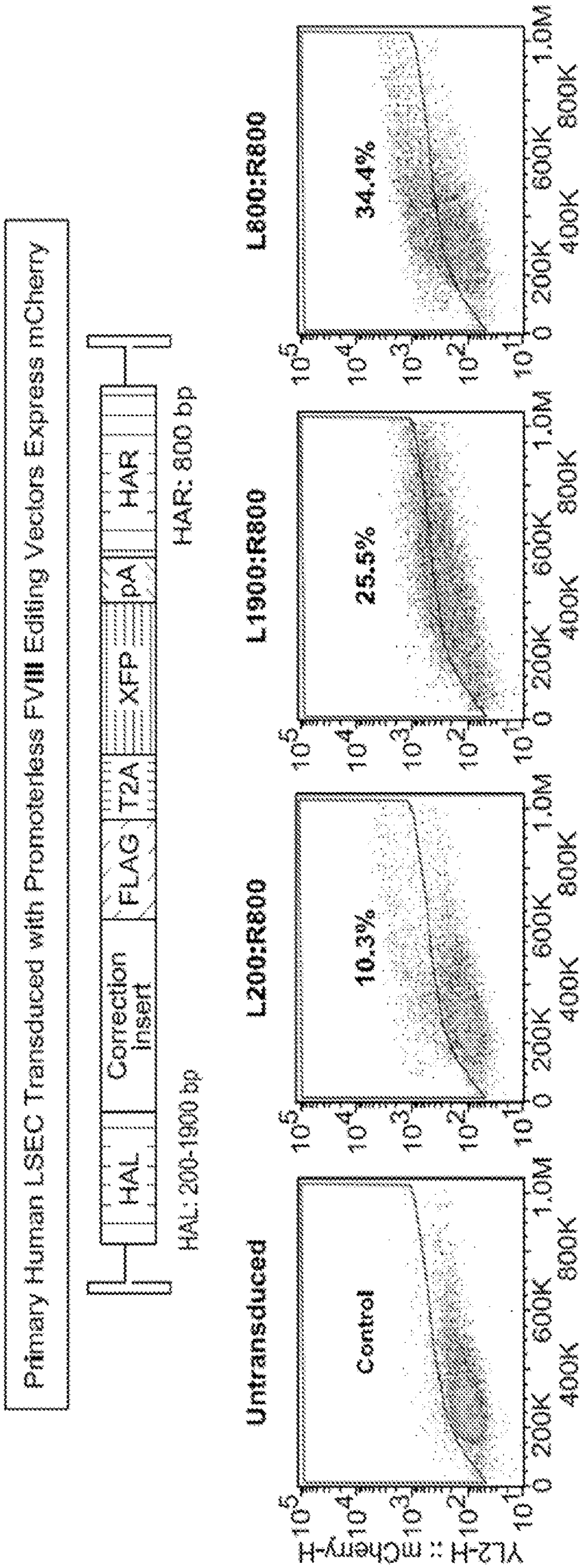
FIG. 3 illustrates that primary human LSEC transduced with promoterless FVIII editing vectors express mCherry. The example shows that the mCherry coding region was targeted to the end of Exon 22 of the FVIII gene; mCherry expression was under the control of the chromosomal FVIII promoter and reflected successful editing of the FVIII gene; mCherry expression was dependent upon homology arm configuration.
Figure 4:
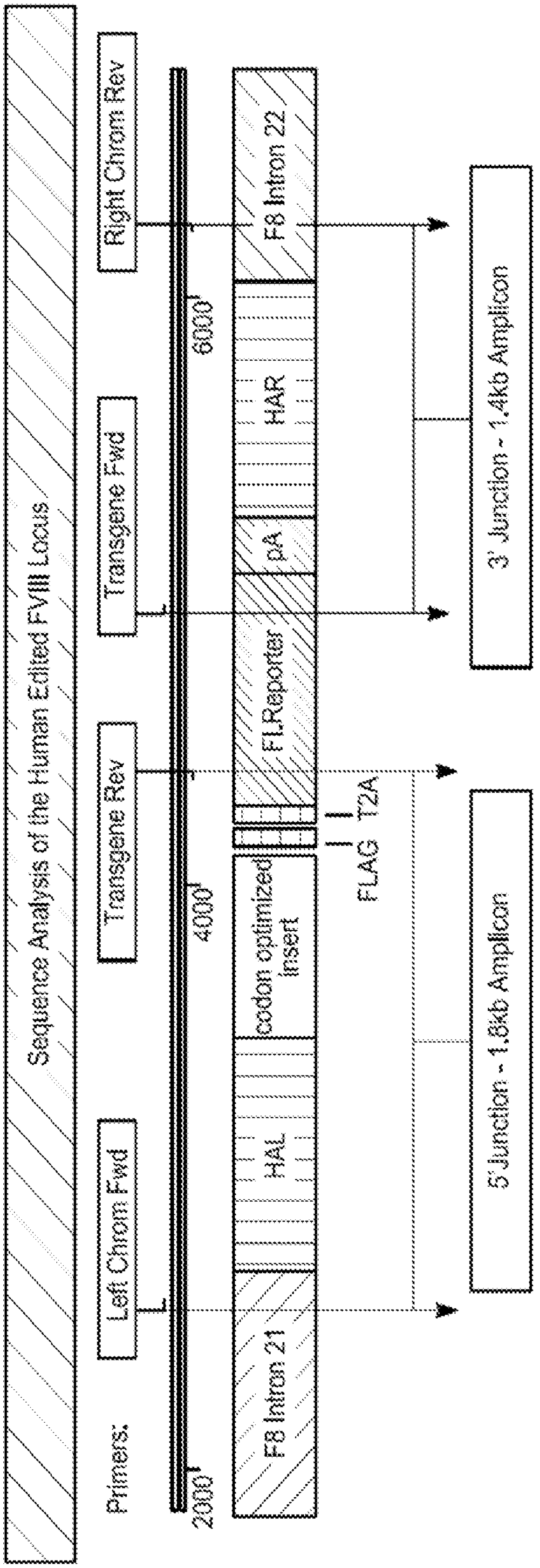
FIG. 4 illustrates the sequence analysis of the human edited FVIII locus. In the example, targeted integration assays were performed using PCR amplification with chromosome-specific primer and an insert-specific primer. The chromosome-specific primer hybridized to a region outside the Homology Arms (HA). Sanger sequencing across the chromosome-HA junctions and insert-HA junctions revealed seamless insertion. The results showed that no insertion/deletion mutations were detected and no AAV ITRs were detected.
Figure 5:
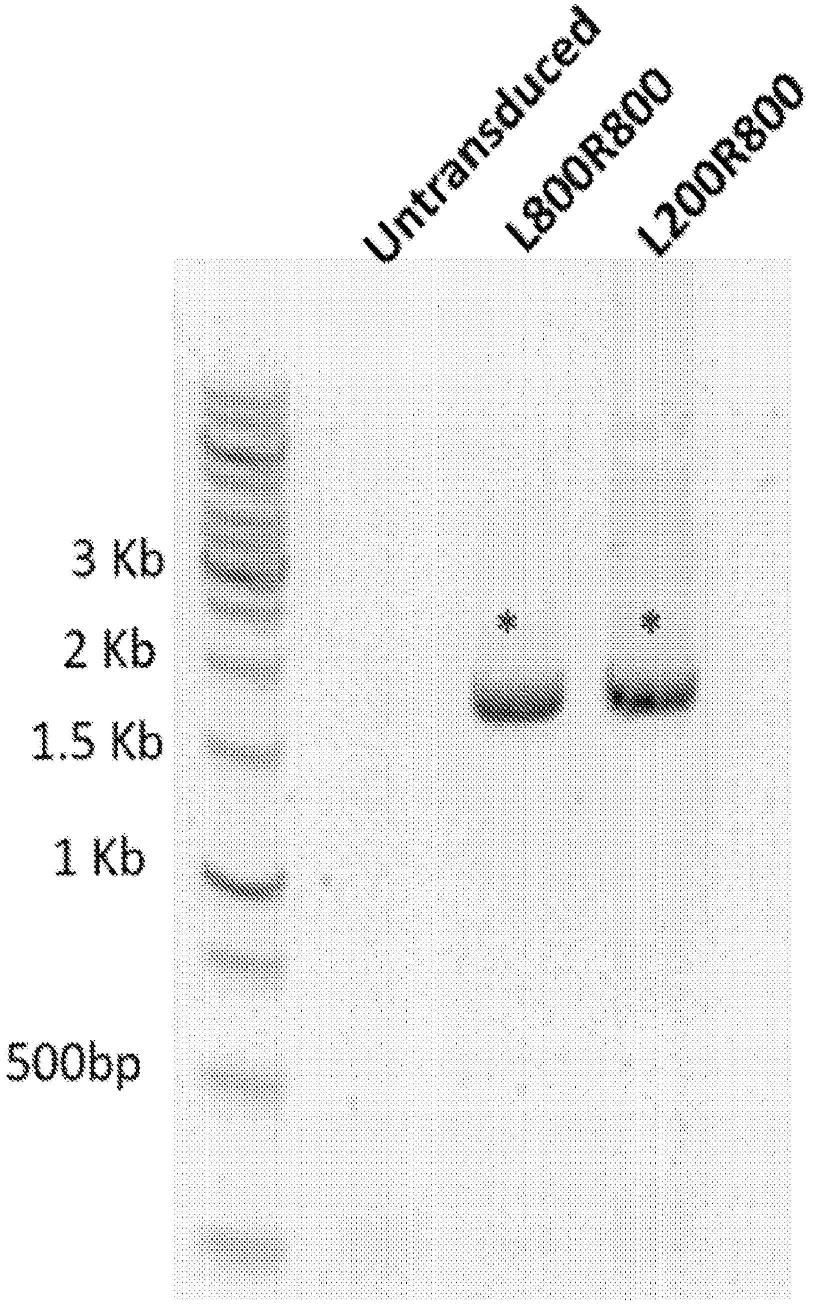
FIG. 5 illustrates amplification of 5' chromosome—homology arm junction in AAVHSC15-edited primary human liver sinusoidal endothelial cells (LSEC). Amplification of the 5' chromosome-HA junction sequence was performed using a mCherry-specific primer & a chromosomal primer complementary to genomic sequences external to the HA. The 1800 bp bands (identified by the asterisks) signify the specific amplification of the 5' junction of the targeted integration of the correction cassette within the FVIII gene. The expected band is present only in transduced, but not untransduced LSECs (asterisks). The 1800 bp band was purified and was sequenced by Sanger sequencing.
Figure 6A:
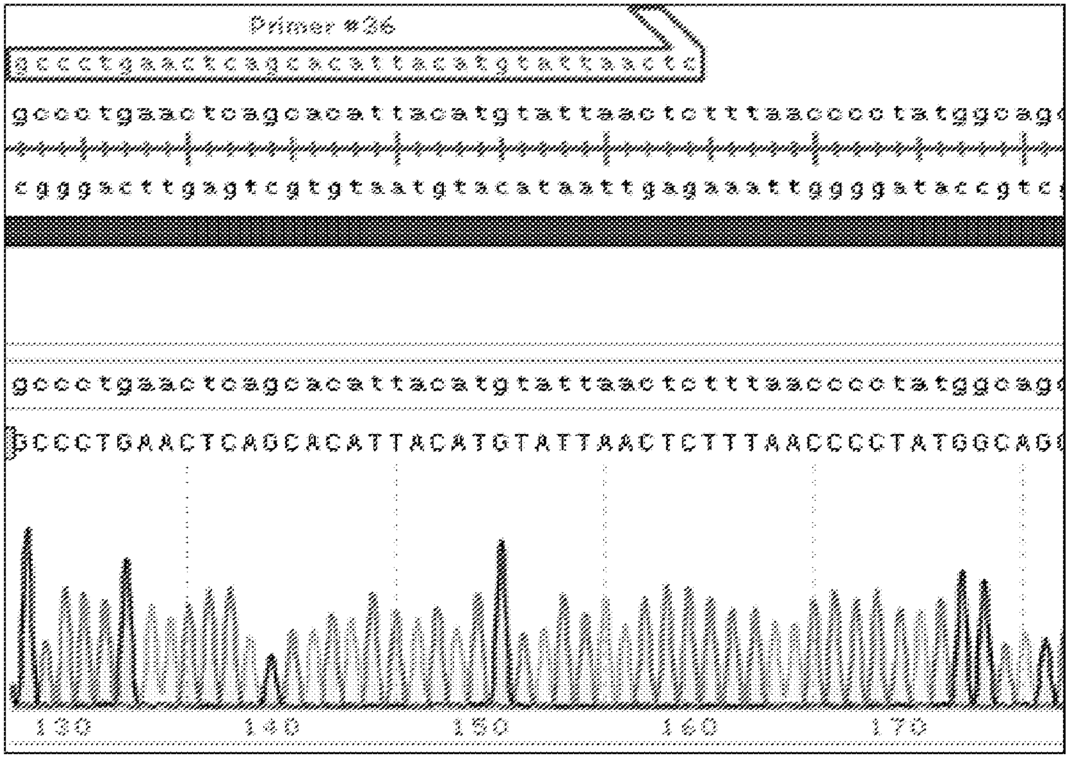
FIG. 6 illustrates that the analyses of junction sequences show seamless insertion of the correction sequence at the end of exon 22 in the FVII gene in primary human LSEC. At each junction, highlighted by the box, the arrow points to the nucleotide sequence associated with the region. The two panels furthest to the left show the nucleotide sequence for the 5' and 3' junctions of the left homology arm and the two panels further to the right show the nucleotide sequences for the 5' and 3' junctions of the right homology arm after targeted insertion into the cellular genome in this example. As presented, AAVHSC15 FVIII editing vectors successfully inserted the codon optimized correction sequence cassette at the end of Exon 22 of the human FVIII gene. There was no evidence of sequence alterations in edited cells within or around the insertion site. No insertion/deletion mutations were detected and no AAV ITRs were detected at the junction sites.
Figure 6B:
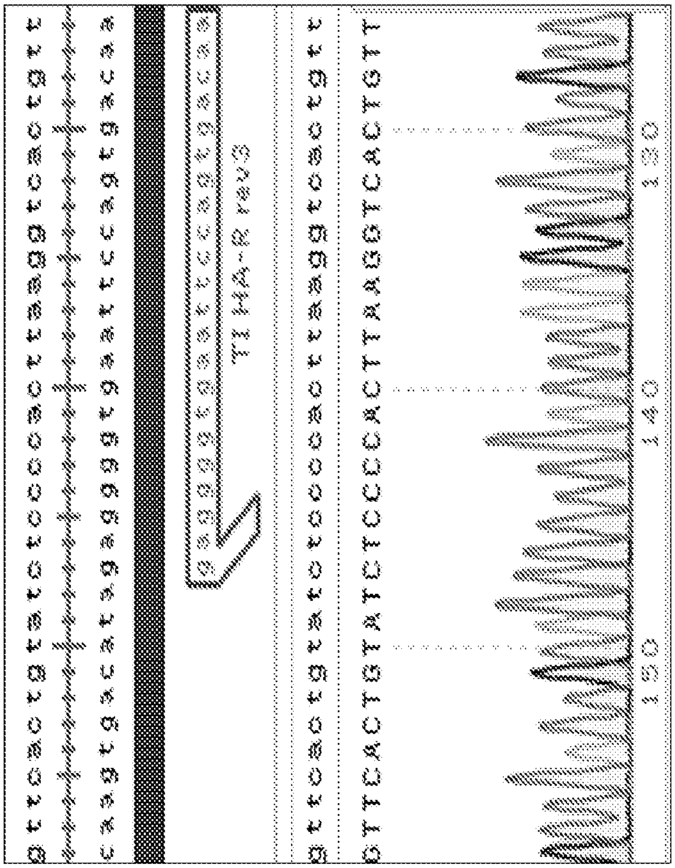
Figure 6C:
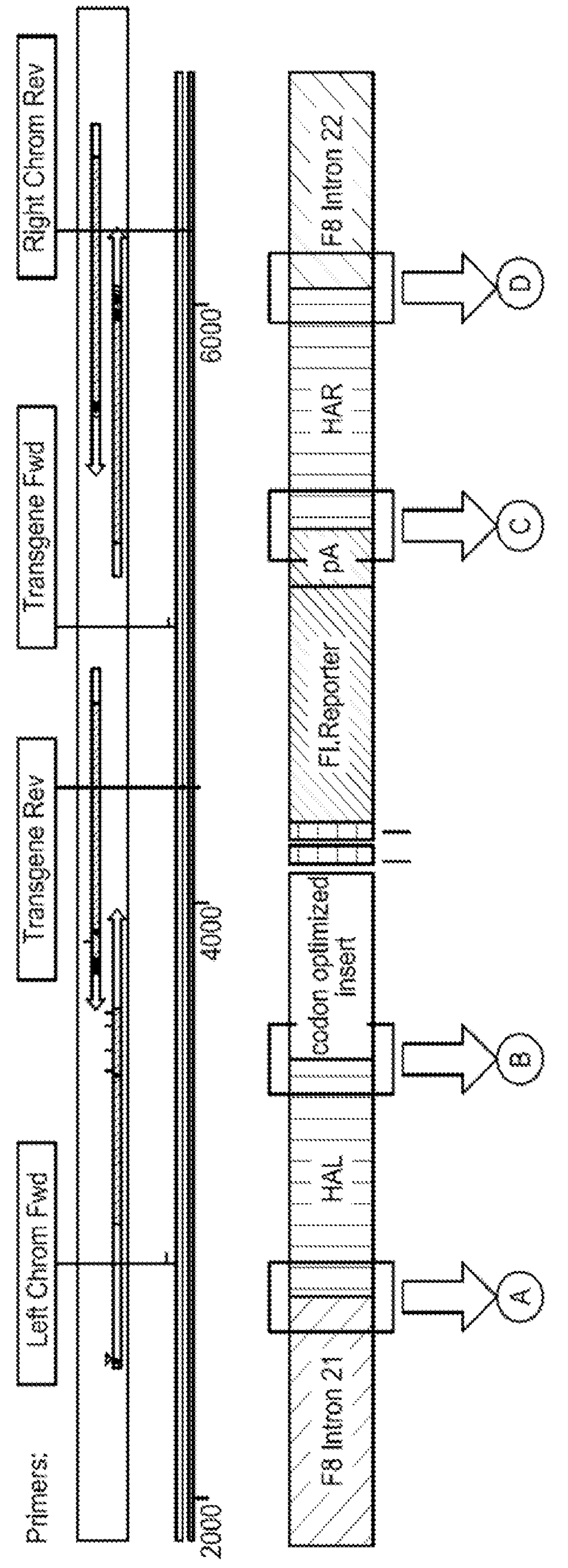
Figure 6D:
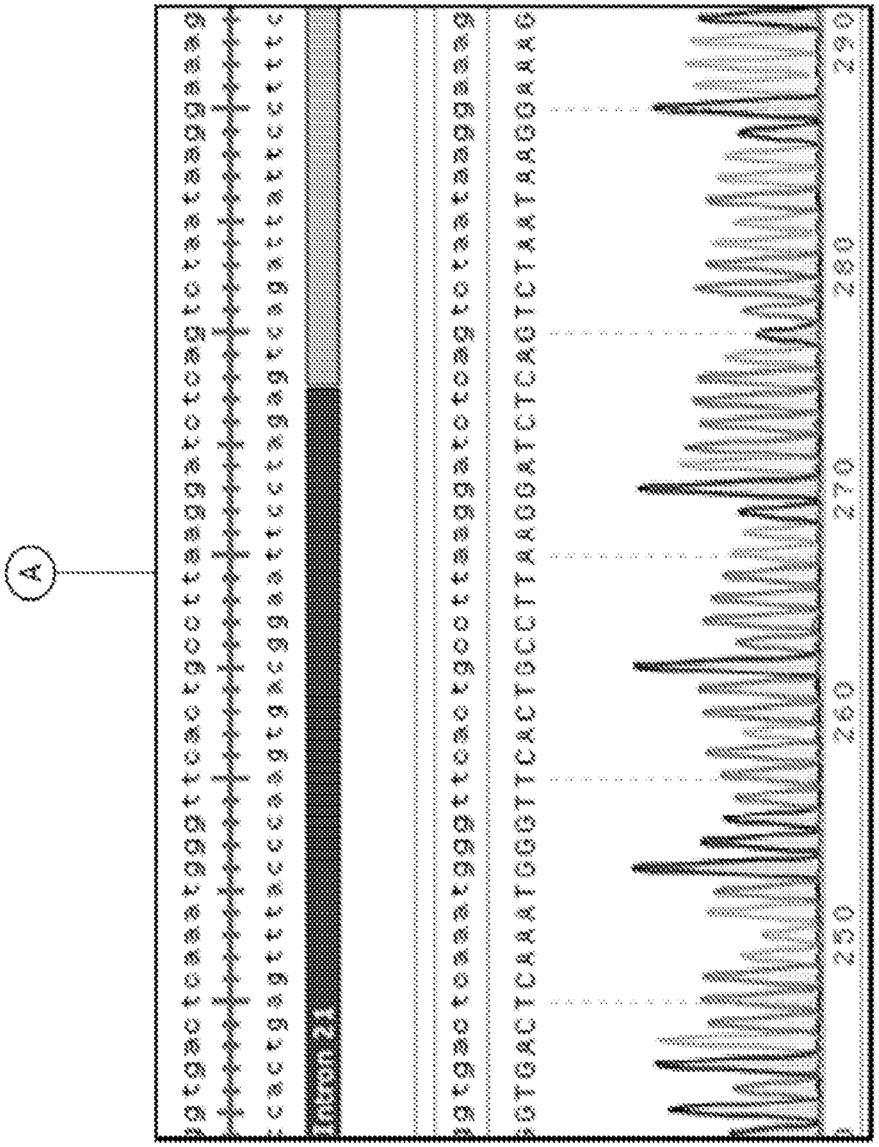
Figure 6E:
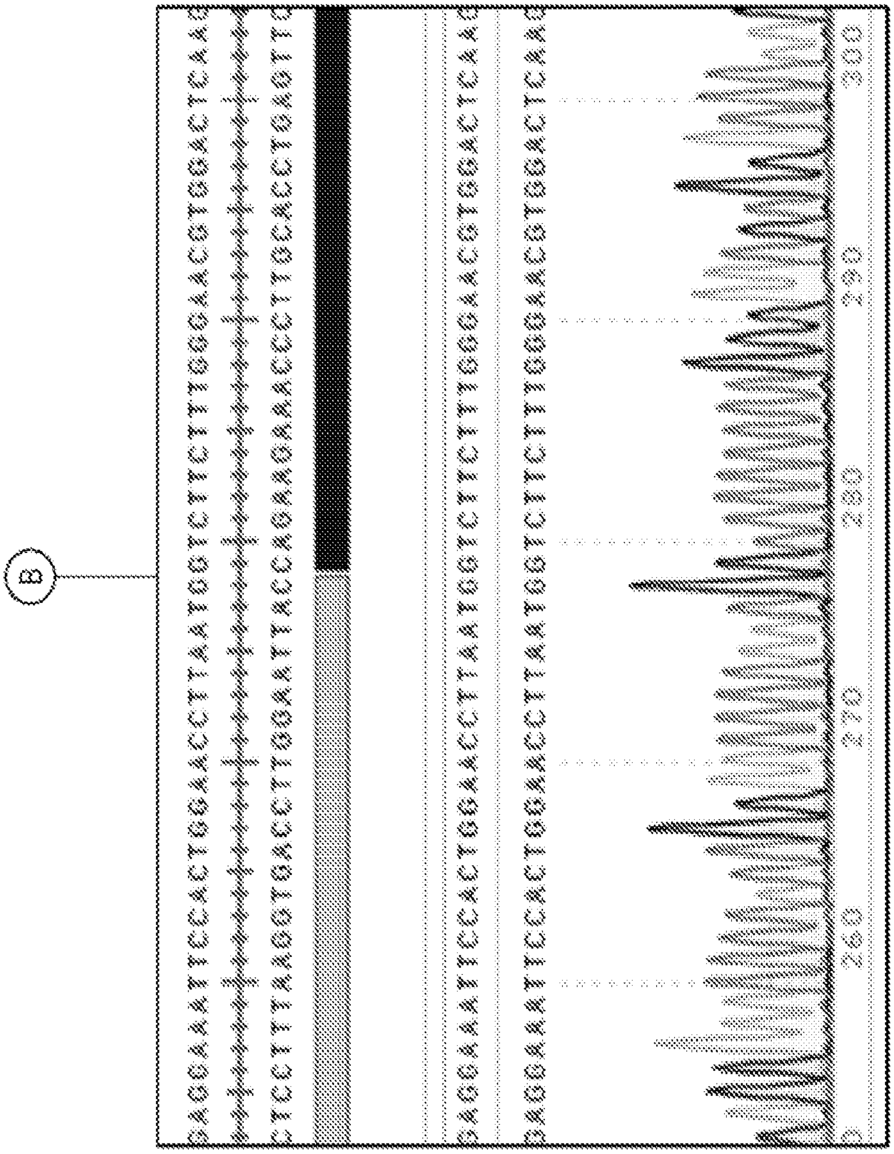
Figure 6F:
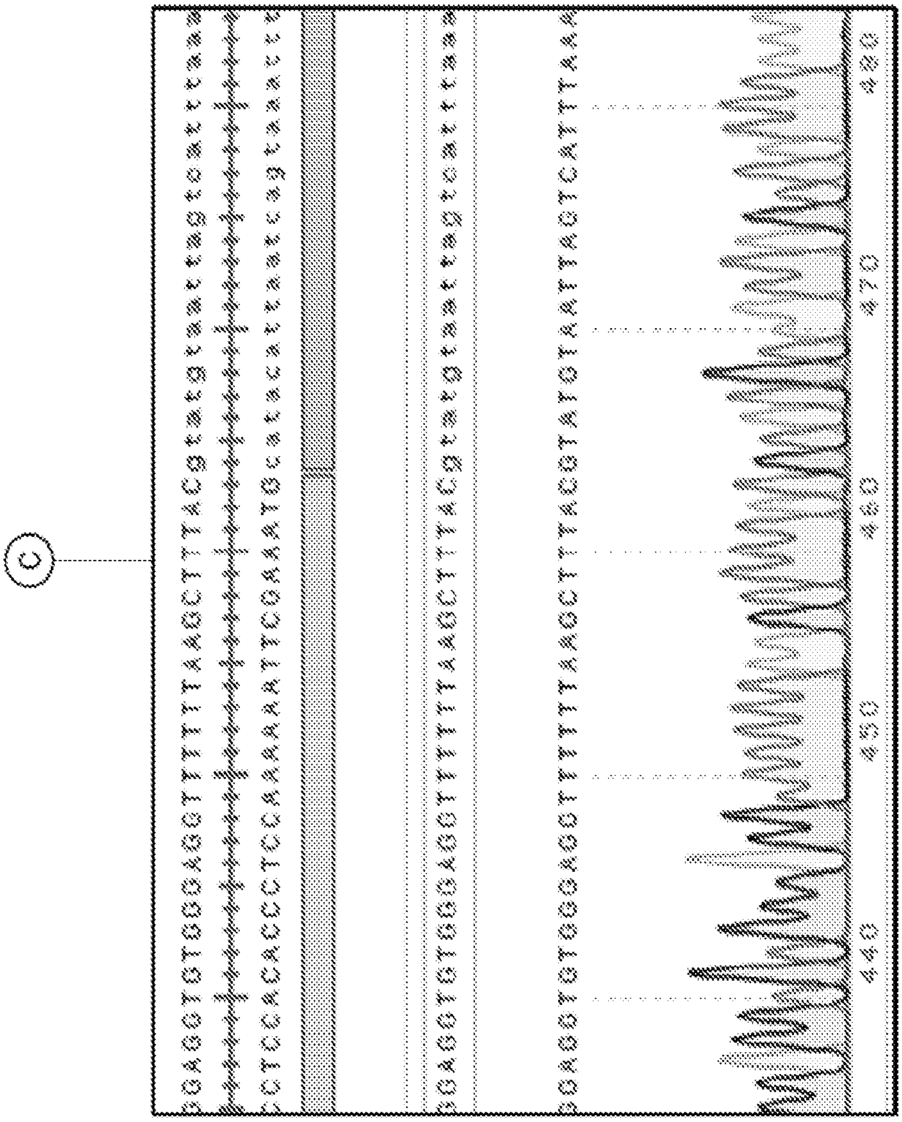
Figure 6G:
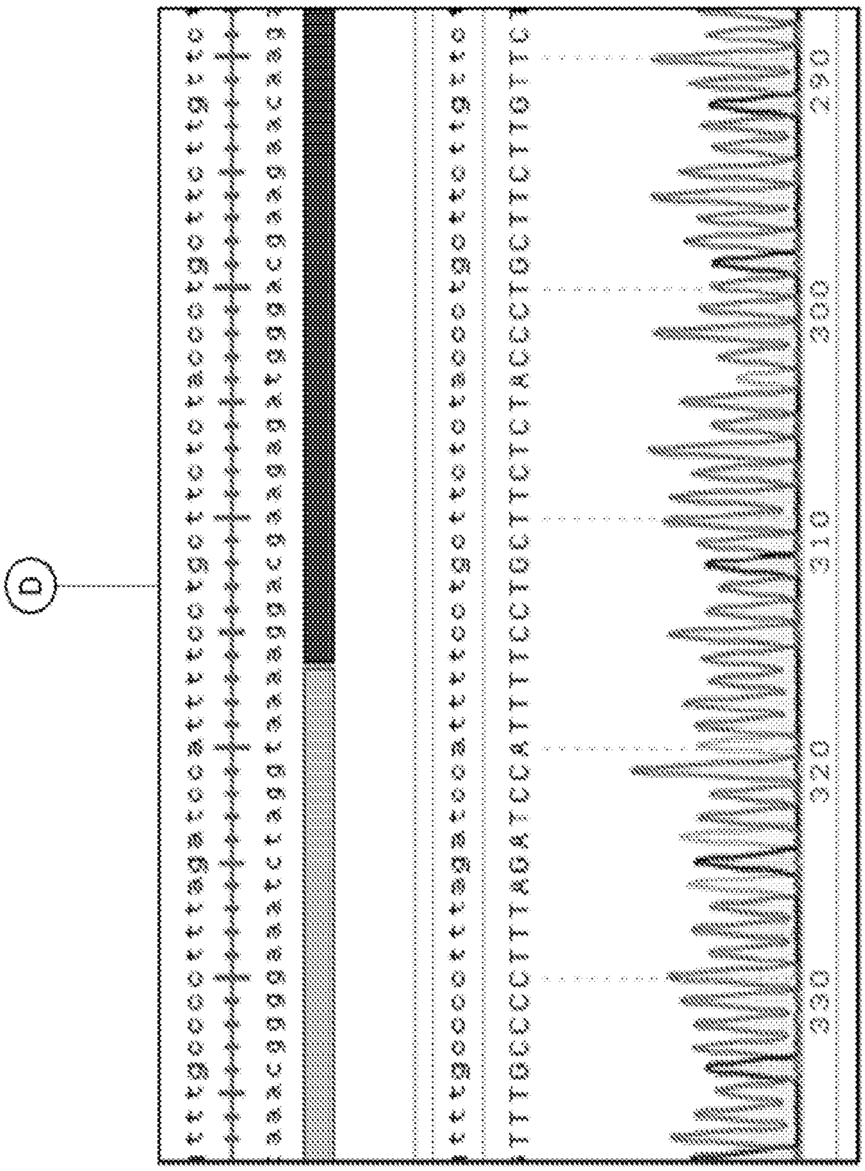
Figure 7A:
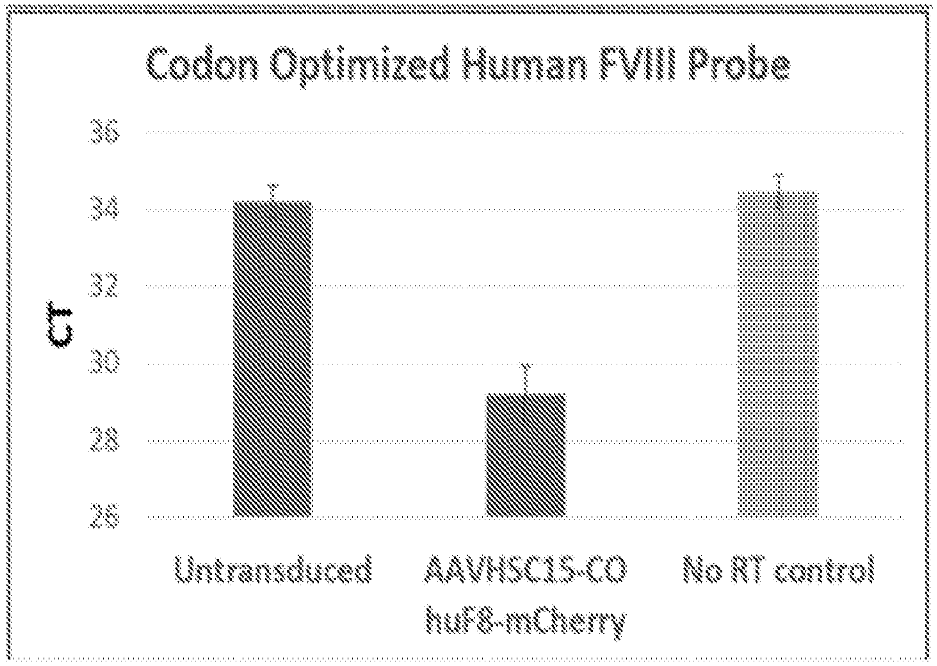
FIG. 7A-7B illustrate the transcription of the codon optimized FVIII transgene in AAVHSC15 edited primary human LSEC. As presented, AAVHSC15-edited primary human LSEC expressed the codon-optimized human F8 gene. Both transduced and untransduced LSEC made FVIII, but edited LSECs show overexpression (signified by lower CT) of the F8. No reverse transcriptase (RT) controls are included as specificity controls. The data presented in FIGS. 7A and 7B showed transcription of the codon optimized F8 correction sequence & mCherry resulting from the successful targeted insertion of the correction sequence into the F8 gene.
Figure 7B:
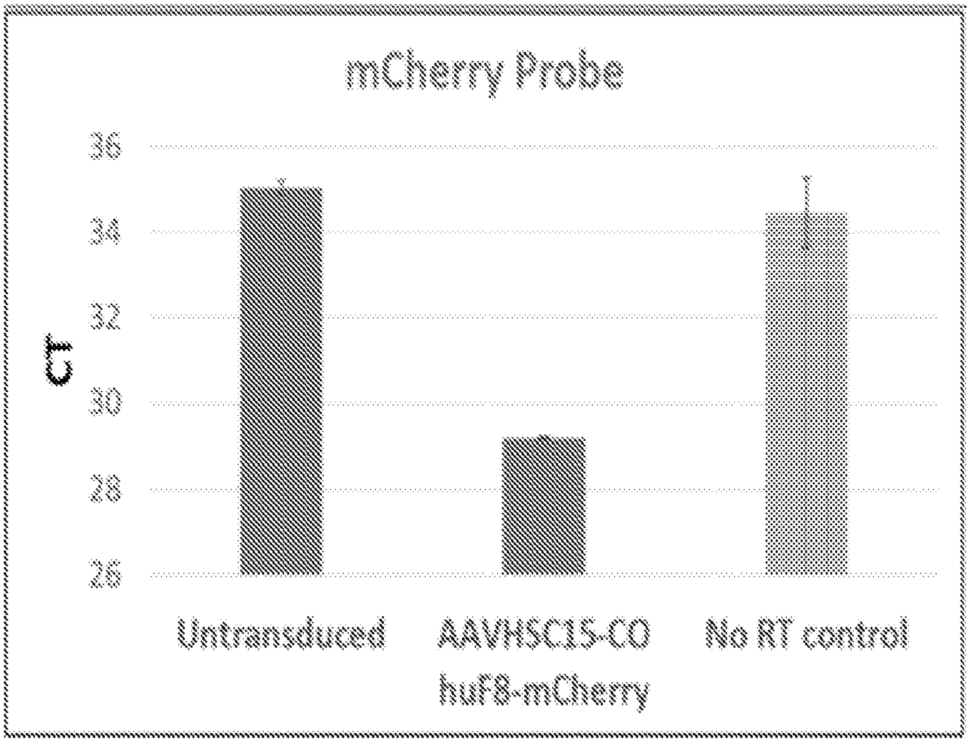
Figure 8:
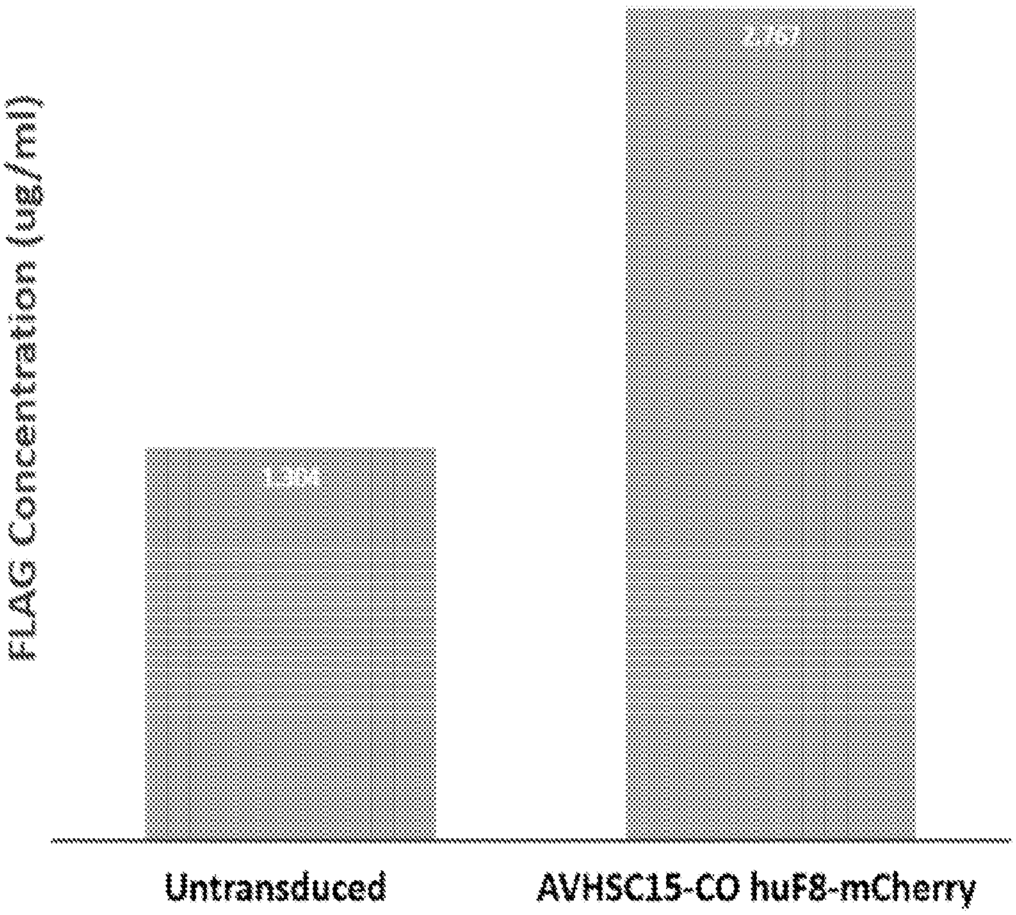
FIG. 8 illustrates expression of the secreted FLAG-tagged FVIII protein by AAVHSC15-edited primary human LSEC. As presented, primary human LSEC were transduced with the AAVHSC15-FVIII correction vector and FLAG tag was detected in the tissue culture supernatant after 48 hour culture in serum-free media. The results confirm that edited LSEC expressed the FLAG tagged protein from integrated FVII correction sequences driven by the chromosomal FVII promoters.
Figure 9:
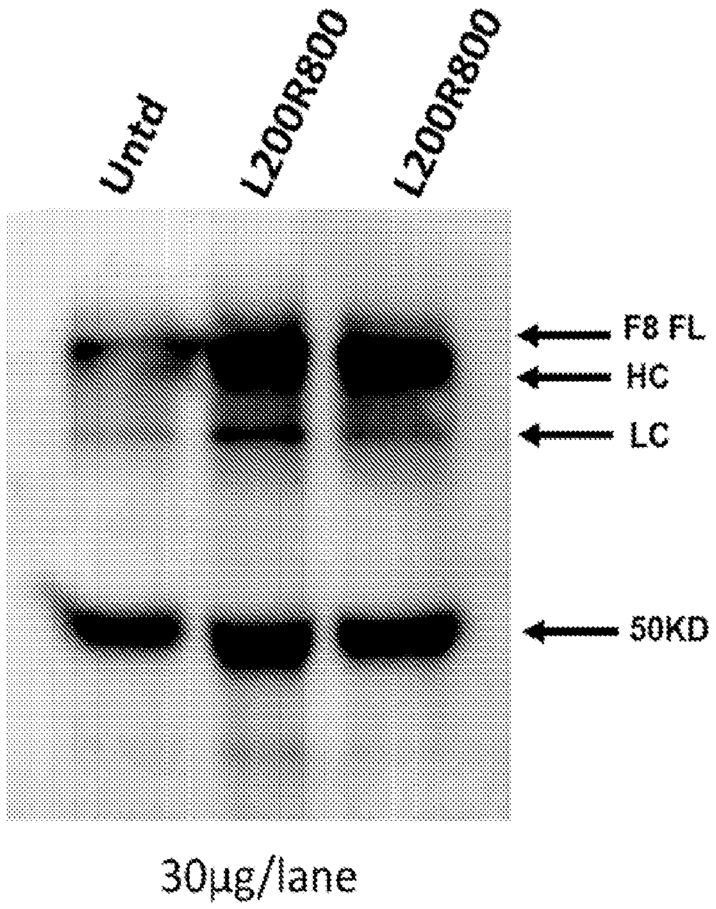
FIG. 9 illustrates the expression of FVII protein by primary human LSEC. As presented, serum-free tissue culture supernatant from LSEC was collected, concentrated and analyzed by Western blot analyses. Both untransduced and transduced LSEC expressed the FVIII protein. Edited LSEC showed expression of full length FVIII (F8 FL), FVIII heavy chains (HC) and FVIII light chains (LC).
Figure 10:
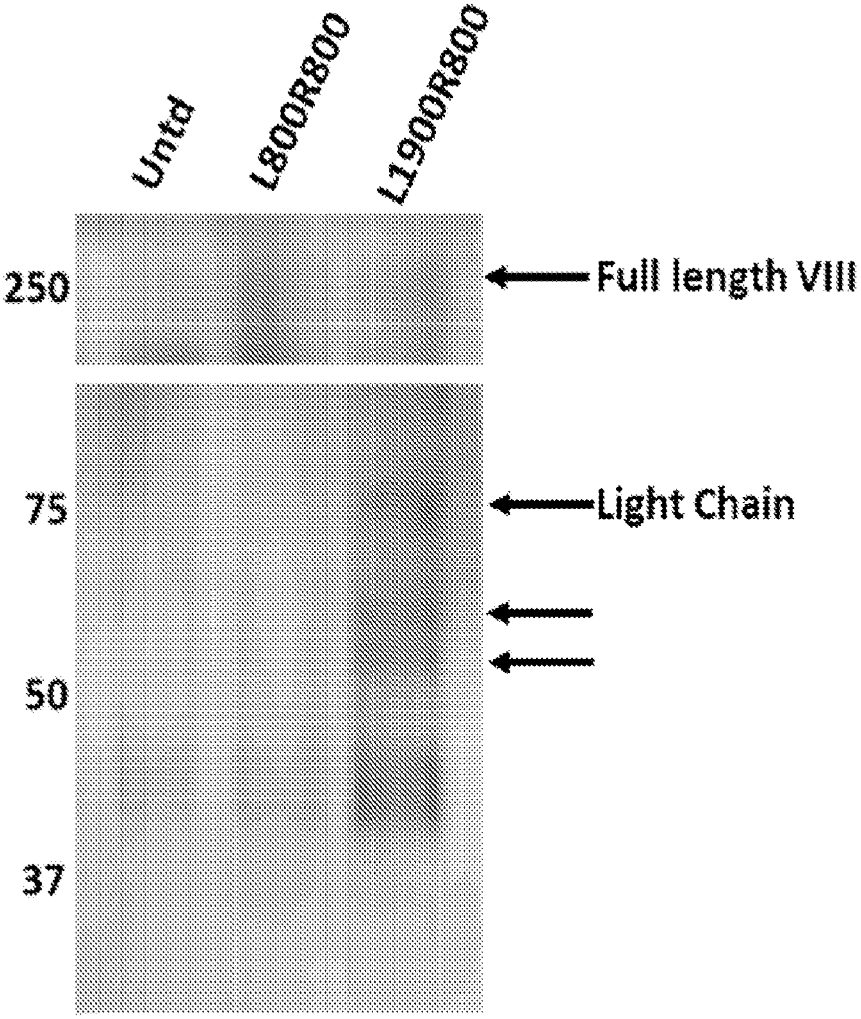
FIG. 10 illustrates the detection of FLAG-Tagged FVIII protein expression by primary human LSEC transduced with AAVHSC15 FVIII correction vectors. As presented, serum-free culture supernatants from AAVHSC15 transduced and untransduced human LSECs were immunoprecipitated with a cocktail of monoclonal anti-FVIII antibodies. Western blots were probed with an anti-FLAG antibody (following SDS-PAGE and transfer). Supernatant from untransduced LSEC served as negative controls. The full length FVIII protein (250 kD) and FLAG-associated FVIII peptides were detected specifically in the supernatants from edited cells. The results indicated that edited primary LSEC expressed recombinant FVIII from the edited locus based on detection of FLAG-tagged FVIII protein.
Figure 11:
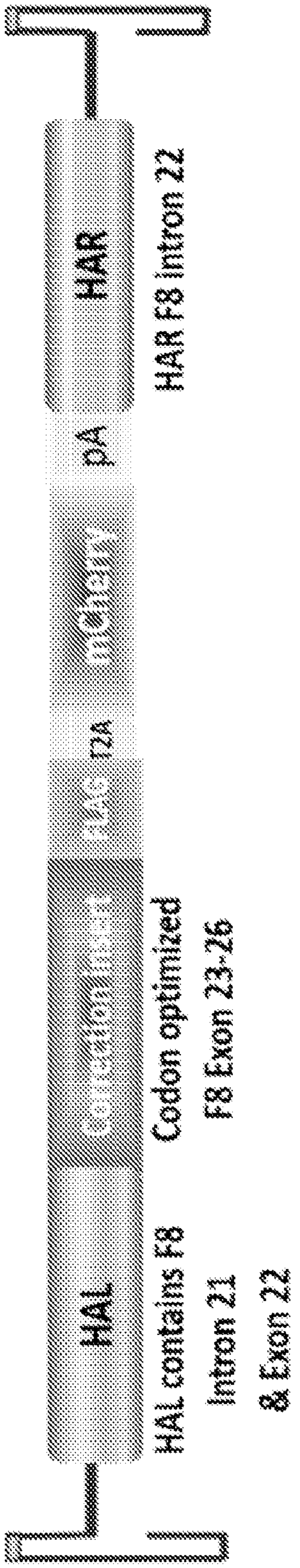
FIG. 11 illustrates the canine I22I FVIII correction vector. The correction vector was designed to insert the codon optimized cDNA of Exons 23-26 at the end of Exon 22 of the canine (K9) F8 gene. The homology arms in the canine correction vectors were 800 bp in length. A 3×FLAG tag was added to the 3' end of the Exon 26 of the correction sequence. The vector also encoded the mCherry coding region following a T2A sequence to allow independent translation. As presented, the editing vector was packaged in AAVHSC15.
Figure 12A:
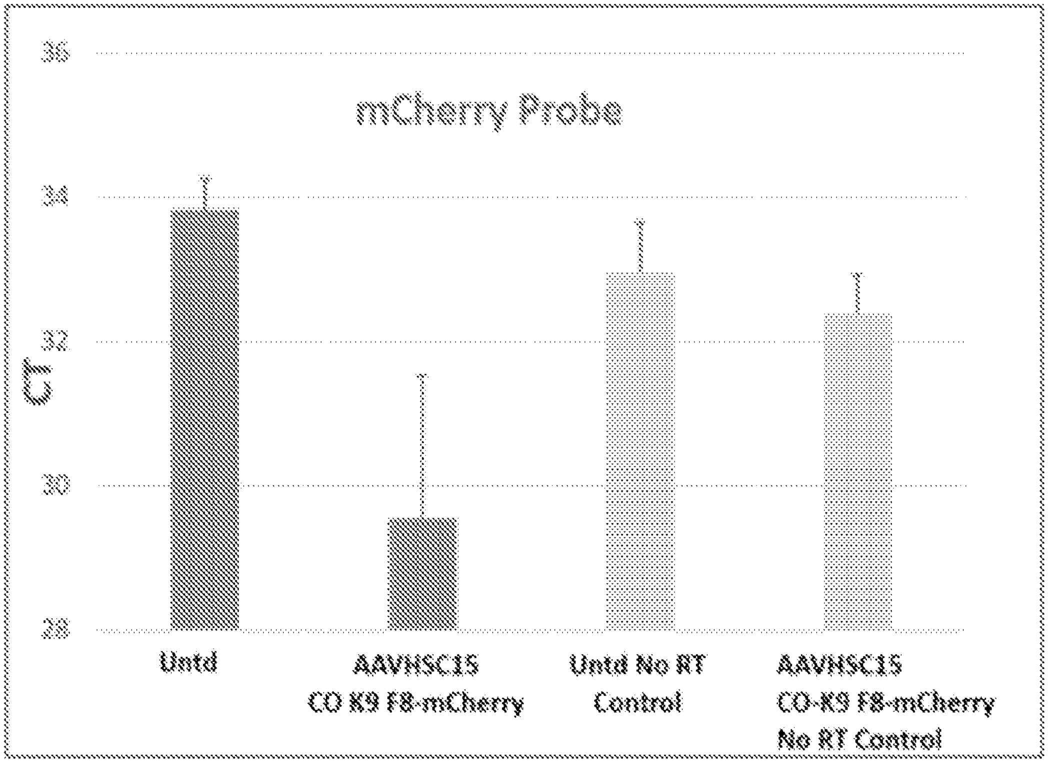
FIG. 12A-12B illustrate transcription expression results from the mCherry probe (12A) and the codon optimized canine FVIII probe (12B). As presented, AAVHSC15-edited primary canine LSEC expressed both mCherry and codon-optimized canine FVIII, where a lower CT signifies expression. Controls without reverse transcriptase were included as specificity controls. The data as presented in the figures illustrated successful targeted insertion and transcription of the correction transgene into the canine F8 gene in primary canine cells.
Figure 12B:
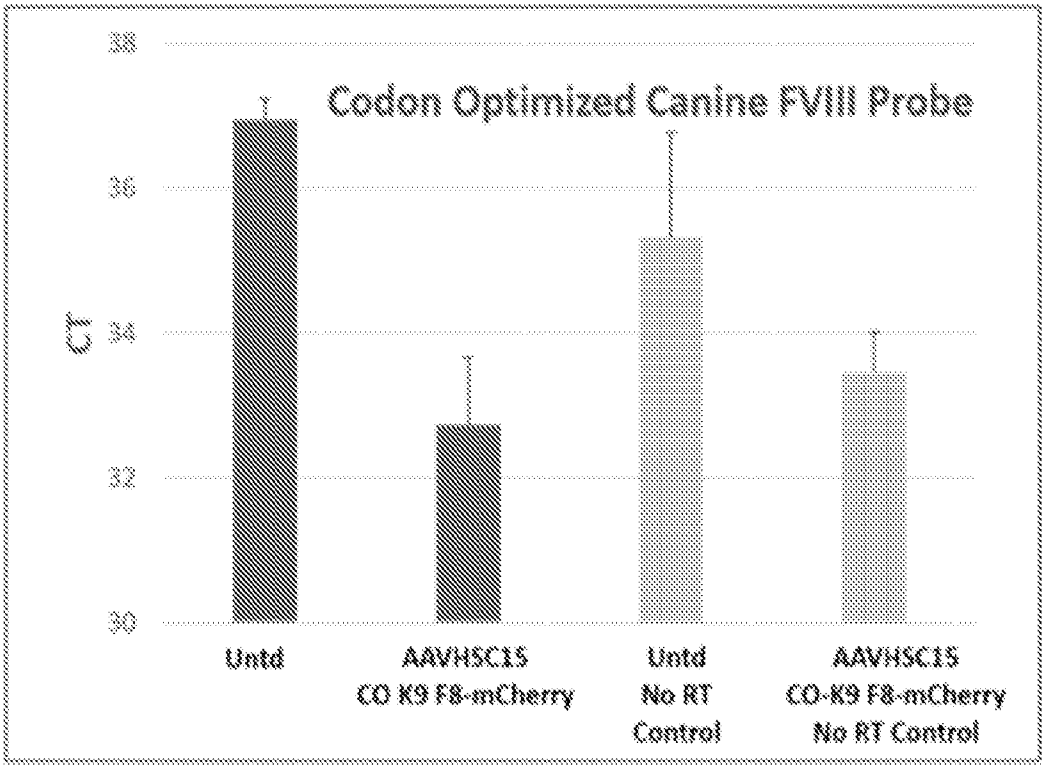
Figure 13:
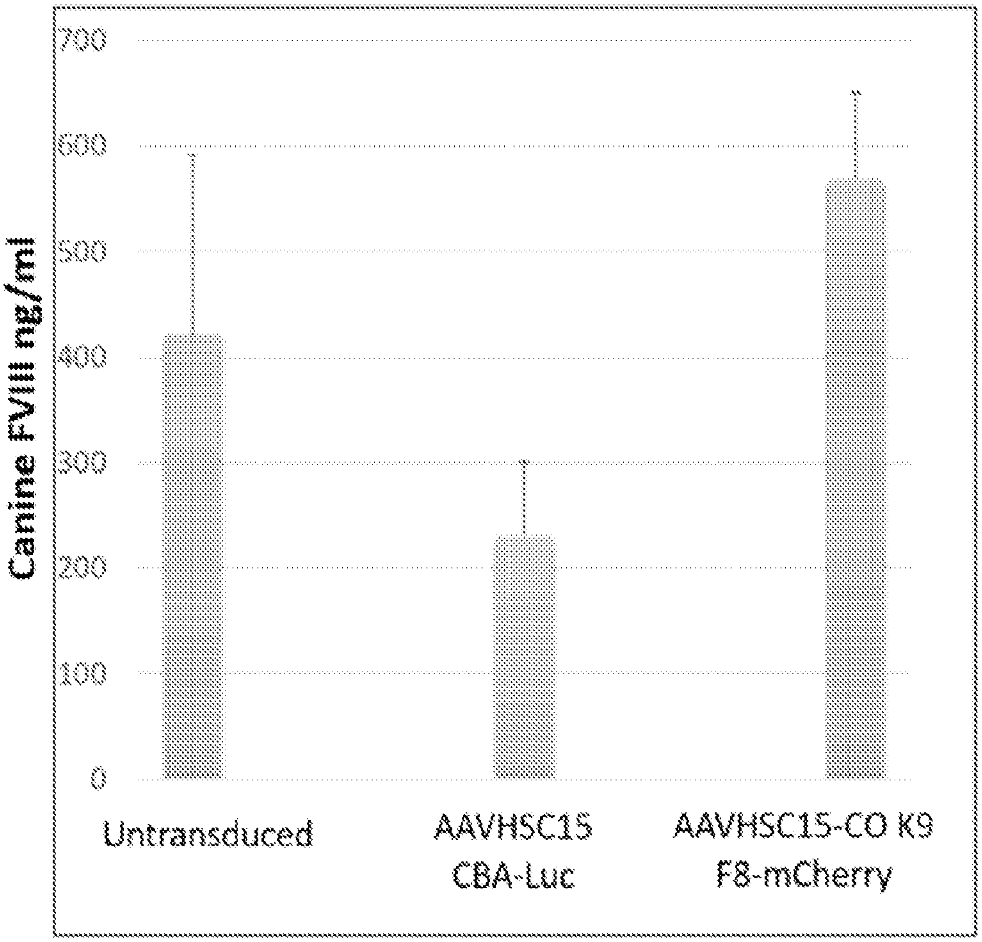
FIG. 13 illustrates canine FVIII detection by ELISA in the supernatant of AAVHSC15 transduced and control canine primary LSEC. Primary canine LSEC were transduced with the AAVHSC15-FVIII correction vector. FVIII was detected in the tissue culture supernatant after 48 hour culture in serum-free media. As presented, the data confirmed that primary canine LSEC transduced with the AAVHSC15 F8 correction vector expressed the FVIII protein under the control of the endogenous promoter.
Figure 14:
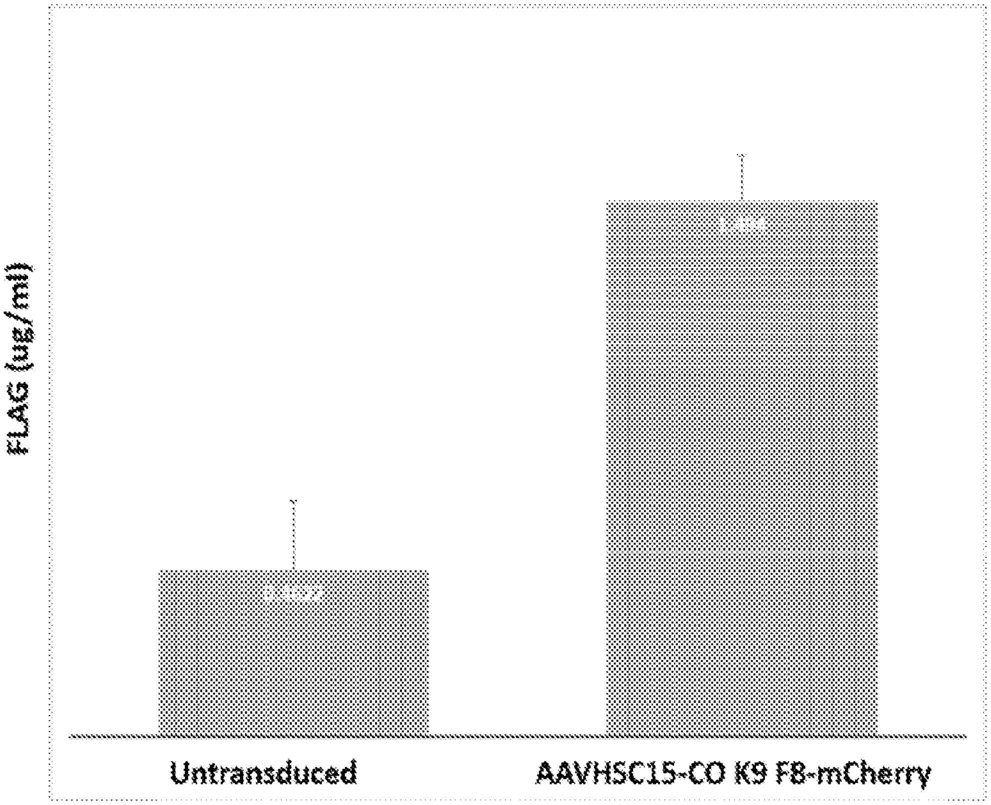
FIG. 14 illustrates FLAG-tagged FVIII expression by primary canine hepatocytes transduced with a AAVHSC15 canine FVIII I22 correction vector. Canine hepatocytes transduced with the AAVHSC15 FVIII I22 correction vector expressed the FLAG tag from the inserted correction sequence driven by the chromosomal FVIII promoter. The FLAG tag was fused to the correction sequence. As presented, the data confirmed that expression of the recombinant FVIII protein from the edited FVIII locus in primary canine hepatocytes via detection of the FLAG tag in the culture supernatant.
Figure 15:
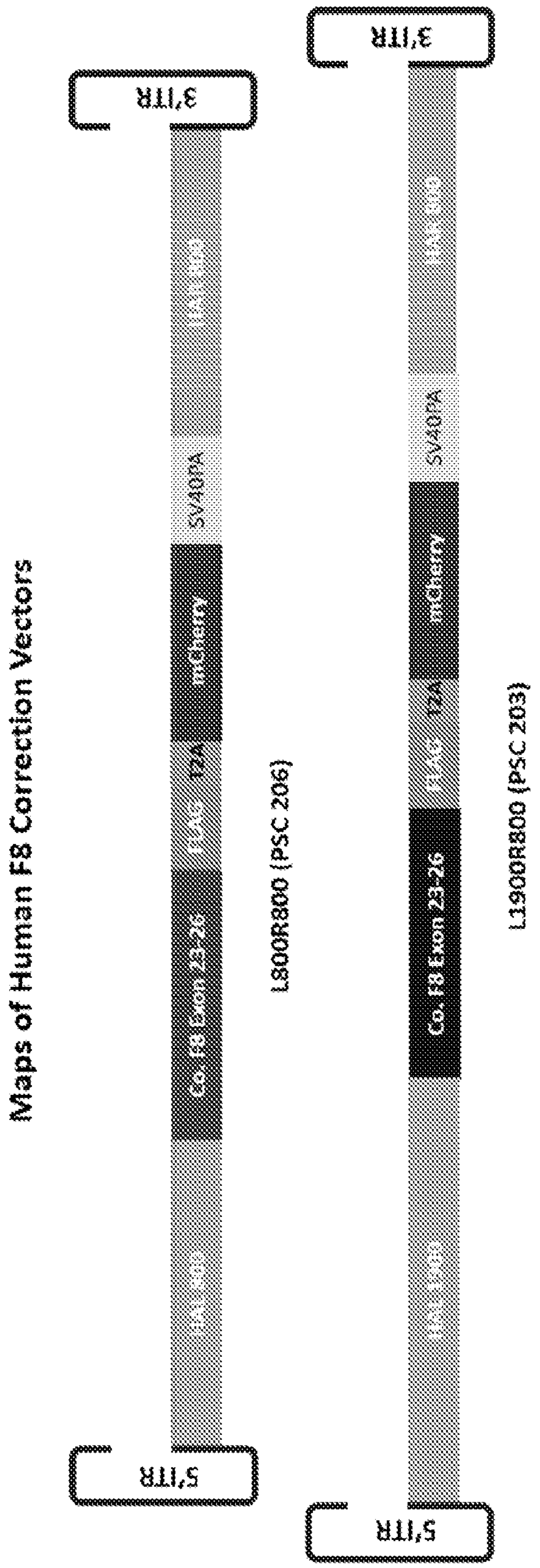

FIG. 15 illustrates maps of correction vectors. Correction vectors were designed to insert the codon optimized cDNA of exons 23-26 at the end of exon 22 of the F8 gene. The F8 editing vectors consist of 1. AAV2 ITRs; 2. Left and right homology arms; 3. A codon optimized cDNA of F8 exon 23 to exon26; 4. A FLAG tag immediately downstream of the cDNA; 4. A promoterless expression cassette consisting of a T2A sequence the mCherry open reading frame and a polyadenylation signal. Left homology arm is composed of the F8 Exon22 and part of the F8 intron 21 with either 800 bases (L800) or 1900 bases (L1900). For both vectors, Right homology arm is 800 bases of F8 intron 22.

Figure 16:
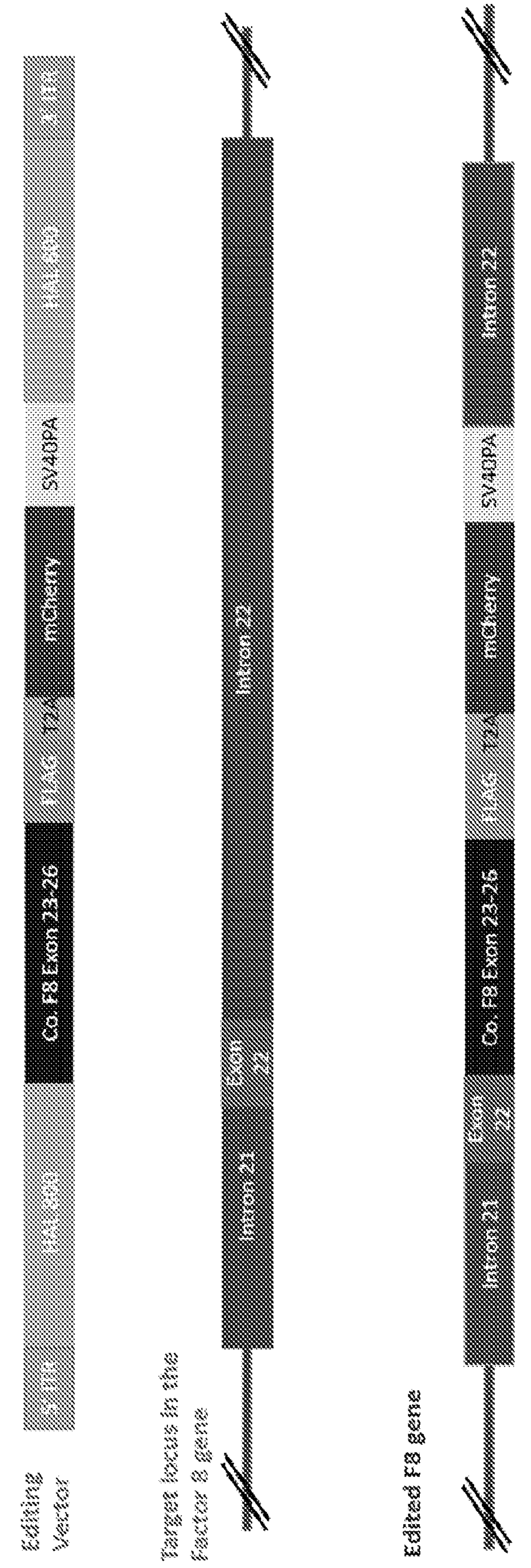

FIG. 16 illustrates schematics of the editing vector, the target location with the I22I inverted F8 gene and the edited I22I target locus.

Figure 17A:
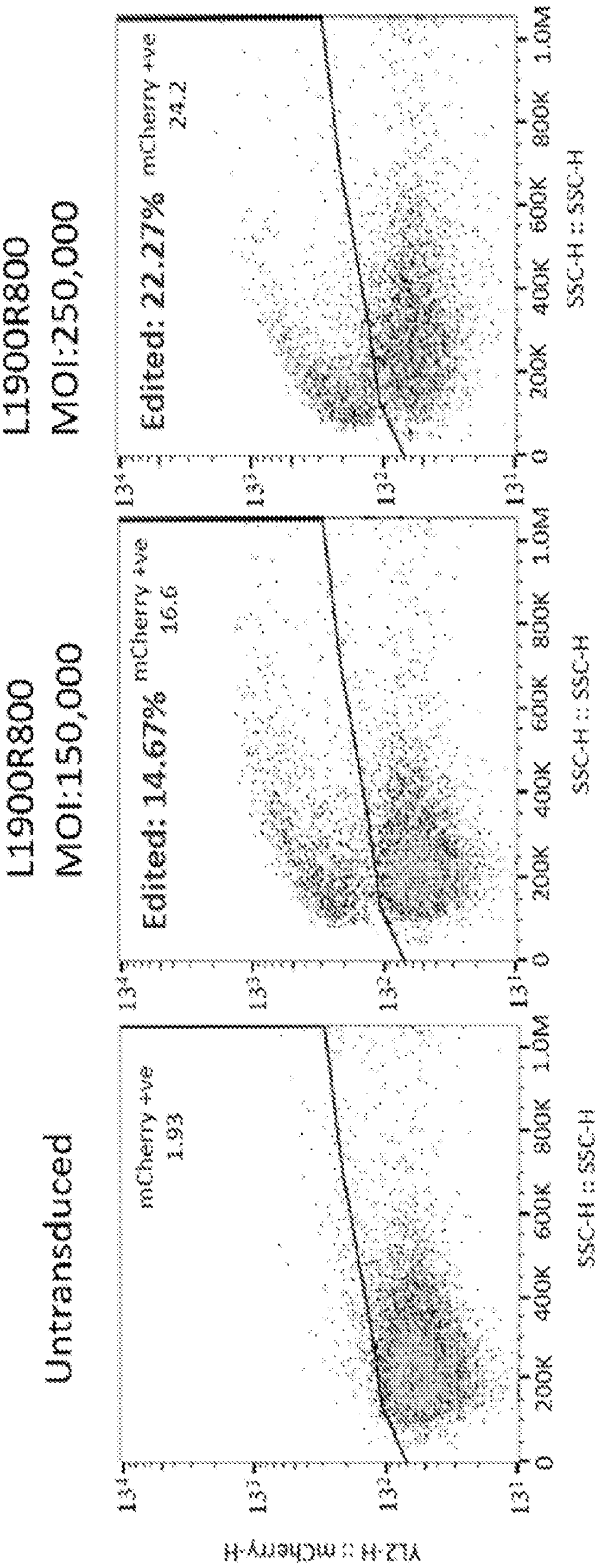
Figure 17B:
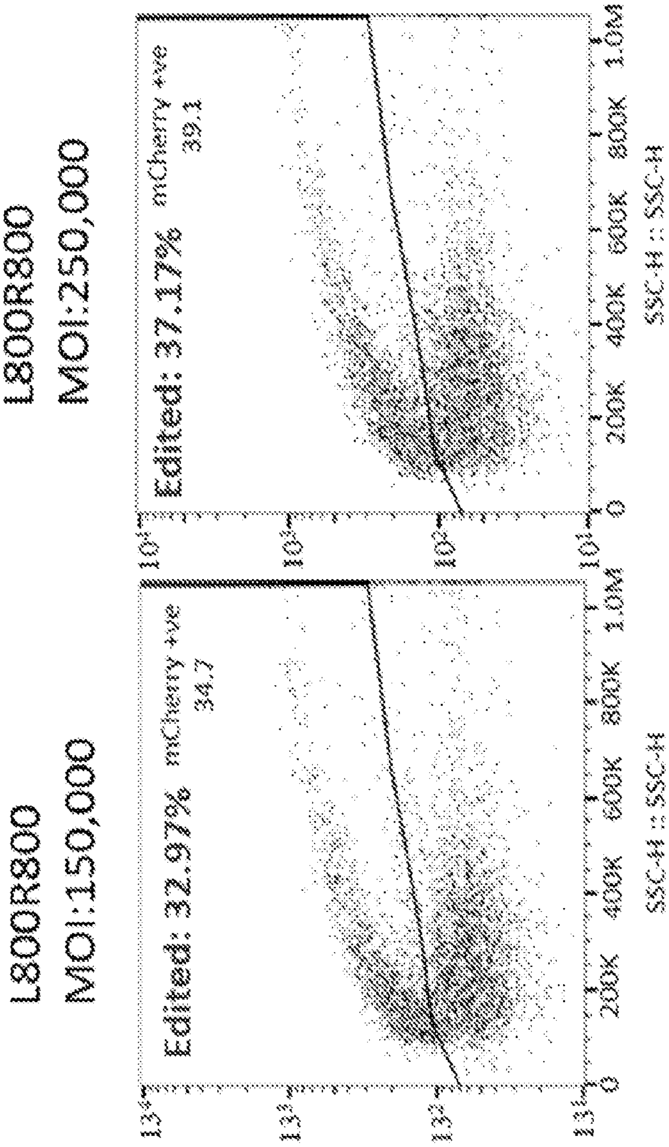

FIG. 17 illustrates mCherry expression in AAVHSC15 edited B LCLs from an I22I hemophilia A patient. B-LCLs were transduced with AAVHSC-F8 editing vectors containing left HA of either 1900 or 800 bp. Transductions were performed at MOI: 150,000 or 250,000. Cells were analyzed by flow cytometry 48 hours post-transduction. Editing efficiency as indicated by mCherry expression is shown after background subtraction.

Figure 18:
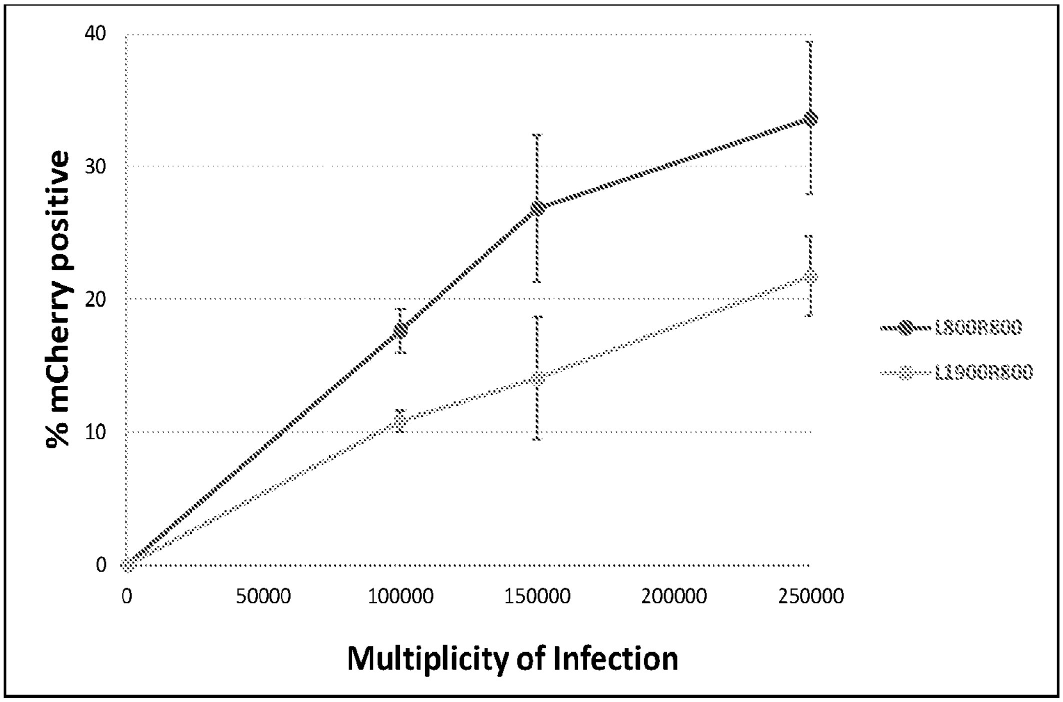

FIG. 18 illustrates dose response of editing of the F8 Gene in I22I B-LCLs with the AAVHSC15 L800R800 and L1900R800 editing vectors. I22I cells were transduced at MOI: 100,000, 150,000 and 250,000.

Figure 19A:
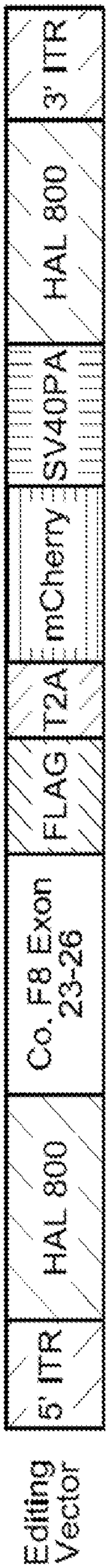
Figure 19B:
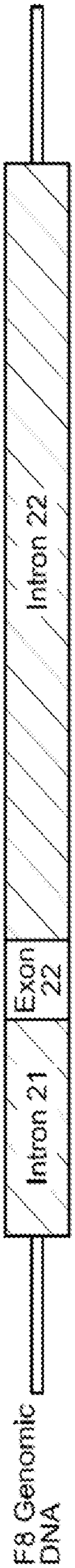
Figure 19C:
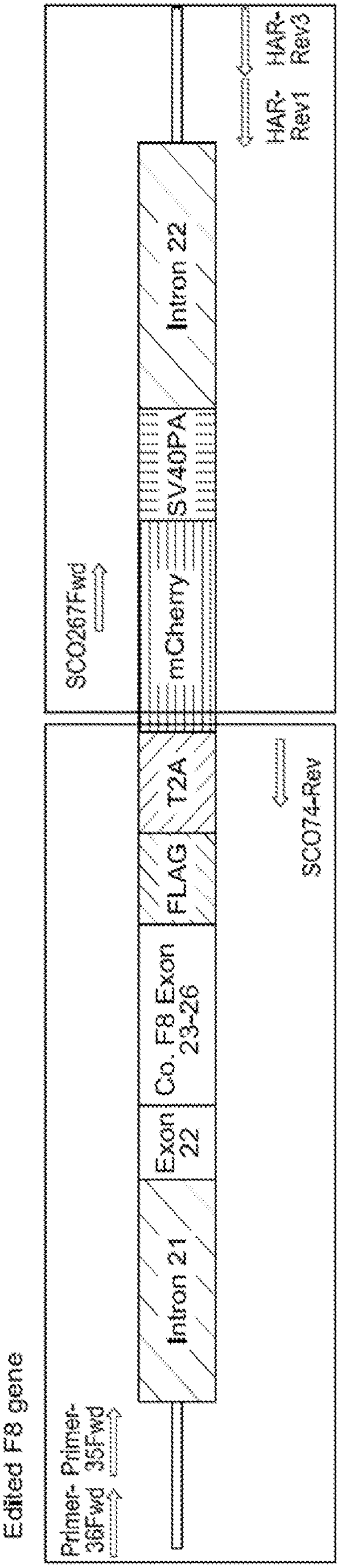

FIGS. 19A-19C illustrate schematic maps. 19A is a map of the editing vector with FLAG tagged codon optimized exon 23 to exon 26 and reporter cassette. 19B is a map of the Factor 8 genomic locus showing the end of exon 272. 19C is a map of the edited targeted locus at the end of F8 exon 22. Also shown are the locations of the primers used for amplification of the 5' and 3' junctions in the targeted Integration (TI) assay.

Figure 20A:
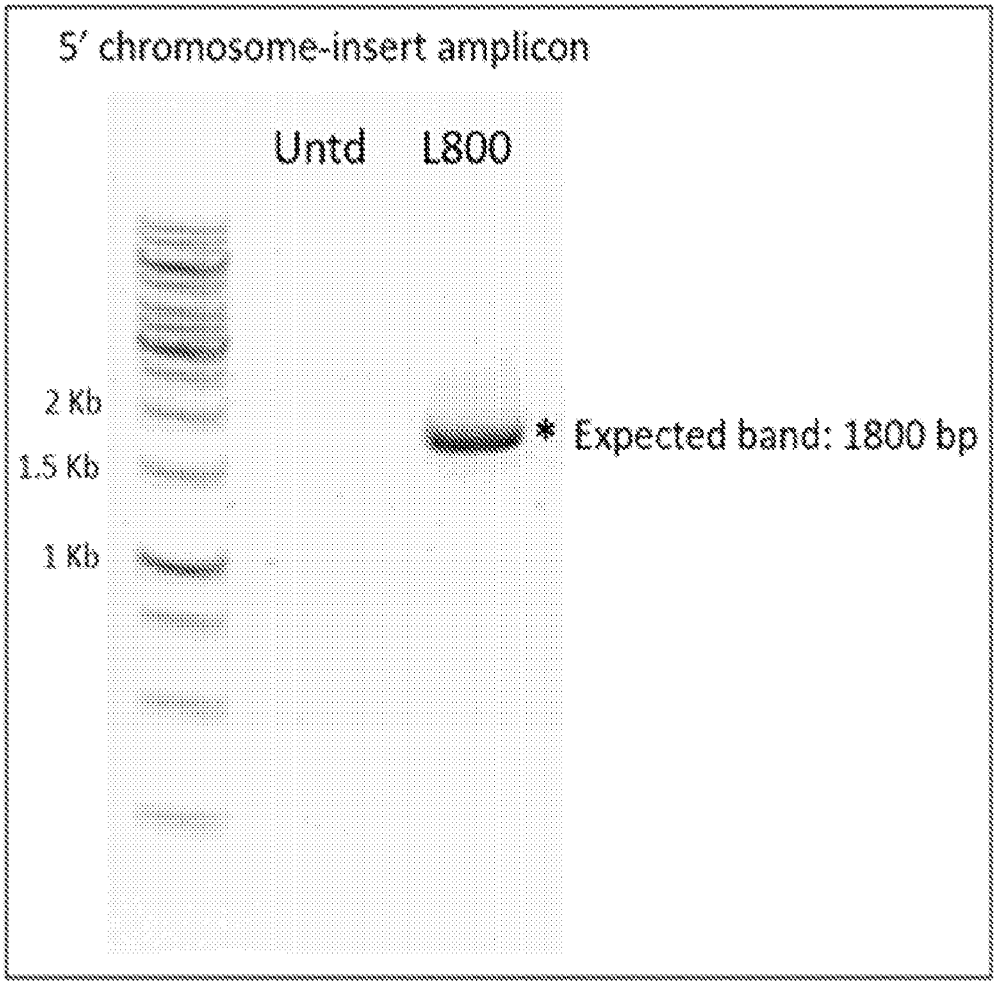
Figure 20B:
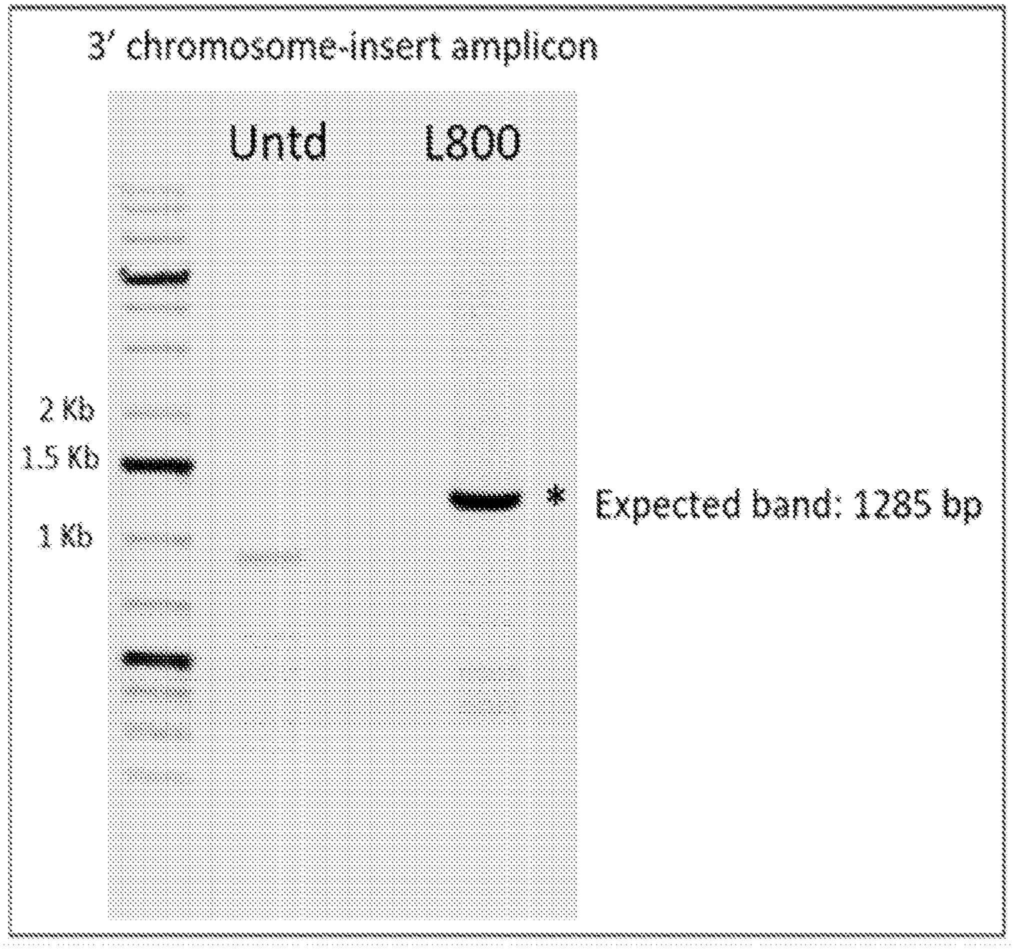

FIGS. 20A-20B illustrate targeted integration assays were performed using 200000 cells with the AAVHSC15 L800R800 editing vector at MOI: 150,000. Genomic DNA was isolated after 48 hours. TI amplicon was amplified using an insert-specific primer and a chromosome-specific primer that hybridized outside the homology arms. Untransduced LSEC genomic DNA was used as control. The expected bands were only observed in transduced but not in untransduced cells.

Figure 21:
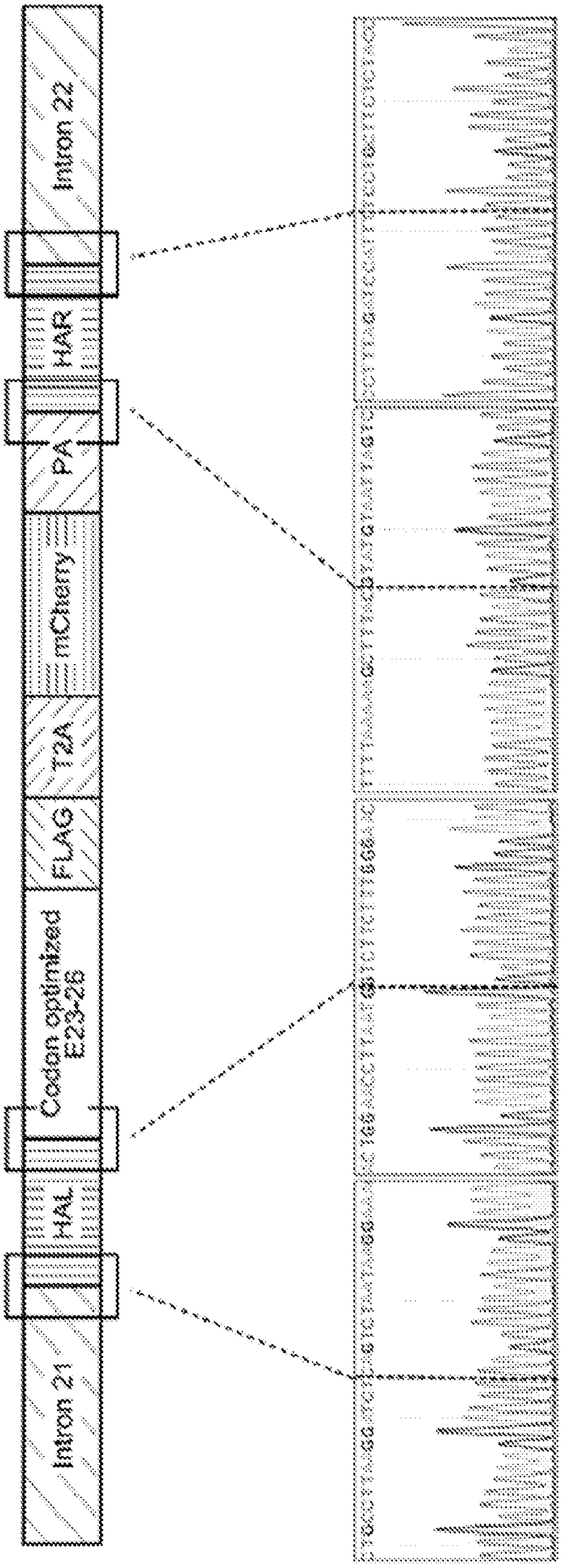

FIG. 21 illustrates Sanger sequencing of the edited TI amplicon. Sequences are shown across the chromosome-HA junctions and insert-HA junction. Results revealed seamless insertion of codon optimized exon 23-26cDNA with 3' FLAG tag and promoterless reporter cassette. No insertion/deletion mutations or AAV ITRs were detected.

FIGS. 22A-22B illustrate targeted integration assays to evaluate editing of I22I inverted B-LCL cells. I22I B-LCLs were transduced with the AAVHSC15 L800R800 editing vector at MOI:150,000. Junction regions were amplified using an insert-specific primer and a chromosome-specific primer. Untransduced I22I BLCL cell served as a control. Expected bands were only observed in transduced I22I cells, but not in untransduced cells.

Figure 23A:
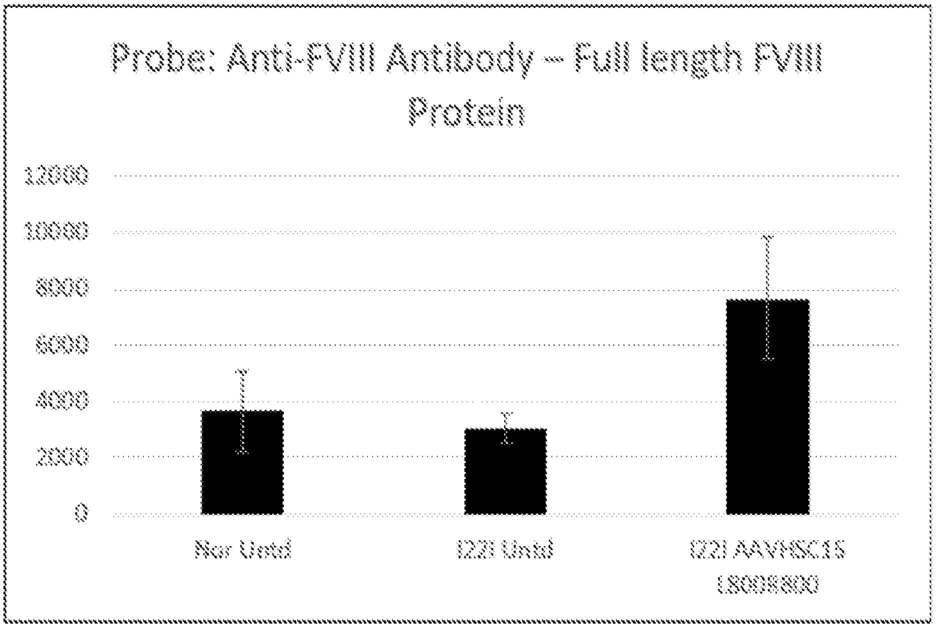
Figure 23B:
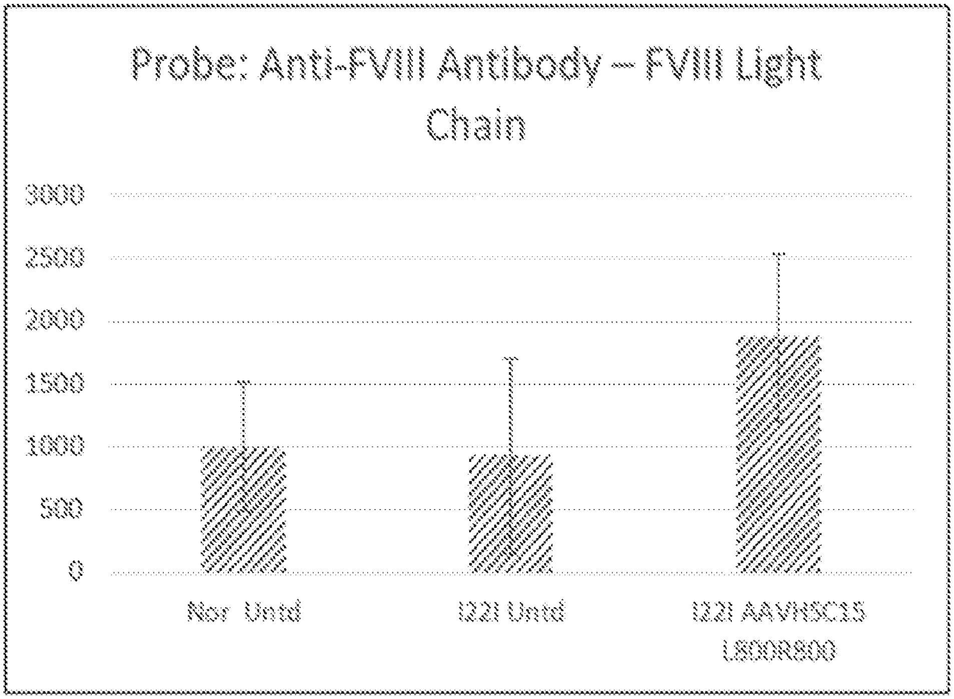

FIGS. 23A-23B illustrate Western blot analyses of Factor FVIII expression. Lysates from AAVHSC15 L800R800 transduced and untransduced I22I B-LCLs and wild type Nor cells were resolved by electrophoresis and probed with an anti-FVIII antibody. Full length FVIII and the FVIII Light Chain band density were measured by ImageJ software and plotted.

Figure 24A:
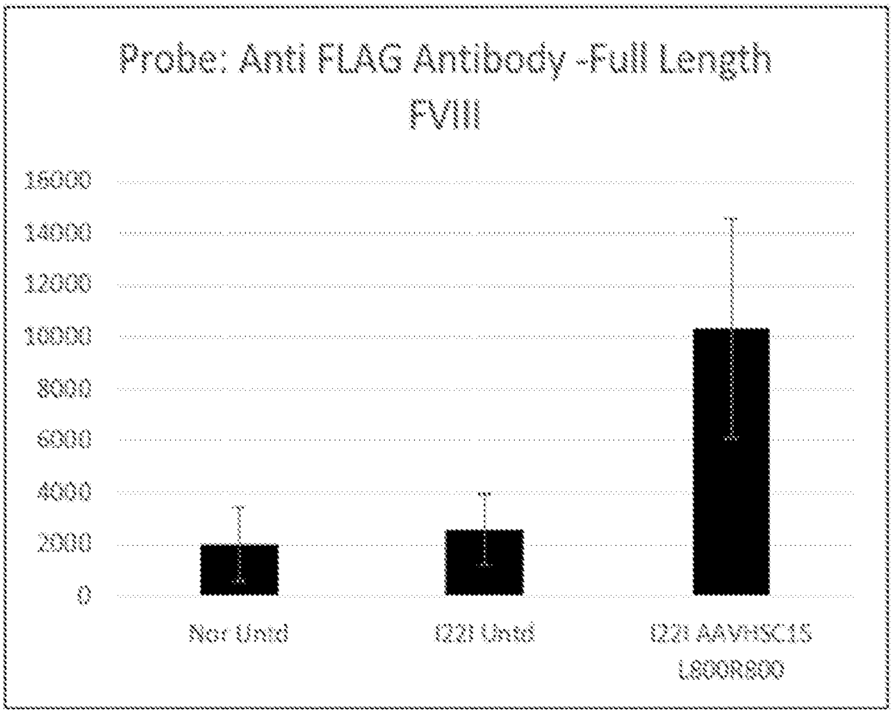
Figure 24B:
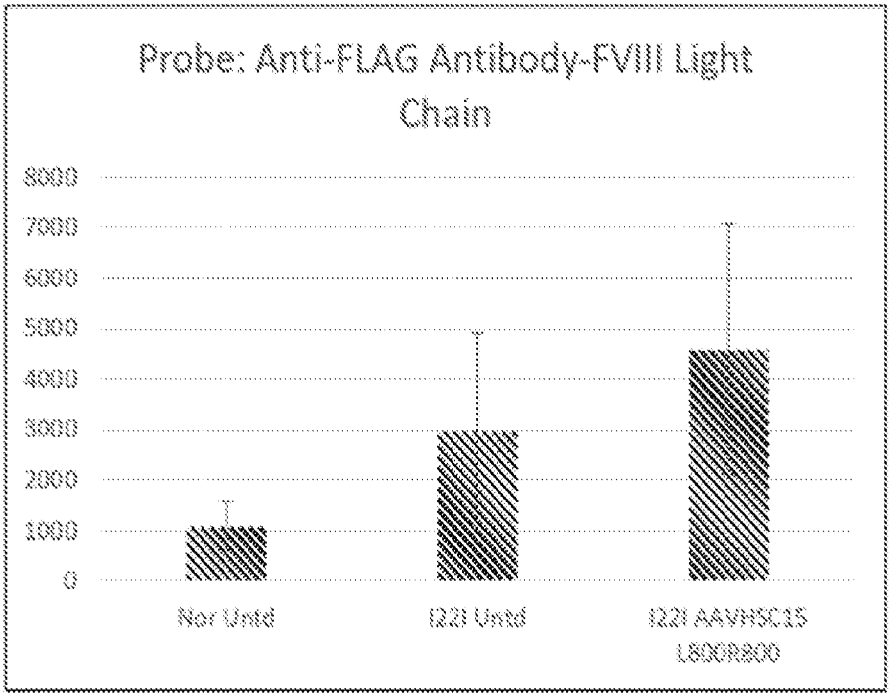

FIGS. 24A-24B illustrate Western blot analyses of Factor FVIII expression. Lysates from AAVHSC15 L800R800 transduced and untransduced I22I B-LCLs and wild type Nor cells were resolved by gel electrophoresis and probed with an anti-FLAG antibody. Full length FVIII and the FVIII Light Chain band density were measured by ImageJ software and plotted.

Figure 25A:
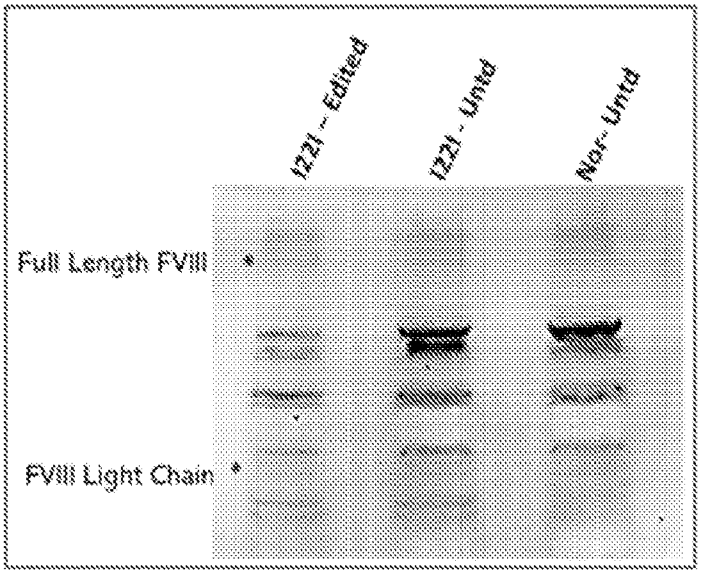
Figure 25B:
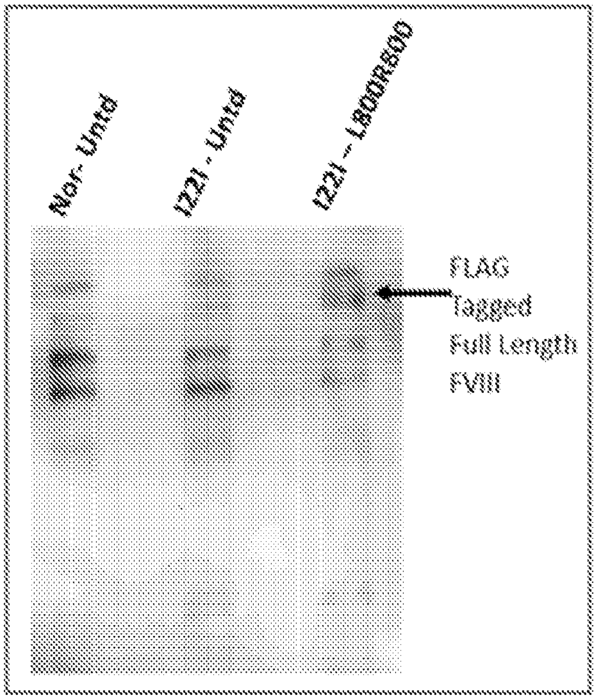
Figure 25C:
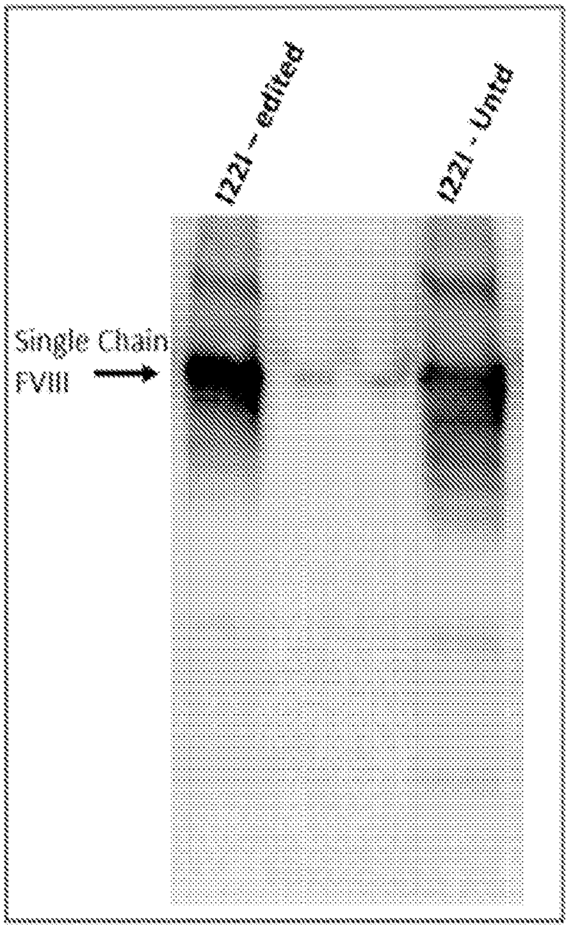

FIGS. 25A-25C illustrate expression of FVIII protein from AAVHSC15 L800R800 edited patient derived I22I B-LCLs. 25A. Western blot analysis of lysates from AAVHSC15 L800R800 transduced and untransduced I22I B-LCLs and wild type Nor B-LCLs. Blot was probed with an anti-FVIII antibody. The full length FVIII and the FVIII light chain are visible. 25B. Western blot analysis of lysates from AAVHSC15 L800R800 transduced and untransduced I22I B-LCLs and wild type Nor B-LCLs. Blot was probed with an anti-FLAG antibody. The FLAG tagged full length FVIII protein is visible. 25C. I22I inverted patient B-LCLs were transduced with the AAVHSC15 L800R800 editing vector at MOI: 250,000. Cell lysates were immunoprecipitated using a cocktail of anti-FVIII antibodies followed by immunoblotting using a FVIII-specific monoclonal antibody. The single chain FVIII band in I22I cells edited with AAVHSC-F8 L800R800 showing expression levels higher than untransduced I22I cells. Nor-Untd-normal BLCL, untransduced; I22I-Untd-I22I BLCL, untransduced; I22I-Edited-I22I BLCL transduced with AAVHSCF8 L800R800.

Figure 26:
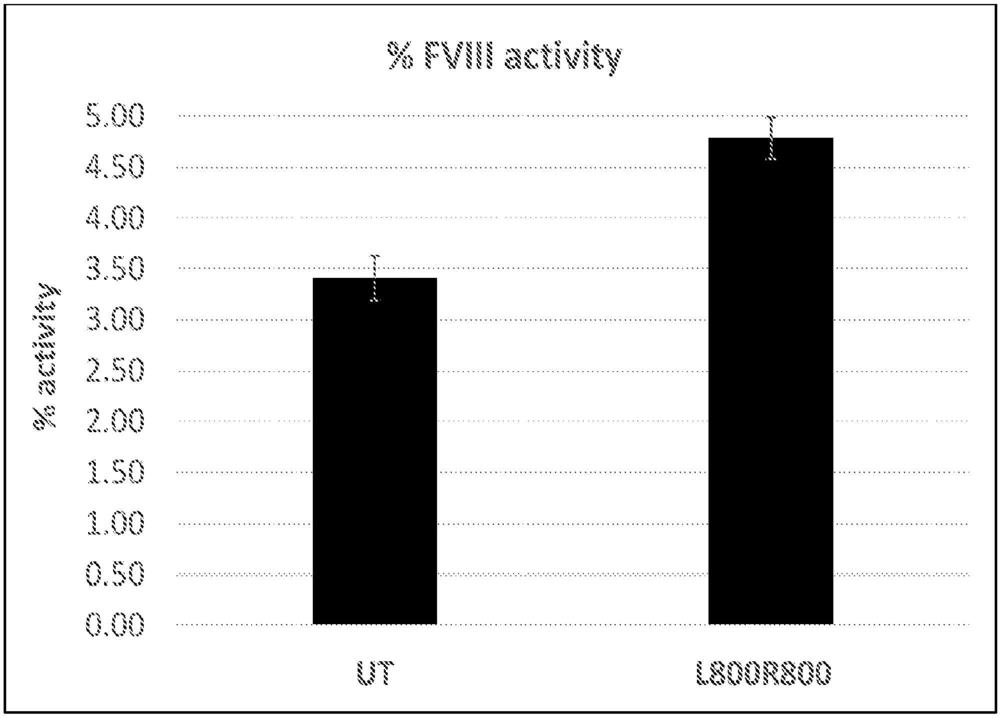

FIG. 26 illustrates functional activity of the edited FVIII protein. A chromogenic Coatest assay was used to evaluate the activity of the edited FVIII protein in AAVHSC15 L800R800 transduced and untransduced (UT) LSEC. Lysates from transduced cells demonstrated functionally active FVIII protein.

DETAILED DESCRIPTION

Before the present invention is further described, it is to be understood that this invention is not strictly limited to particular embodiments described, as such may of course vary. It is also to be understood that the terminology used herein is for the purpose of describing particular embodiments only, and is not intended to be limiting, since the scope of the present invention will be limited only by the claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

It is further noted that the claims may be drafted to exclude any optional element.

As such, this statement is intended to serve as antecedent basis for use of such exclusive terminology as "solely," "only" and the like in connection with the recitation of claim elements, or use of a "negative" limitation.

I. Definitions

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about means the specified value.

A "chemical linker," as provided herein, is a covalent linker. In embodiments, the chemical linker is a bond, —O—, —S—, —C(O)—, —C(O)O—, —C(O)NH—, —$S(O)_2$NH—, —NH—, —NHC(O)NH—, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof.

The chemical linker as provided herein may be a bond, —O—, —S—, —C(O)—, —C(O)O—, —C(O)NH—, —$S(O)_2$NH—, —NH—, —NHC(O)NH—, substituted or unsubstituted (e.g., $C_1$-$C_{20}$, $C_1$-$C_{10}$, $C_1$-$C_5$) alkylene, substituted or unsubstituted (e.g., 2 to 20 membered, 2 to 10 membered, 2 to 5 membered) heteroalkylene, substituted or unsubstituted (e.g., $C_3$-$C_8$, $C_3$-$C_6$, $C_3$-$C_5$) cycloalkylene, substituted or unsubstituted (e.g., 3 to 8 membered, 3 to 6 membered, 3 to 5 membered) heterocycloalkylene, substituted or unsubstituted (e.g., $C_6$-$C_{10}$, $C_6$-$C_8$, $C_6$-$C_5$) arylene or substituted or unsubstituted (e.g., 5 to 10 membered, 5 to 8 membered, 5 to 6 membered,) heteroarylene.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may In embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In aspects, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

The term "complementary" or "complementarity" refers to the ability of a nucleic acid to form hydrogen bond(s) with another nucleic acid sequence by either traditional Watson-Crick or other non-traditional types. For example, the sequence A-G-T is complementary to the sequence T-C-A. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions (i.e., stringent hybridization conditions)

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., sgRNA) may be detected by standard PCR or Northern blot methods well known in the art. See, Sambrook et al., 1989 Molecular Cloning: A Laboratory Manual, 18.1-18.88.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the amino acid side chain is H

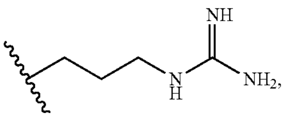
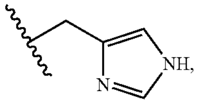
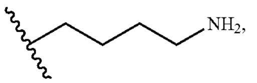
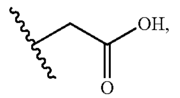
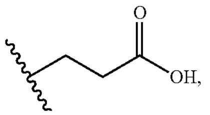
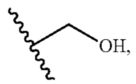
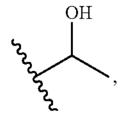
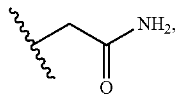
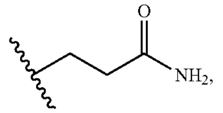
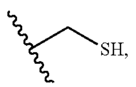
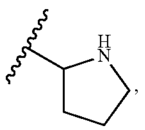
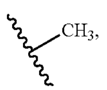
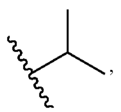
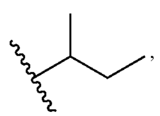
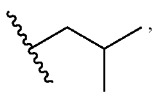

-continued

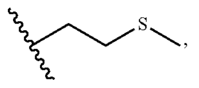
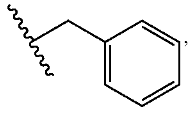
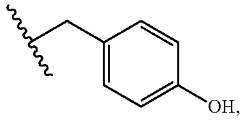
or
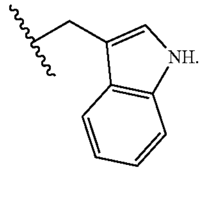

The term "non-natural amino acid side chain" refers to the functional substituent of compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples include exo-cis-3-Aminobicyclo[2.2.1]hept-5-ene-2-carboxylic acid hydrochloride, cis-2-Aminocycloheptanecarboxylic acid hydrochloride,cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-p-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe (4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl] acetic acid purum, Boc-β-(2-quinolyl)-Ala-OH, N-Boc-1,2,3,6-tetrahydro-2-pyridinecarboxylic acid, Boc-j-(4-thiazolyl)-Ala-OH, Boc-3-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-3-(4-thiazolyl)-Ala-OH, Fmoc-R-(2-thienyl)-Ala-OH, 4-(Hydroxymethyl)-D-phenylalanine.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components/

As used herein, the term "replication-defective adeno-associated virus" refers to an AAV comprising a genome lacking Rep and Cap genes.

As used herein, the term "F8 gene" refers to a wild-type or mutant gene encoding the FVIII protein, including but not limited to the coding regions, exons, introns, 5' UTR, 3' UTR, and transcriptional regulatory regions of the F8 gene. The human F8 gene is identified by Entrez Gene ID 2157. Wild-type human F8 gene is identified by nucleotides 5,001 to 191,936 of NCBI Reference Sequence: NG_011403.1. An exemplary nucleotide sequence of a full-length human F8 cDNA is identified by NCBI Reference No.: NM_000132.3. An exemplary amino acid sequence of a full-length human FVIII polypeptide, including its 19-amino acid signal peptide, is identified by NCBI Reference No.: NP_000123.1. Intron 22 of human F8 corresponds to nucleotides 131,648-164,496 (32,849 nt) of NCBI Reference Sequence: NG_011403.1.

As used herein, the term "homology arms" can be directed to any region of the F8 gene or a gene nearby on the genome. In embodiments, the correction genome comprises homology arms. In embodiments, the exact identity and positioning of the homology arms are determined by the identity of the editing element and/or the target locus. In embodiments, the homology arms comprise one or more genetic variations in the human population. In embodiments, the homology arms comprise one or more modifications (e.g., nucleotide substitutions, insertions, or deletions) designed to improve expression level or specificity. In embodiments, the homology arms comprise one or more genetic variations and optionally one more modification designed to improve expression level or specificity in the human population. In embodiments, human genetic variations may include both inherited variations and de novo variations that are particular to the target genome, and encompass insertions, deletions, simple nucleotide polymorphisms, inversions, rearrangements, inversions, micro-repeats, and combinations thereof.

As used herein, the term "correcting a mutation in an F8 gene" refers to the insertion, deletion, or substitution of one or more nucleotides at a target locus in a mutant F8 gene to create an F8 gene that is capable of expressing a wild-type FVIII polypeptide or a functional equivalent thereof. In certain embodiments, "correcting a mutation in an F8 gene" involves inserting a nucleotide sequence encoding at least a portion of a wild-type FVIII polypeptide or a functional equivalent thereof into the mutant F8 gene, such that a wild-type FVIII polypeptide or a functional equivalent thereof is expressed from the mutant F8 gene locus (e.g., under the control of an endogenous F8 gene promoter). A skilled person in the art will appreciate that the portion of a correction genome comprising the 5' homology arm, editing element, and 3' homology arm can be in the sense or antisense orientation relative to the target locus (e.g., the human F8 gene).

As used herein, the term "correction genome" refers to a recombinant AAV genome that is capable of integrating an editing element (e.g., one or more nucleotides or an internucleotide bond) via homologous recombination into a target locus to correct a genetic defect in an F8 gene. In certain embodiments, the target locus is in the human F8 gene. The skilled artisan will appreciate that the portion of a correction genome comprising the 5' homology arm, editing element, and 3' homology arm can be in the sense or antisense orientation relative to the target locus (e.g., the human F8 gene).

As used herein, the term "editing element" refers to the portion of a correction genome that when integrated at a target locus modifies the target locus. An editing element can mediate insertion, deletion, or substitution of one or more nucleotides at the target locus.

As used herein, the term "target locus" refers to a region of a chromosome or an internucleotide bond (e.g., a region or an internucleotide bond of the human F8 gene) that is modified by an editing element.

As used herein, the term "a disease or disorder associated with an F8 gene mutation" refers to any disease or disorder caused by, exacerbated by, or genetically linked with mutation of an F8 gene. The F8 protein is an essential blood-clotting protein. In certain embodiments, the disease or disorder associated with an F8 gene mutation is hemophilia A.

As used herein, the term "coding sequence" refers to the portion of a complementary DNA (cDNA) that encodes a polypeptide, starting at the start codon and ending at the stop codon. A gene may have one or more coding sequences due to alternative splicing and/or alternative translation initiation. A coding sequence may either be wild-type or silently altered. An exemplary full-length wild-type F8 coding sequence is identified by nucleotides 172 to 7,227 of NCBI Reference No.: NM_000132.3. An exemplary portion of wild-type F8 coding sequence, corresponding to exons 22-26.

As used herein, the term "silently altered" or "silent alteration" refers to alteration of a coding sequence of a gene (e.g., by nucleotide substitution) without changing the amino acid sequence of the polypeptide encoded by the gene. In certain embodiments, silent alteration increases the expression level of a coding sequence. In certain embodiments, silent alteration reduces off-targeting to undesired genomic loci.

As used herein, the term "polyadenylation sequence" refers to a DNA sequence that when transcribed into RNA constitutes a polyadenylation signal sequence. The polyadenylation sequence can be native (e.g., from the F8 gene) or exogenous. The exogenous polyadenylation sequence can be a mammalian or a viral polyadenylation sequence (e.g., an SV40 polyadenylation sequence).

As used herein, the term "integration" refers to introduction of an editing element into a target locus of a target gene by homologous recombination between a correction genome and the target gene. Integration of an editing element can result in substitution, insertion and/or deletion of one or more nucleotides in a target gene. For example, in certain embodiments, the term "integration" refers to introduction of an editing element into a target locus of an F8 gene by homologous recombination between a correction genome and the F8 gene. Integration of an editing element can result in substitution, insertion and/or deletion of one or more nucleotides in an F8 gene.

As used herein, the term "integration efficiency of the editing element into the target locus" refers to the percentage of cells in a transduced population in which integration of the editing element into the target locus has occurred.

As used herein, the term "allelic frequency of integration of the editing element into the target locus" refers to the percentage of alleles in a population of transduced cells in which integration of the editing element into the target locus has occurred.

II. Compositions

As used herein, "AAV" refers to adeno-associated virus. In certain embodiments, the AAV disclosed herein comprise: an AAV capsid comprising an AAV capsid protein; and a correction genome for editing a target locus in an F8 gene. The AAV capsid proteins that can be used in the AAV compositions disclosed herein include without limitation AAV capsid proteins and derivatives thereof.

As used herein, the term "AAVHSC" refers to adeno-associated virus transduced hematopoietic stem cells. Specifically, provided herein are AAV vectors that transduced primitive CD34+ hematopoietic stem cells. In embodiments, the genome editing methods referred to herein are AAVHSC mediated. In embodiments, tropism of AAVHSCs was not restricted to HSCs. In embodiments, intravenous injection of AAVHSC vectors demonstrate widespread systemic tropism. In embodiments, AAVHSCs are capable of crossing the blood-brain barrier. In embodiments, AAVHSCs transduce neurons, astrocytes, oligodendrocytes, and satellite cells in the brain, spinal cord, dorsal root ganglia, as well as the peripheral nervous system.

In certain embodiments, the adeno-associated virus transduced I22I cells includes the nucleotide sequence of SEQ. ID NO: 18. In embodiments, the adeno-associated virus transduced I22I cells is the nucleotide sequence of SEQ. ID NO: 18. In embodiments, the adeno-associated virus transduced I22I cells is a nucleotide sequence having at least 85% sequence identity across the whole sequence or a portion of the sequence of SEQ. ID NO: 18. In embodiments, the adeno-associated virus transduced I22I cells is a nucleotide sequence having at least 86% sequence identity across the whole sequence or a portion of the sequence of SEQ. ID NO: 18. In embodiments, the adeno-associated virus transduced I22I cells is a nucleotide sequence having at least 87% sequence identity across the whole sequence or a portion of the sequence of SEQ. ID NO: 18. In embodiments, the adeno-associated virus transduced I22I cells is a nucleotide sequence having at least 88% sequence identity across the whole sequence or a portion of the sequence of SEQ. ID NO: 18. In embodiments, the adeno-associated virus transduced I22I cells is a nucleotide sequence having at least 89% sequence identity across the whole sequence or a portion of the sequence of SEQ. ID NO: 18. In embodiments, the adeno-associated virus transduced I22I cells is a nucleotide sequence having at least 90% sequence identity across the whole sequence or a portion of the sequence of SEQ. ID NO: 18. In embodiments, the adeno-associated virus transduced I22I cells is a nucleotide sequence having at least 91% sequence identity across the whole sequence or a portion of the sequence of SEQ. ID NO: 18. In embodiments, the adeno-associated virus transduced I22I cells is a nucleotide sequence having at least 92% sequence identity across the whole sequence or a portion of the sequence of SEQ. ID NO: 18. In embodiments, the adeno-associated virus transduced I22I cells is a nucleotide sequence having at least 93% sequence identity across the whole sequence or a portion of the sequence of SEQ. ID NO: 18. In embodiments, the adeno-associated virus transduced I22I cells is a nucleotide sequence having at least 94% sequence identity across the whole sequence or a portion of the sequence of SEQ. ID NO: 18. In embodiments, the adeno-associated virus transduced I22I cells is a nucleotide sequence having at least 95% sequence identity across the whole sequence or a portion of the sequence of SEQ. ID NO: 18. In embodiments, the adeno-associated virus transduced I22I cells is a nucleotide sequence having at least 96% sequence identity across the whole sequence or a portion of the sequence of SEQ. ID NO: 18. In embodiments, the adeno-associated virus transduced I22I cells is a nucleotide sequence having at least 97% sequence identity across the whole sequence or a portion of the sequence of SEQ. ID NO: 18. In embodiments, the adeno-associated virus transduced I22I cells is a nucleotide sequence having at least 98% sequence identity across the whole sequence or a portion of the sequence of SEQ. ID NO: 18. In embodiments, the adeno-associated virus transduced I22I cells is a nucleotide sequence having at least 99% sequence identity across the whole sequence or a portion of the sequence of SEQ. ID NO: 18. In embodiments, the adeno-associated virus transduced I22I cells is a nucleotide sequence has 100% sequence identity across the whole sequence or a portion of the sequence of SEQ. ID NO: 18. In embodiments the adeno-associated virus transduced I22I cells is a nucleotide sequence having 85-86% sequence identity across the whole sequence or a portion of the sequence of SEQ. ID NO: 18. In embodiments the adeno-associated virus transduced I22I cells is a nucleotide sequence having 86-87% sequence identity across the whole sequence or a portion of the sequence of SEQ. ID NO: 18. In embodiments the adeno-associated virus transduced I22I cells is a nucleotide sequence having 87-88% sequence identity across the whole sequence or a portion of the sequence of SEQ. ID NO: 18. In embodiments the adeno-associated virus transduced I22I cells is a nucleotide sequence having 88-89% sequence identity across the whole sequence or a portion of the sequence of SEQ. ID NO: 18. In embodiments the adeno-associated virus transduced I22I cells is a nucleotide sequence having 89-90% sequence identity across the whole sequence or a portion of the sequence of SEQ. ID NO: 18. In embodiments the adeno-associated virus transduced I22I cells is a nucleotide sequence having 90-91% sequence identity across the whole sequence or a portion of the sequence of SEQ. ID NO: 18. In embodiments the adeno-associated virus transduced I22I cells is a nucleotide sequence having 91-92% sequence identity across the whole sequence or a portion of the sequence of SEQ. ID NO: 18. In embodiments the adeno-associated virus transduced I22I cells is a nucleotide sequence having 92-93% sequence identity across the whole sequence or a portion of the sequence of SEQ. ID NO: 18. In embodiments the adeno-associated virus transduced I22I cells is a nucleotide sequence having 93-94% sequence identity across the whole sequence or a portion of the sequence of SEQ. ID NO: 18. In embodiments the adeno-associated virus transduced I22I cells is a nucleotide sequence having 94-95% sequence identity across the whole sequence or a portion of the sequence of SEQ. ID NO: 18. In embodiments the adeno-associated virus transduced I22I cells is a nucleotide sequence having 95-96% sequence identity across the whole sequence or a portion of the sequence of SEQ. ID NO: 18. In embodiments the adeno-associated virus transduced I22I cells is a nucleotide sequence having 96-97% sequence identity across the whole sequence or a portion of the sequence of SEQ. ID NO: 18. In embodiments the adeno-associated virus transduced I22I cells is a nucleotide sequence having 97-98% sequence identity across the whole sequence or a portion of the sequence of SEQ. ID NO: 18. In embodiments the adeno-associated virus transduced I22I cells is a nucleotide sequence having 98-99% sequence identity across the whole sequence or a portion of the sequence of SEQ. ID NO: 18. In embodiments the adeno-associated virus transduced I22I cells is a nucleotide sequence having 99-100% sequence identity across the whole sequence or a portion of the sequence of SEQ. ID NO: 18.

As used herein, the term "I22I mutation" refers to the intron 22 inversion in the F8 gene. Generally, the intron 22 inversion refers to the intra-chromosomal homologous recombination that involves one of two ~10 kb segments of Xq28 chromosomal DNA. In embodiments, the recombination is at the distal position of these two segments.

As used herein, the term "capsid" refers to a protein shell of a virus comprising the genetic material of the virus.

Correction genomes useful in the AAV compositions disclosed herein generally comprise: (i) an editing element for editing a target locus in an F8 gene, (ii) a 5' homology arm nucleotide sequence 5' to the editing element having homology to a first genomic region 5' to the target locus, and (iii) a 3' homology arm nucleotide sequence 3' to the editing element having homology to a second genomic region 3' to the target locus, wherein the portion of the correction genome comprising the 5' homology arm, editing element, and 3' homology arm can be in the sense or antisense orientation relative to the F8 gene locus.

As used herein, "editing elements" used in the correction genomes refer to insertion, deletion, or substitution of one or more nucleotides at the target locus. In certain embodiments, when correctly integrated by homologous recombination at the target locus, the editing element corrects a mutation in an F8 gene back to the wild-type F8 sequence or a functional equivalent thereof. In certain embodiments, the editing element comprises a wild-type or silently altered sequence of exons 23-26 of an F8 gene (e.g., the human F8 gene). In certain embodiments, the editing element comprises at least a portion of an F8 coding sequence. In certain embodiments, the portion of the F8 coding sequence comprises the sequences of exons 23-26 of an F8 gene, optionally further comprising the sequences of one or more of exons 15-22 in the same order as in a genome (e.g., human genome).

In certain embodiments, the editing element comprises a portion of an F8 coding sequence (e.g., a portion of a wild-type F8 coding sequence, or a portion of a silently altered F8 coding sequence). Such editing elements can further comprise a splice acceptor site and/or an exogenous polyadenylation sequence. In certain embodiments, the editing element comprises 5' to 3': a splice acceptor site; a portion of an F8 coding sequence (e.g., a portion of a wild-type F8 coding sequence, or a portion of a silently altered F8 coding sequence); and an exogenous polyadenylation sequence. In certain embodiments, the portion of the F8 coding sequence comprises the sequences of exons 23-26 of an F8 gene.

In certain embodiments, the F8 coding sequence includes the nucleotide sequence of SEQ. ID NO: 15. In embodiments, the F8 coding sequence is the nucleotide sequence of SEQ. ID NO: 15. In embodiments, the F8 coding sequence is a nucleotide sequence having at least 85% sequence identity across the whole sequence of SEQ. ID NO: 15. In embodiments, the F8 coding sequence is a nucleotide sequence having at least 86% sequence identity across the whole sequence of SEQ. ID NO: 15. In embodiments, the F8 coding sequence is a nucleotide sequence having at least 87% sequence identity across the whole sequence of SEQ. ID NO: 15. In embodiments, the F8 coding sequence is a nucleotide sequence having at least 88% sequence identity across the whole sequence of SEQ. ID NO: 15. In embodiments, the F8 coding sequence is a nucleotide sequence having at least 89% sequence identity across the whole sequence of SEQ. ID NO: 15. In embodiments, the F8 coding sequence is a nucleotide sequence having at least 90% sequence identity across the whole sequence of SEQ. ID NO: 15. In embodiments, the F8 coding sequence is a nucleotide sequence having at least 91% sequence identity across the whole sequence of SEQ. ID NO: 15. In embodiments, the F8 coding sequence is a nucleotide sequence having at least 92% sequence identity across the whole sequence of SEQ. ID NO: 15. In embodiments, the F8 coding sequence is a nucleotide sequence having at least 93% sequence identity across the whole sequence of SEQ. ID NO: 15. In embodiments, the F8 coding sequence is a nucleotide sequence having at least 94% sequence identity across the whole sequence of SEQ. ID NO: 15. In embodiments, the F8 coding sequence is a nucleotide sequence having at least 95% sequence identity across the whole sequence of SEQ. ID NO: 15. In embodiments, the F8 coding sequence is a nucleotide sequence having at least 96% sequence identity across the whole sequence of SEQ. ID NO: 15. In embodiments, the F8 coding sequence is a nucleotide sequence having at least 97% sequence identity across the whole sequence of SEQ. ID NO: 15. In embodiments, the F8 coding sequence is a nucleotide sequence having at least 98% sequence identity across the whole sequence of SEQ. ID NO: 15. In embodiments, the F8 coding sequence is a nucleotide sequence having at least 99% sequence identity across the whole sequence of SEQ. ID NO: 15. In embodiments, the F8 coding sequence is a nucleotide sequence has 100% sequence identity across the whole sequence of SEQ. ID NO: 15. In embodiments, the F8 coding sequence is a nucleotide sequence having 85-86%, 86-87%, 87-88%, 88-89%, 89-90%, 90-91%, 91-92%, 92-93%, 93-94%, 94-95%, 95-96%, 96-97%, 97-98%, 98-99%, or 99-100% sequence identity across the whole sequence of SEQ. ID NO: 15. In embodiments, the F8 coding sequence is a nucleotide sequence having 86-87% sequence identity across the whole sequence of SEQ. ID NO: 15. In embodiments, the F8 coding sequence is a nucleotide sequence having 87-88% sequence identity across the whole sequence of SEQ. ID NO: 15. In embodiments, the F8 coding sequence is a nucleotide sequence having 88-89% sequence identity across the whole sequence of SEQ. ID NO: 15. In embodiments, the F8 coding sequence is a nucleotide sequence having 89-90% sequence identity across the whole sequence of SEQ. ID NO: 15. In embodiments, the F8 coding sequence is a nucleotide sequence having 90-91% sequence identity across the whole sequence of SEQ. ID NO: 15. In embodiments, the F8 coding sequence is a nucleotide sequence having 91-92% sequence identity across the whole sequence of SEQ. ID NO: 15. In embodiments, the F8 coding sequence is a nucleotide sequence having 92-93% sequence identity across the whole sequence of SEQ. ID NO: 15. In embodiments, the F8 coding sequence is a nucleotide sequence having 93-94% sequence identity across the whole sequence of SEQ. ID NO: 15. In embodiments, the F8 coding sequence is a nucleotide sequence having 94-95% sequence identity across the whole sequence of SEQ. ID NO: 15. In embodiments, the F8 coding sequence is a nucleotide sequence having 95-96% sequence identity across the whole sequence of SEQ. ID NO: 15. In embodiments, the F8 coding sequence is a nucleotide sequence having 96-97% sequence identity across the whole sequence of SEQ. ID NO: 15. In embodiments, the F8 coding sequence is a nucleotide sequence having 97-98% sequence identity across the whole sequence of SEQ. ID NO: 15. In embodiments, the F8 coding sequence is a nucleotide sequence having 98-99% sequence identity across the whole sequence of SEQ. ID NO: 15. In embodiments, the F8 coding sequence is a nucleotide sequence having 99-100% sequence identity across the whole sequence of SEQ. ID NO: 15.

In certain embodiments, the F8 coding sequence includes the nucleotide sequence of SEQ. ID NO: 16. In embodiments, the F8 coding sequence is the nucleotide sequence of SEQ. ID NO: 16. In embodiments, the F8 coding sequence is a nucleotide sequence having at least 85% sequence identity across the whole sequence of SEQ. ID NO: 16. In embodiments, the F8 coding sequence is a nucleotide sequence having at least 86% sequence identity across the whole sequence of SEQ. ID NO: 16. In embodiments, the F8 coding sequence is a nucleotide sequence having at least 87% sequence identity across the whole sequence of SEQ. ID NO: 16. In embodiments, the F8 coding sequence is a nucleotide sequence having at least 88% sequence identity across the whole sequence of SEQ. ID NO: 16. In embodiments, the F8 coding sequence is a nucleotide sequence having at least 89% sequence identity across the whole sequence of SEQ. ID NO: 16. In embodiments, the F8 coding sequence is a nucleotide sequence having at least 90% sequence identity across the whole sequence of SEQ. ID NO: 16. In embodiments, the F8 coding sequence is a nucleotide sequence having at least 91% sequence identity across the whole sequence of SEQ. ID NO: 16. In embodiments, the F8 coding sequence is a nucleotide sequence having at least 92% sequence identity across the whole sequence of SEQ. ID NO: 16. In embodiments, the F8 coding sequence is a nucleotide sequence having at least 93% sequence identity across the whole sequence of SEQ. ID NO: 16. In embodiments, the F8 coding sequence is a nucleotide sequence having at least 94% sequence identity across the whole sequence of SEQ. ID NO: 16. In embodiments, the F8 coding sequence is a nucleotide sequence having at least 95% sequence identity across the whole sequence of SEQ. ID NO: 16. In embodiments, the F8 coding sequence is a nucleotide sequence having at least 96% sequence identity across the whole sequence of SEQ. ID NO: 16. In embodiments, the F8 coding sequence is a nucleotide sequence having at least 97% sequence identity across the whole sequence of SEQ. ID NO: 16. In embodiments, the F8 coding sequence is a nucleotide sequence having at least 98% sequence identity across the whole sequence of SEQ. ID NO: 16. In embodiments, the F8 coding sequence is a nucleotide sequence having at least 99% sequence identity across the whole sequence of SEQ. ID NO: 16. In embodiments, the F8 coding sequence is a nucleotide sequence has 100% sequence identity across the whole sequence of SEQ. ID NO: 16. In embodiments, the F8 coding sequence is a nucleotide sequence having 85-86% sequence identity across the whole sequence of SEQ. ID NO: 16. In embodiments, the F8 coding sequence is a nucleotide sequence having 86-87% sequence identity across the whole sequence of SEQ. ID NO: 16. In embodiments, the F8 coding sequence is a nucleotide sequence having 87-88% sequence identity across the whole sequence of SEQ. ID NO: 16. In embodiments, the F8 coding sequence is a nucleotide sequence having 88-89% sequence identity across the whole sequence of SEQ. ID NO: 16. In embodiments, the F8 coding sequence is a nucleotide sequence having 89-90% sequence identity across the whole sequence of SEQ. ID NO: 16. In embodiments, the F8 coding sequence is a nucleotide sequence having 90-91% sequence identity across the whole sequence of SEQ. ID NO: 16. In embodiments, the F8 coding sequence is a nucleotide sequence having 91-92% sequence identity across the whole sequence of SEQ. ID NO: 16. In embodiments, the F8 coding sequence is a nucleotide sequence having 92-93% sequence identity across the whole sequence of SEQ. ID NO: 16. In embodiments, the F8 coding sequence is a nucleotide sequence having 93-94% sequence identity across the whole sequence of SEQ. ID NO: 16. In embodiments, the F8 coding sequence is a nucleotide sequence having 94-95% sequence identity across the whole sequence of SEQ. ID NO: 16. In embodiments, the F8 coding sequence is a nucleotide sequence having 95-96% sequence identity across the whole sequence of SEQ. ID NO: 16. In embodiments, the F8 coding sequence is a nucleotide sequence having 96-97% sequence identity across the whole sequence of SEQ. ID NO: 16. In embodiments, the F8 coding sequence is a nucleotide sequence having 97-98% sequence identity across the whole sequence of SEQ. ID NO: 16. In embodiments, the F8 coding sequence is a nucleotide sequence having 98-99% sequence identity across the whole sequence of SEQ. ID NO: 16. In embodiments, the F8 coding sequence is a nucleotide sequence having 99-100% sequence identity across the whole sequence of SEQ. ID NO: 16.

In certain embodiments, the F8 coding sequence includes the nucleotide sequence of SEQ. ID NO: 17. In embodiments, the F8 coding sequence is the nucleotide sequence of SEQ. ID NO: 17. In embodiments, the F8 coding sequence is a nucleotide sequence having at least 85%, 86%, 87%, 88%, 89%, 90%, 91%, 92%, 93%, 94%, 95%, 96%, 97%, 98%, 99%, or 100% sequence identity across the whole sequence of SEQ. ID NO: 17. In embodiments, the F8 coding sequence is a nucleotide sequence having at least 86% sequence identity across the whole sequence of SEQ. ID NO: 17. In embodiments, the F8 coding sequence is a nucleotide sequence having at least 87% sequence identity across the whole sequence of SEQ. ID NO: 17. In embodiments, the F8 coding sequence is a nucleotide sequence having at least 88% sequence identity across the whole sequence of SEQ. ID NO: 17. In embodiments, the F8 coding sequence is a nucleotide sequence having at least 89% sequence identity across the whole sequence of SEQ. ID NO: 17. In embodiments, the F8 coding sequence is a nucleotide sequence having at least 90% sequence identity across the whole sequence of SEQ. ID NO: 17. In embodiments, the F8 coding sequence is a nucleotide sequence having at least 91% sequence identity across the whole sequence of SEQ. ID NO: 17. In embodiments, the F8 coding sequence is a nucleotide sequence having at least 92% sequence identity across the whole sequence of SEQ. ID NO: 17. In embodiments, the F8 coding sequence is a nucleotide sequence having at least 93% sequence identity across the whole sequence of SEQ. ID NO: 17. In embodiments, the F8 coding sequence is a nucleotide sequence having at least 94% sequence identity across the whole sequence of SEQ. ID NO: 17. In embodiments, the F8 coding sequence is a nucleotide sequence having at least 95% sequence identity across the whole sequence of SEQ. ID NO: 17. In embodiments, the F8 coding sequence is a nucleotide sequence having at least 96% sequence identity across the whole sequence of SEQ. ID NO: 17. In embodiments, the F8 coding sequence is a nucleotide sequence having at least 97% sequence identity across the whole sequence of SEQ. ID NO: 17. In embodiments, the F8 coding sequence is a nucleotide sequence having at least 98% sequence identity across the whole sequence of SEQ. ID NO: 17. In embodiments, the F8 coding sequence is a nucleotide sequence having at least 99% sequence identity across the whole sequence of SEQ. ID NO: 17. In embodiments, the F8 coding sequence is a nucleotide sequence has 100% sequence identity across the whole sequence of SEQ. ID NO: 17. In embodiments, the F8 coding sequence is a nucleotide sequence having 85-86% sequence identity across the whole sequence of SEQ. ID NO: 17. In embodiments, the F8 coding sequence is a nucleotide sequence having 86-87% sequence identity across the whole sequence of SEQ. ID NO: 17. In embodiments, the F8 coding sequence is a nucleotide sequence having 87-88% sequence identity across the whole sequence of SEQ. ID NO: 16. In embodiments, the F8 coding sequence is a nucleotide sequence having 88-89% sequence identity across the whole sequence of SEQ. ID NO: 17. In embodiments, the F8 coding sequence is a nucleotide sequence having 89-90% sequence identity across the whole sequence of SEQ. ID NO: 17. In embodiments, the F8 coding sequence is a nucleotide sequence having 90-91% sequence identity across the whole sequence of SEQ. ID NO: 17. In embodiments, the F8 coding sequence is a nucleotide sequence having 91-92% sequence identity across the whole sequence of SEQ. ID NO: 17. In embodiments, the F8 coding sequence is a nucleotide sequence having 92-93% sequence identity across the whole sequence of SEQ. ID NO: 17. In embodiments, the F8 coding sequence is a nucleotide sequence having 93-94% sequence identity across the whole sequence of SEQ. ID NO: 17. In embodiments, the F8 coding sequence is a nucleotide sequence having 94-95% sequence identity across the whole sequence of SEQ. ID NO: 17. In embodiments, the F8 coding sequence is a nucleotide sequence having 95-96% sequence identity across the whole sequence of SEQ. ID NO: 17. In embodiments, the F8 coding sequence is a nucleotide sequence having 96-97% sequence identity across the whole sequence of SEQ. ID NO: 17. In embodiments, the F8 coding sequence is a nucleotide sequence having 97-98% sequence identity across the whole sequence of SEQ. ID NO: 17. In embodiments, the F8 coding sequence is a nucleotide sequence having 98-99% sequence identity across the whole sequence of SEQ. ID NO: 17. In embodiments, the F8 coding sequence is a nucleotide sequence having 99-100% sequence identity across the whole sequence of SEQ. ID NO: 17.

The term "replication-defective recombinant adeno-associated virus" refers to packaging systems for recombinant preparation of a replication-defective AAV. Such packaging systems generally comprise: a Rep nucleotide sequence encoding one or more AAV Rep proteins; a Cap nucleotide sequence encoding one or more AAV Clade F capsid proteins as disclosed herein; and a correction genome for correction of the F8 gene as disclosed herein, wherein the packaging system is operative in a cell for enclosing the correction genome in the capsid to form the AAV.

In certain embodiments, the correction genome includes the 5' homology arm nucleotide sequence 5' to the editing element having homology to a first genomic region 5' to the target locus of SEQ. ID NO: 1. In embodiments, the 5' homology arm nucleotide sequence is SEQ. ID NO: 1. In embodiments, the 5' homology arm nucleotide sequence is a nucleotide having at least 85% sequence identity across the whole sequence of SEQ. ID NO: 1. In embodiments, the 5' homology arm nucleotide sequence is a nucleotide having at least 86% sequence identity across the whole sequence of SEQ. ID NO: 1. In embodiments, the 5' homology arm nucleotide sequence is a nucleotide having at least 87% sequence identity across the whole sequence of SEQ. ID NO: 1. In embodiments, the 5' homology arm nucleotide sequence is a nucleotide having at least 88% sequence identity across the whole sequence of SEQ. ID NO: 1. In embodiments, the 5' homology arm nucleotide sequence is a nucleotide having at least 89% sequence identity across the whole sequence of SEQ. ID NO: 1. In embodiments, the 5' homology arm nucleotide sequence is a nucleotide having at least 90% sequence identity across the whole sequence of SEQ. ID NO: 1. In embodiments, the 5' homology arm nucleotide sequence is a nucleotide having at least 91% sequence identity across the whole sequence of SEQ. ID NO: 1. In embodiments, the 5' homology arm nucleotide sequence is a nucleotide having at least 92% sequence identity across the whole sequence of SEQ. ID NO: 1. In embodiments, the 5' homology arm nucleotide sequence is a nucleotide having at least 93% sequence identity across the whole sequence of SEQ. ID NO: 1. In embodiments, the 5' homology arm nucleotide sequence is a nucleotide having at least 94% sequence identity across the whole sequence of SEQ. ID NO: 1. In embodiments, the 5' homology arm nucleotide sequence is a nucleotide having at least 95% sequence identity across the whole sequence of SEQ. ID NO: 1. In embodiments, the 5' homology arm nucleotide sequence is a nucleotide having at least 96% sequence identity across the whole sequence of SEQ. ID NO: 1. In embodiments, the 5' homology arm nucleotide sequence is a nucleotide having at least 97% sequence identity across the whole sequence of SEQ. ID NO: 1. In embodiments, the 5' homology arm nucleotide sequence is a nucleotide having at least 98% sequence identity across the whole sequence of SEQ. ID NO: 1. In embodiments, the 5' homology arm nucleotide sequence is a nucleotide having at least 99% sequence identity across the whole sequence of SEQ. ID NO: 1. In embodiments, the 5' homology arm nucleotide sequence is a nucleotide having 100% sequence identity across the whole sequence of SEQ. ID NO: 1. In embodiments, the 5' homology arm nucleotide sequence is a nucleotide having at least 85-86% sequence identity across the whole sequence of SEQ. ID NO: 1. In embodiments, the 5' homology arm nucleotide sequence is a nucleotide having at least 86-87% sequence identity across the whole sequence of SEQ. ID NO: 1. In embodiments, the 5' homology arm nucleotide sequence is a nucleotide having at least 87-88% sequence identity across the whole sequence of SEQ. ID NO: 1. In embodiments, the 5' homology arm nucleotide sequence is a nucleotide having at least 88-89% sequence identity across the whole sequence of SEQ. ID NO: 1. In embodiments, the 5' homology arm nucleotide sequence is a nucleotide having at least 89-90% sequence identity across the whole sequence of SEQ. ID NO: 1. In embodiments, the 5' homology arm nucleotide sequence is a nucleotide having at least 90-91% sequence identity across the whole sequence of SEQ. ID NO: 1. In embodiments, the 5' homology arm nucleotide sequence is a nucleotide having at least 91-92% sequence identity across the whole sequence of SEQ. ID NO: 1. In embodiments, the 5' homology arm nucleotide sequence is a nucleotide having at least 92-93% sequence identity across the whole sequence of SEQ. ID NO: 1. In embodiments, the 5' homology arm nucleotide sequence is a nucleotide having at least 93-94% sequence identity across the whole sequence of SEQ. ID NO: 1. In embodiments, the 5' homology arm nucleotide sequence is a nucleotide having at least 94-95% sequence identity across the whole sequence of SEQ. ID NO: 1. In embodiments, the 5' homology arm nucleotide sequence is a nucleotide having at least 95-96% sequence identity across the whole sequence of SEQ. ID NO: 1. In embodiments, the 5' homology arm nucleotide sequence is a nucleotide having at least 96-97% sequence identity across the whole sequence of SEQ. ID NO: 1. In embodiments, the 5' homology arm nucleotide sequence is a nucleotide having at least 97-98% sequence identity across the whole sequence of SEQ. ID NO: 1. In embodiments, the 5' homology arm nucleotide sequence is a nucleotide having at least 98-99% sequence identity across the whole sequence of SEQ. ID NO: 1. In embodiments, the 5' homology arm nucleotide sequence is a nucleotide having at least 99-100% sequence identity across the whole sequence of SEQ. ID NO: 1. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 3' homology arm nucleotide sequence 3' to the editing element having homology to a second genomic region 3' to the target locus of SEQ. ID NO: 2. In embodiments, the 3' homology arm nucleotide sequence is SEQ. ID NO: 2. In embodiments, the 3' homology arm nucleotide sequence is a nucleotide having at least 85% sequence identity across the whole sequence of SEQ. ID NO: 2. In embodiments, the 3' homology arm nucleotide sequence is a nucleotide having at least 86% sequence identity across the whole sequence of SEQ. ID NO: 2. In embodiments, the 3' homology arm nucleotide sequence is a nucleotide having at least 87% sequence identity across the whole sequence of SEQ. ID NO: 2. In embodiments, the 3' homology arm nucleotide sequence is a nucleotide having at least 88% sequence identity across the whole sequence of SEQ. ID NO: 2. In embodiments, the 3' homology arm nucleotide sequence is a nucleotide having at least 89% sequence identity across the whole sequence of SEQ. ID NO: 2. In embodiments, the 3' homology arm nucleotide sequence is a nucleotide having at least 90% sequence identity across the whole sequence of SEQ. ID NO: 2. In embodiments, the 3' homology arm nucleotide sequence is a nucleotide having at least 91% sequence identity across the whole sequence of SEQ. ID NO: 2. In embodiments, the 3' homology arm nucleotide sequence is a nucleotide having at least 92% sequence identity across the whole sequence of SEQ. ID NO: 2. In embodiments, the 3' homology arm nucleotide sequence is a nucleotide having at least 93% sequence identity across the whole sequence of SEQ. ID NO: 2. In embodiments, the 3' homology arm nucleotide sequence is a nucleotide having at least 94% sequence identity across the whole sequence of SEQ. ID NO: 2. In embodiments, the 3' homology arm nucleotide sequence is a nucleotide having at least 95% sequence identity across the whole sequence of SEQ. ID NO: 2. In embodiments, the 3' homology arm nucleotide sequence is a nucleotide having at least 96% sequence identity across the whole sequence of SEQ. ID NO: 2. In embodiments, the 3' homology arm nucleotide sequence is a nucleotide having at least 97% sequence identity across the whole sequence of SEQ. ID NO: 2. In embodiments, the 3' homology arm nucleotide sequence is a nucleotide having at least 98% sequence identity across the whole sequence of SEQ. ID NO: 2. In embodiments, the 3' homology arm nucleotide sequence is a nucleotide having at least 99% sequence identity across the whole sequence of SEQ. ID NO: 2. In embodiments, the 3' homology arm nucleotide sequence is a nucleotide has 100% sequence identity across the whole sequence of SEQ. ID NO: 2. In embodiments, the 3' homology arm nucleotide sequence is a nucleotide having at least 85-86% sequence identity across the whole sequence of SEQ. ID NO: 2. In embodiments, the 3' homology arm nucleotide sequence is a nucleotide having at least 86-87% sequence identity across the whole sequence of SEQ. ID NO: 2. In embodiments, the 3' homology arm nucleotide sequence is a nucleotide having at least 87-88% sequence identity across the whole sequence of SEQ. ID NO: 2. In embodiments, the 3' homology arm nucleotide sequence is a nucleotide having at least 88-89% sequence identity across the whole sequence of SEQ. ID NO: 2. In embodiments, the 3' homology arm nucleotide sequence is a nucleotide having at least 89-90% sequence identity across the whole sequence of SEQ. ID NO: 2. In embodiments, the 3' homology arm nucleotide sequence is a nucleotide having at least 90-91% sequence identity across the whole sequence of SEQ. ID NO: 2. In embodiments, the 3' homology arm nucleotide sequence is a nucleotide having at least 91-92% sequence identity across the whole sequence of SEQ. ID NO: 2. In embodiments, the 3' homology arm nucleotide sequence is a nucleotide having at least 92-93% sequence identity across the whole sequence of SEQ. ID NO: 2. In embodiments, the 3' homology arm nucleotide sequence is a nucleotide having at least 93-94% sequence identity across the whole sequence of SEQ. ID NO: 2. In embodiments, the 3' homology arm nucleotide sequence is a nucleotide having at least 94-95% sequence identity across the whole sequence of SEQ. ID NO: 2. In embodiments, the 3' homology arm nucleotide sequence is a nucleotide having at least 95-96% sequence identity across the whole sequence of SEQ. ID NO: 2. In embodiments, the 3' homology arm nucleotide sequence is a nucleotide having at least 96-97% sequence identity across the whole sequence of SEQ. ID NO: 2. In embodiments, the 3' homology arm nucleotide sequence is a nucleotide having at least 97-98% sequence identity across the whole sequence of SEQ. ID NO: 2. In embodiments, the 3' homology arm nucleotide sequence is a nucleotide having at least 98-99% sequence identity across the whole sequence of SEQ. ID NO: 2. In embodiments, the 3' homology arm nucleotide sequence is a nucleotide having at least 99-100% sequence identity across the whole sequence of SEQ. ID NO: 2. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 5' homology arm nucleotide sequence 5' to the editing element having homology to a first genomic region 5' to the target locus of SEQ. ID NO: 3. In embodiments, the 5' homology arm nucleotide sequence is SEQ. ID NO: 3. In embodiments, the 5' homology arm nucleotide sequence is a nucleotide having at least 85% sequence identity across the whole sequence or a portion of the sequence of SEQ. ID NO: 3. In embodiments, the 5' homology arm nucleotide sequence is a nucleotide having at least 86% sequence identity across the whole sequence of SEQ. ID NO: 3. In embodiments, the 5' homology arm nucleotide sequence is a nucleotide having at least 87% sequence identity across the whole sequence of SEQ. ID NO: 3. In embodiments, the 5' homology arm nucleotide sequence is a nucleotide having at least 88% sequence identity across the whole sequence of SEQ. ID NO: 3. In embodiments, the 5' homology arm nucleotide sequence is a nucleotide having at least 89% sequence identity across the whole sequence of SEQ. ID NO: 3. In embodiments, the 5' homology arm nucleotide sequence is a nucleotide having at least 90% sequence identity across the whole sequence of SEQ. ID NO: 3. In embodiments, the 5' homology arm nucleotide sequence is a nucleotide having at least 91% sequence identity across the whole sequence of SEQ. ID NO: 3. In embodiments, the 5' homology arm nucleotide sequence is a nucleotide having at least 92% sequence identity across the whole sequence of SEQ. ID NO: 3. In embodiments, the 5' homology arm nucleotide sequence is a nucleotide having at least 93% sequence identity across the whole sequence of SEQ. ID NO: 3. In embodiments, the 5' homology arm nucleotide sequence is a nucleotide having at least 94% sequence identity across the whole sequence of SEQ. ID NO: 3. In embodiments, the 5' homology arm nucleotide sequence is a nucleotide having at least 95% sequence identity across the whole sequence of SEQ. ID NO: 3. In embodiments, the 5' homology arm nucleotide sequence is a nucleotide having at least 96% sequence identity across the whole sequence of SEQ. ID NO: 3. In embodiments, the 5' homology arm nucleotide sequence is a nucleotide having at least 97% sequence identity across the whole sequence of SEQ. ID NO: 3. In embodiments, the 5' homology arm nucleotide sequence is a nucleotide having at least 98% sequence identity across the whole sequence of SEQ. ID NO: 3. In embodiments, the 5' homology arm nucleotide sequence is a nucleotide having at least 99% sequence identity across the whole sequence of SEQ. ID NO: 3. In embodiments, the 5' homology arm nucleotide sequence is a nucleotide having 100% sequence identity across the whole sequence of SEQ. ID NO: 3. In embodiments, the 5' homology arm nucleotide sequence is a nucleotide having at least 85-86% sequence identity across the whole sequence of SEQ. ID NO: 3. In embodiments, the 5' homology arm nucleotide sequence is a nucleotide having at least 86-87% sequence identity across the whole sequence of SEQ. ID NO: 3. In embodiments, the 5' homology arm nucleotide sequence is a nucleotide having at least 87-88% sequence identity across the whole sequence of SEQ. ID NO: 3. In embodiments, the 5' homology arm nucleotide sequence is a nucleotide having at least 88-89% sequence identity across the whole sequence of SEQ. ID NO: 3. In embodiments, the 5' homology arm nucleotide sequence is a nucleotide having at least 89-90% sequence identity across the whole sequence of SEQ. ID NO: 3. In embodiments, the 5' homology arm nucleotide sequence is a nucleotide having at least 90-91% sequence identity across the whole sequence of SEQ. ID NO: 3. In embodiments, the 5' homology arm nucleotide sequence is a nucleotide having at least 91-92% sequence identity across the whole sequence of SEQ. ID NO: 3. In embodiments, the 5' homology arm nucleotide sequence is a nucleotide having at least 92-93% sequence identity across the whole sequence of SEQ. ID NO: 3. In embodiments, the 5' homology arm nucleotide sequence is a nucleotide having at least 93-94% sequence identity across the whole sequence of SEQ. ID NO: 3. In embodiments, the 5' homology arm nucleotide sequence is a nucleotide having at least 94-95% sequence identity across the whole sequence of SEQ. ID NO: 3. In embodiments, the 5' homology arm nucleotide sequence is a nucleotide having at least 95-96% sequence identity across the whole sequence of SEQ. ID NO: 3. In embodiments, the 5' homology arm nucleotide sequence is a nucleotide having at least 96-97% sequence identity across the whole sequence of SEQ. ID NO: 3. In embodiments, the 5' homology arm nucleotide sequence is a nucleotide having at least 97-98% sequence identity across the whole sequence of SEQ. ID NO: 3. In embodiments, the 5' homology arm nucleotide sequence is a nucleotide having at least 98-99% sequence identity across the whole sequence of SEQ. ID NO: 3. In embodiments, the 5' homology arm nucleotide sequence is a nucleotide having at least 99-100% sequence identity across the whole sequence of SEQ. ID NO: 3. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 3' homology arm nucleotide sequence 3' to the editing element having homology to a second genomic region 3' to the target locus of SEQ. ID NO: 4. In embodiments, the 3' homology arm nucleotide sequence is SEQ. ID NO: 4. In embodiments, the 3' homology arm nucleotide sequence is a nucleotide having at least 85% sequence identity across the whole sequence of SEQ. ID NO: 4. In embodiments, the 3' homology arm nucleotide sequence is a nucleotide having at least 86% sequence identity across the whole sequence of SEQ. ID NO: 4. In embodiments, the 3' homology arm nucleotide sequence is a nucleotide having at least 87% sequence identity across the whole sequence of SEQ. ID NO: 4. In embodiments, the 3' homology arm nucleotide sequence is a nucleotide having at least 88% sequence identity across the whole sequence of SEQ. ID NO: 4. In embodiments, the 3' homology arm nucleotide sequence is a nucleotide having at least 89% sequence identity across the whole sequence of SEQ. ID NO: 4. In embodiments, the 3' homology arm nucleotide sequence is a nucleotide having at least 90% sequence identity across the whole sequence of SEQ. ID NO: 4. In embodiments, the 3' homology arm nucleotide sequence is a nucleotide having at least 91% sequence identity across the whole sequence of SEQ. ID NO: 4. In embodiments, the 3' homology arm nucleotide sequence is a nucleotide having at least 92% sequence identity across the whole sequence of SEQ. ID NO: 4. In embodiments, the 3' homology arm nucleotide sequence is a nucleotide having at least 93% sequence identity across the whole sequence of SEQ. ID NO: 4. In embodiments, the 3' homology arm nucleotide sequence is a nucleotide having at least 94% sequence identity across the whole sequence of SEQ. ID NO: 4. In embodiments, the 3' homology arm nucleotide sequence is a nucleotide having at least 95% sequence identity across the whole sequence of SEQ. ID NO: 4. In embodiments, the 3' homology arm nucleotide sequence is a nucleotide having at least 96% sequence identity across the whole sequence of SEQ. ID NO: 4. In embodiments, the 3' homology arm nucleotide sequence is a nucleotide having at least 97% sequence identity across the whole sequence of SEQ. ID NO: 4. In embodiments, the 3' homology arm nucleotide sequence is a nucleotide having at least 98% sequence identity across the whole sequence of SEQ. ID NO: 4. In embodiments, the 3' homology arm nucleotide sequence is a nucleotide having at least 99% sequence identity across the whole sequence of SEQ. ID NO: 4. In embodiments, the 3' homology arm nucleotide sequence is a nucleotide has 100% sequence identity across the whole sequence of SEQ. ID NO: 4. In embodiments, the 3' homology arm nucleotide sequence is a nucleotide having at least 85-86% sequence identity across the whole sequence of SEQ. ID NO: 4. In embodiments, the 3' homology arm nucleotide sequence is a nucleotide having at least 86-87% sequence identity across the whole sequence of SEQ. ID NO: 4. In embodiments, the 3' homology arm nucleotide sequence is a nucleotide having at least 87-88% sequence identity across the whole sequence of SEQ. ID NO: 4. In embodiments, the 3' homology arm nucleotide sequence is a nucleotide having at least 88-89% sequence identity across the whole sequence of SEQ. ID NO: 4. In embodiments, the 3' homology arm nucleotide sequence is a nucleotide having at least 89-90% sequence identity across the whole sequence of SEQ. ID NO: 4. In embodiments, the 3' homology arm nucleotide sequence is a nucleotide having at least 90-91% sequence identity across the whole sequence of SEQ. ID NO: 4. In embodiments, the 3' homology arm nucleotide sequence is a nucleotide having at least 91-92% sequence identity across the whole sequence of SEQ. ID NO: 4. In embodiments, the 3' homology arm nucleotide sequence is a nucleotide having at least 92-93% sequence identity across the whole sequence of SEQ. ID NO: 4. In embodiments, the 3' homology arm nucleotide sequence is a nucleotide having at least 93-94% sequence identity across the whole sequence of SEQ. ID NO: 4. In embodiments, the 3' homology arm nucleotide sequence is a nucleotide having at least 94-95% sequence identity across the whole sequence of SEQ. ID NO: 4. In embodiments, the 3' homology arm nucleotide sequence is a nucleotide having at least 95-96% sequence identity across the whole sequence of SEQ. ID NO: 4. In embodiments, the 3' homology arm nucleotide sequence is a nucleotide having at least 96-97% sequence identity across the whole sequence of SEQ. ID NO: 4. In embodiments, the 3' homology arm nucleotide sequence is a nucleotide having at least 97-98% sequence identity across the whole sequence of SEQ. ID NO: 4. In embodiments, the 3' homology arm nucleotide sequence is a nucleotide having at least 98-99% sequence identity across the whole sequence of SEQ. ID NO: 4. In embodiments, the 3' homology arm nucleotide sequence is a nucleotide having at least 99-100% sequence identity across the whole sequence of SEQ. ID NO: 4. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 5' homology arm nucleotide sequence 5' to the editing element having homology to a first genomic region 5' to the target locus of SEQ. ID NO: 5. In embodiments, the 5' homology arm nucleotide sequence is SEQ. ID NO: 5. In embodiments, the 5' homology arm nucleotide sequence is a nucleotide having at least 85% sequence identity across the whole sequence of SEQ. ID NO: 5. In embodiments, the 5' homology arm nucleotide sequence is a nucleotide having at least 86% sequence identity across the whole sequence of SEQ. ID NO: 5. In embodiments, the 5' homology arm nucleotide sequence is a nucleotide having at least 87% sequence identity across the whole sequence of SEQ. ID NO: 5. In embodiments, the 5' homology arm nucleotide sequence is a nucleotide having at least 88% sequence identity across the whole sequence of SEQ. ID NO: 5. In embodiments, the 5' homology arm nucleotide sequence is a nucleotide having at least 89% sequence identity across the whole sequence of SEQ. ID NO: 5. In embodiments, the 5' homology arm nucleotide sequence is a nucleotide having at least 90% sequence identity across the whole sequence of SEQ. ID NO: 5. In embodiments, the 5' homology arm nucleotide sequence is a nucleotide having at least 91% sequence identity across the whole sequence of SEQ. ID NO: 5. In embodiments, the 5' homology arm nucleotide sequence is a nucleotide having at least 92% sequence identity across the whole sequence of SEQ. ID NO: 5. In embodiments, the 5' homology arm nucleotide sequence is a nucleotide having at least 93% sequence identity across the whole sequence of SEQ. ID NO: 5. In embodiments, the 5' homology arm nucleotide sequence is a nucleotide having at least 94% sequence identity across the whole sequence of SEQ. ID NO: 5. In embodiments, the 5' homology arm nucleotide sequence is a nucleotide having at least 95% sequence identity across the whole sequence of SEQ. ID NO: 5. In embodiments, the 5' homology arm nucleotide sequence is a nucleotide having at least 96% sequence identity across the whole sequence of SEQ. ID NO: 5. In embodiments, the 5' homology arm nucleotide sequence is a nucleotide having at least 97% sequence identity across the whole sequence of SEQ. ID NO: 5. In embodiments, the 5' homology arm nucleotide sequence is a nucleotide having at least 98% sequence identity across the whole sequence of SEQ. ID NO: 5. In embodiments, the 5' homology arm nucleotide sequence is a nucleotide having at least 99% sequence identity across the whole sequence of SEQ. ID NO: 5. In embodiments, the 5' homology arm nucleotide sequence is a nucleotide having 100% sequence identity across the whole sequence of SEQ. ID NO: 5. In embodiments, the 5' homology arm nucleotide sequence is a nucleotide having at least 85-86% sequence identity across the whole sequence of SEQ. ID NO: 5. In embodiments, the 5' homology arm nucleotide sequence is a nucleotide having at least 86-87% sequence identity across the whole sequence of SEQ. ID NO: 5. In embodiments, the 5' homology arm nucleotide sequence is a nucleotide having at least 87-88% sequence identity across the whole sequence of SEQ. ID NO: 5. In embodiments, the 5' homology arm nucleotide sequence is a nucleotide having at least 88-89% sequence identity across the whole sequence of SEQ. ID NO: 5. In embodiments, the 5' homology arm nucleotide sequence is a nucleotide having at least 89-90% sequence identity across the whole sequence of SEQ. ID NO: 5. In embodiments, the 5' homology arm nucleotide sequence is a nucleotide having at least 90-91% sequence identity across the whole sequence of SEQ. ID NO: 5. In embodiments, the 5' homology arm nucleotide sequence is a nucleotide having at least 91-92% sequence identity across the whole sequence of SEQ. ID NO: 5. In embodiments, the 5' homology arm nucleotide sequence is a nucleotide having at least 92-93% sequence identity across the whole sequence of SEQ. ID NO: 5. In embodiments, the 5' homology arm nucleotide sequence is a nucleotide having at least 93-94% sequence identity across the whole sequence of SEQ. ID NO: 5. In embodiments, the 5' homology arm nucleotide sequence is a nucleotide having at least 94-95% sequence identity across the whole sequence of SEQ. ID NO: 5. In embodiments, the 5' homology arm nucleotide sequence is a nucleotide having at least 95-96% sequence identity across the whole sequence of SEQ. ID NO: 5. In embodiments, the 5' homology arm nucleotide sequence is a nucleotide having at least 96-97% sequence identity across the whole sequence of SEQ. ID NO: 5. In embodiments, the 5' homology arm nucleotide sequence is a nucleotide having at least 97-98% sequence identity across the whole sequence of SEQ. ID NO: 5. In embodiments, the 5' homology arm nucleotide sequence is a nucleotide having at least 98-99% sequence identity across the whole sequence of SEQ. ID NO: 5. In embodiments, the 5' homology arm nucleotide sequence is a nucleotide having at least 99-100% sequence identity across the whole sequence of SEQ. ID NO: 5. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 3' homology arm nucleotide sequence 3' to the editing element having homology to a second genomic region 3' to the target locus of SEQ. ID NO: 6. In embodiments, the 3' homology arm nucleotide sequence is SEQ. ID NO: 6. In embodiments, the 3' homology arm nucleotide sequence is a nucleotide having at least 85% sequence identity across the whole sequence of SEQ. ID NO: 6. In embodiments, the 3' homology arm nucleotide sequence is a nucleotide having at least 86% sequence identity across the whole sequence of SEQ. ID NO: 6. In embodiments, the 3' homology arm nucleotide sequence is a nucleotide having at least 87% sequence identity across the whole sequence of SEQ. ID NO: 6. In embodiments, the 3' homology arm nucleotide sequence is a nucleotide having at least 88% sequence identity across the whole sequence of SEQ. ID NO: 6. In embodiments, the 3' homology arm nucleotide sequence is a nucleotide having at least 89% sequence identity across the whole sequence of SEQ. ID NO: 6. In embodiments, the 3' homology arm nucleotide sequence is a nucleotide having at least 90% sequence identity across the whole sequence of SEQ. ID NO: 6. In embodiments, the 3' homology arm nucleotide sequence is a nucleotide having at least 91% sequence identity across the whole sequence of SEQ. ID NO: 6. In embodiments, the 3' homology arm nucleotide sequence is a nucleotide having at least 92% sequence identity across the whole sequence of SEQ. ID NO: 6. In embodiments, the 3' homology arm nucleotide sequence is a nucleotide having at least 93% sequence identity across the whole sequence of SEQ. ID NO: 6. In embodiments, the 3' homology arm nucleotide sequence is a nucleotide having at least 94% sequence identity across the whole sequence of SEQ. ID NO: 6. In embodiments, the 3' homology arm nucleotide sequence is a nucleotide having at least 95% sequence identity across the whole sequence of SEQ. ID NO: 6. In embodiments, the 3' homology arm nucleotide sequence is a nucleotide having at least 96% sequence identity across the whole sequence of SEQ. ID NO: 6. In embodiments, the 3' homology arm nucleotide sequence is a nucleotide having at least 97% sequence identity across the whole sequence of SEQ. ID NO: 6. In embodiments, the 3' homology arm nucleotide sequence is a nucleotide having at least 98% sequence identity across the whole sequence of SEQ. ID NO: 6. In embodiments, the 3' homology arm nucleotide sequence is a nucleotide having at least 99% sequence identity across the whole sequence of SEQ. ID NO: 6. In embodiments, the 3' homology arm nucleotide sequence is a nucleotide has 100% sequence identity across the whole sequence of SEQ. ID NO: 6. In embodiments, the 3' homology arm nucleotide sequence is a nucleotide having at least 85-86% sequence identity across the whole sequence of SEQ. ID NO: 6. In embodiments, the 3' homology arm nucleotide sequence is a nucleotide having at least 86-87% sequence identity across the whole sequence of SEQ. ID NO: 6. In embodiments, the 3' homology arm nucleotide sequence is a nucleotide having at least 87-88% sequence identity across the whole sequence of SEQ. ID NO: 6. In embodiments, the 3' homology arm nucleotide sequence is a nucleotide having at least 88-89% sequence identity across the whole sequence of SEQ. ID NO: 6. In embodiments, the 3' homology arm nucleotide sequence is a nucleotide having at least 89-90% sequence identity across the whole sequence of SEQ. ID NO: 6. In embodiments, the 3' homology arm nucleotide sequence is a nucleotide having at least 90-91% sequence identity across the whole sequence of SEQ. ID NO: 6. In embodiments, the 3' homology arm nucleotide sequence is a nucleotide having at least 91-92% sequence identity across the whole sequence of SEQ. ID NO: 6. In embodiments, the 3' homology arm nucleotide sequence is a nucleotide having at least 92-93% sequence identity across the whole sequence of SEQ. ID NO: 6. In embodiments, the 3' homology arm nucleotide sequence is a nucleotide having at least 93-94% sequence identity across the whole sequence of SEQ. ID NO: 6. In embodiments, the 3' homology arm nucleotide sequence is a nucleotide having at least 94-95% sequence identity across the whole sequence of SEQ. ID NO: 6. In embodiments, the 3' homology arm nucleotide sequence is a nucleotide having at least 95-96% sequence identity across the whole sequence of SEQ. ID NO: 6. In embodiments, the 3' homology arm nucleotide sequence is a nucleotide having at least 96-97% sequence identity across the whole sequence of SEQ. ID NO: 6. In embodiments, the 3' homology arm nucleotide sequence is a nucleotide having at least 97-98% sequence identity across the whole sequence of SEQ. ID NO: 6. In embodiments, the 3' homology arm nucleotide sequence is a nucleotide having at least 98-99% sequence identity across the whole sequence of SEQ. ID NO: 6. In embodiments, the 3' homology arm nucleotide sequence is a nucleotide having at least 99-100% sequence identity across the whole sequence of SEQ. ID NO: 6. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 5' homology arm nucleotide sequence 5' to the editing element having homology to a first genomic region 5' to the target locus of SEQ. ID NO: 7. In embodiments, the 5' homology arm nucleotide sequence is SEQ. ID NO: 7. In embodiments, the 5' homology arm nucleotide sequence is a nucleotide having at least 85% sequence identity across the whole sequence of SEQ. ID NO: 7. In embodiments, the 5' homology arm nucleotide sequence is a nucleotide having at least 86% sequence identity across the whole sequence of SEQ. ID NO: 7. In embodiments, the 5' homology arm nucleotide sequence is a nucleotide having at least 87% sequence identity across the whole sequence of SEQ. ID NO: 7. In embodiments, the 5' homology arm nucleotide sequence is a nucleotide having at least 88% sequence identity across the whole sequence of SEQ. ID NO: 7. In embodiments, the 5' homology arm nucleotide sequence is a nucleotide having at least 89% sequence identity across the whole sequence of SEQ. ID NO: 7. In embodiments, the 5' homology arm nucleotide sequence is a nucleotide having at least 90% sequence identity across the whole sequence of SEQ. ID NO: 7. In embodiments, the 5' homology arm nucleotide sequence is a nucleotide having at least 91% sequence identity across the whole sequence of SEQ. ID NO: 7. In embodiments, the 5' homology arm nucleotide sequence is a nucleotide having at least 92% sequence identity across the whole sequence of SEQ. ID NO: 7. In embodiments, the 5' homology arm nucleotide sequence is a nucleotide having at least 93% sequence identity across the whole sequence of SEQ. ID NO: 7. In embodiments, the 5' homology arm nucleotide sequence is a nucleotide having at least 94% sequence identity across the whole sequence of SEQ. ID NO: 7. In embodiments, the 5' homology arm nucleotide sequence is a nucleotide having at least 95% sequence identity across the whole sequence of SEQ. ID NO: 7. In embodiments, the 5' homology arm nucleotide sequence is a nucleotide having at least 96% sequence identity across the whole sequence of SEQ. ID NO: 7. In embodiments, the 5' homology arm nucleotide sequence is a nucleotide having at least 97% sequence identity across the whole sequence of SEQ. ID NO: 7. In embodiments, the 5' homology arm nucleotide sequence is a nucleotide having at least 98% sequence identity across the whole sequence of SEQ. ID NO: 7. In embodiments, the 5' homology arm nucleotide sequence is a nucleotide having at least 99% sequence identity across the whole sequence of SEQ. ID NO: 7. In embodiments, the 5' homology arm nucleotide sequence is a nucleotide having 100% sequence identity across the whole sequence of SEQ. ID NO: 7. In embodiments, the 5' homology arm nucleotide sequence is a nucleotide having at least 85-86% sequence identity across the whole sequence of SEQ. ID NO: 7. In embodiments, the 5' homology arm nucleotide sequence is a nucleotide having at least 86-87% sequence identity across the whole sequence of SEQ. ID NO: 7. In embodiments, the 5' homology arm nucleotide sequence is a nucleotide having at least 87-88% sequence identity across the whole sequence of SEQ. ID NO: 7. In embodiments, the 5' homology arm nucleotide sequence is a nucleotide having at least 88-89% sequence identity across the whole sequence of SEQ. ID NO: 7. In embodiments, the 5' homology arm nucleotide sequence is a nucleotide having at least 89-90% sequence identity across the whole sequence of SEQ. ID NO: 7. In embodiments, the 5' homology arm nucleotide sequence is a nucleotide having at least 90-91% sequence identity across the whole sequence of SEQ. ID NO: 7. In embodiments, the 5' homology arm nucleotide sequence is a nucleotide having at least 91-92% sequence identity across the whole sequence of SEQ. ID NO: 7. In embodiments, the 5' homology arm nucleotide sequence is a nucleotide having at least 92-93% sequence identity across the whole sequence of SEQ. ID NO: 7. In embodiments, the 5' homology arm nucleotide sequence is a nucleotide having at least 93-94% sequence identity across the whole sequence of SEQ. ID NO: 7. In embodiments, the 5' homology arm nucleotide sequence is a nucleotide having at least 94-95% sequence identity across the whole sequence of SEQ. ID NO: 7. In embodiments, the 5' homology arm nucleotide sequence is a nucleotide having at least 95-96% sequence identity across the whole sequence of SEQ. ID NO: 7. In embodiments, the 5' homology arm nucleotide sequence is a nucleotide having at least 96-97% sequence identity across the whole sequence of SEQ. ID NO: 7. In embodiments, the 5' homology arm nucleotide sequence is a nucleotide having at least 97-98% sequence identity across the whole sequence of SEQ. ID NO: 7. In embodiments, the 5' homology arm nucleotide sequence is a nucleotide having at least 98-99% sequence identity across the whole sequence of SEQ. ID NO: 7. In embodiments, the 5' homology arm nucleotide sequence is a nucleotide having at least 99-100% sequence identity across the whole sequence of SEQ. ID NO: 7. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 3' homology arm nucleotide sequence 3' to the editing element having homology to a second genomic region 3' to the target locus of SEQ. ID NO: 8. In embodiments, the 3' homology arm nucleotide sequence is SEQ. ID NO: 8. In embodiments, the 3' homology arm nucleotide sequence is a nucleotide having at least 85% sequence identity across the whole sequence of SEQ. ID NO: 8. In embodiments, the 3' homology arm nucleotide sequence is a nucleotide having at least 86% sequence identity across the whole sequence of SEQ. ID NO: 8. In embodiments, the 3' homology arm nucleotide sequence is a nucleotide having at least 87% sequence identity across the whole sequence of SEQ. ID NO: 8. In embodiments, the 3' homology arm nucleotide sequence is a nucleotide having at least 88% sequence identity across the whole sequence of SEQ. ID NO: 8. In embodiments, the 3' homology arm nucleotide sequence is a nucleotide having at least 89% sequence identity across the whole sequence of SEQ. ID NO: 8. In embodiments, the 3' homology arm nucleotide sequence is a nucleotide having at least 90% sequence identity across the whole sequence of SEQ. ID NO: 8. In embodiments, the 3' homology arm nucleotide sequence is a nucleotide having at least 91% sequence identity across the whole sequence of SEQ. ID NO: 8. In embodiments, the 3' homology arm nucleotide sequence is a nucleotide having at least 92% sequence identity across the whole sequence of SEQ. ID NO: 8. In embodiments, the 3' homology arm nucleotide sequence is a nucleotide having at least 93% sequence identity across the whole sequence of SEQ. ID NO: 8. In embodiments, the 3' homology arm nucleotide sequence is a nucleotide having at least 94% sequence identity across the whole sequence of SEQ. ID NO: 8. In embodiments, the 3' homology arm nucleotide sequence is a nucleotide having at least 95% sequence identity across the whole sequence of SEQ. ID NO: 8. In embodiments, the 3' homology arm nucleotide sequence is a nucleotide having at least 96% sequence identity across the whole sequence of SEQ. ID NO: 8. In embodiments, the 3' homology arm nucleotide sequence is a nucleotide having at least 97% sequence identity across the whole sequence of SEQ. ID NO: 8. In embodiments, the 3' homology arm nucleotide sequence is a nucleotide having at least 98% sequence identity across the whole sequence of SEQ. ID NO: 8. In embodiments, the 3' homology arm nucleotide sequence is a nucleotide having at least 99% sequence identity across the whole sequence of SEQ. ID NO: 8. In embodiments, the 3' homology arm nucleotide sequence is a nucleotide has 100% sequence identity across the whole sequence of SEQ. ID NO: 8. In embodiments, the 3' homology arm nucleotide sequence is a nucleotide having at least 85-86% sequence identity across the whole sequence of SEQ. ID NO: 8. In embodiments, the 3' homology arm nucleotide sequence is a nucleotide having at least 86-87% sequence identity across the whole sequence of SEQ. ID NO: 8. In embodiments, the 3' homology arm nucleotide sequence is a nucleotide having at least 87-88% sequence identity across the whole sequence of SEQ. ID NO: 8. In embodiments, the 3' homology arm nucleotide sequence is a nucleotide having at least 88-89% sequence identity across the whole sequence of SEQ. ID NO: 8. In embodiments, the 3' homology arm nucleotide sequence is a nucleotide having at least 89-90% sequence identity across the whole sequence of SEQ. ID NO: 8. In embodiments, the 3' homology arm nucleotide sequence is a nucleotide having at least 90-91% sequence identity across the whole sequence of SEQ. ID NO: 8. In embodiments, the 3' homology arm nucleotide sequence is a nucleotide having at least 91-92% sequence identity across the whole sequence of SEQ. ID NO: 8. In embodiments, the 3' homology arm nucleotide sequence is a nucleotide having at least 92-93% sequence identity across the whole sequence of SEQ. ID NO: 8. In embodiments, the 3' homology arm nucleotide sequence is a nucleotide having at least 93-94% sequence identity across the whole sequence of SEQ. ID NO: 8. In embodiments, the 3' homology arm nucleotide sequence is a nucleotide having at least 94-95% sequence identity across the whole sequence of SEQ. ID NO: 8. In embodiments, the 3' homology arm nucleotide sequence is a nucleotide having at least 95-96% sequence identity across the whole sequence of SEQ. ID NO: 8. In embodiments, the 3' homology arm nucleotide sequence is a nucleotide having at least 96-97% sequence identity across the whole sequence of SEQ. ID NO: 8. In embodiments, the 3' homology arm nucleotide sequence is a nucleotide having at least 97-98% sequence identity across the whole sequence of SEQ. ID NO: 8. In embodiments, the 3' homology arm nucleotide sequence is a nucleotide having at least 98-99% sequence identity across the whole sequence of SEQ. ID NO: 8. In embodiments, the 3' homology arm nucleotide sequence is a nucleotide having at least 99-100% sequence identity across the whole sequence of SEQ. ID NO: 8. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 5' homology arm nucleotide sequence 5' to the editing element having homology to a first genomic region 5' to the target locus of SEQ. ID NO: 9. In embodiments, the 5' homology arm nucleotide sequence is SEQ. ID NO: 9. In embodiments, the 5' homology arm nucleotide sequence is a nucleotide having at least 85% sequence identity across the whole sequence of SEQ. ID NO: 9. In embodiments, the 5' homology arm nucleotide sequence is a nucleotide having at least 86% sequence identity across the whole sequence of SEQ. ID NO: 9. In embodiments, the 5' homology arm nucleotide sequence is a nucleotide having at least 87% sequence identity across the whole sequence of SEQ. ID NO: 9. In embodiments, the 5' homology arm nucleotide sequence is a nucleotide having at least 88% sequence identity across the whole sequence of SEQ. ID NO: 9. In embodiments, the 5' homology arm nucleotide sequence is a nucleotide having at least 89% sequence identity across the whole sequence of SEQ. ID NO: 9. In embodiments, the 5' homology arm nucleotide sequence is a nucleotide having at least 90% sequence identity across the whole sequence of SEQ. ID NO: 9. In embodiments, the 5' homology arm nucleotide sequence is a nucleotide having at least 91% sequence identity across the whole sequence of SEQ. ID NO: 9. In embodiments, the 5' homology arm nucleotide sequence is a nucleotide having at least 92% sequence identity across the whole sequence of SEQ. ID NO: 9. In embodiments, the 5' homology arm nucleotide sequence is a nucleotide having at least 93% sequence identity across the whole sequence of SEQ. ID NO: 9. In embodiments, the 5' homology arm nucleotide sequence is a nucleotide having at least 94% sequence identity across the whole sequence of SEQ. ID NO: 9. In embodiments, the 5' homology arm nucleotide sequence is a nucleotide having at least 95% sequence identity across the whole sequence of SEQ. ID NO: 9. In embodiments, the 5' homology arm nucleotide sequence is a nucleotide having at least 96% sequence identity across the whole sequence of SEQ. ID NO: 9. In embodiments, the 5' homology arm nucleotide sequence is a nucleotide having at least 97% sequence identity across the whole sequence of SEQ. ID NO: 9. In embodiments, the 5' homology arm nucleotide sequence is a nucleotide having at least 98% sequence identity across the whole sequence of SEQ. ID NO: 9. In embodiments, the 5' homology arm nucleotide sequence is a nucleotide having at least 99% sequence identity across the whole sequence of SEQ. ID NO: 9. In embodiments, the 5' homology arm nucleotide sequence is a nucleotide having 100% sequence identity across the whole sequence of SEQ. ID NO: 9. In embodiments, the 5' homology arm nucleotide sequence is a nucleotide having at least 85-86% sequence identity across the whole sequence of SEQ. ID NO: 9. In embodiments, the 5' homology arm nucleotide sequence is a nucleotide having at least 86-87% sequence identity across the whole sequence of SEQ. ID NO: 9. In embodiments, the 5' homology arm nucleotide sequence is a nucleotide having at least 87-88% sequence identity across the whole sequence of SEQ. ID NO: 9. In embodiments, the 5' homology arm nucleotide sequence is a nucleotide having at least 88-89% sequence identity across the whole sequence of SEQ. ID NO: 9. In embodiments, the 5' homology arm nucleotide sequence is a nucleotide having at least 89-90% sequence identity across the whole sequence of SEQ. ID NO: 9. In embodiments, the 5' homology arm nucleotide sequence is a nucleotide having at least 90-91% sequence identity across the whole sequence of SEQ. ID NO: 9. In embodiments, the 5' homology arm nucleotide sequence is a nucleotide having at least 91-92% sequence identity across the whole sequence of SEQ. ID NO: 9. In embodiments, the 5' homology arm nucleotide sequence is a nucleotide having at least 92-93% sequence identity across the whole sequence of SEQ. ID NO: 9. In embodiments, the 5' homology arm nucleotide sequence is a nucleotide having at least 93-94% sequence identity across the whole sequence of SEQ. ID NO: 9. In embodiments, the 5' homology arm nucleotide sequence is a nucleotide having at least 94-95% sequence identity across the whole sequence of SEQ. ID NO: 9. In embodiments, the 5' homology arm nucleotide sequence is a nucleotide having at least 95-96% sequence identity across the whole sequence of SEQ. ID NO: 9. In embodiments, the 5' homology arm nucleotide sequence is a nucleotide having at least 96-97% sequence identity across the whole sequence of SEQ. ID NO: 9. In embodiments, the 5' homology arm nucleotide sequence is a nucleotide having at least 97-98% sequence identity across the whole sequence of SEQ. ID NO: 9. In embodiments, the 5' homology arm nucleotide sequence is a nucleotide having at least 98-99% sequence identity across the whole sequence of SEQ. ID NO: 9. In embodiments, the 5' homology arm nucleotide sequence is a nucleotide having at least 99-100% sequence identity across the whole sequence of SEQ. ID NO: 9. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 3' homology arm nucleotide sequence 3' to the editing element having homology to a second genomic region 3' to the target locus of SEQ. ID NO: 10. In embodiments, the 3' homology arm nucleotide sequence is SEQ. ID NO: 10. In embodiments, the 3' homology arm nucleotide sequence is a nucleotide having at least 85% sequence identity across the whole sequence of SEQ. ID NO: 10. In embodiments, the 3' homology arm nucleotide sequence is a nucleotide having at least 86% sequence identity across the whole sequence of SEQ. ID NO: 10. In embodiments, the 3' homology arm nucleotide sequence is a nucleotide having at least 87% sequence identity across the whole sequence of SEQ. ID NO: 10. In embodiments, the 3' homology arm nucleotide sequence is a nucleotide having at least 88% sequence identity across the whole sequence of SEQ. ID NO: 10. In embodiments, the 3' homology arm nucleotide sequence is a nucleotide having at least 89% sequence identity across the whole sequence of SEQ. ID NO: 10. In embodiments, the 3' homology arm nucleotide sequence is a nucleotide having at least 90% sequence identity across the whole sequence of SEQ. ID NO: 10. In embodiments, the 3' homology arm nucleotide sequence is a nucleotide having at least 91% sequence identity across the whole sequence of SEQ. ID NO: 10. In embodiments, the 3' homology arm nucleotide sequence is a nucleotide having at least 92% sequence identity across the whole sequence of SEQ. ID NO: 10. In embodiments, the 3' homology arm nucleotide sequence is a nucleotide having at least 93% sequence identity across the whole sequence of SEQ. ID NO: 10. In embodiments, the 3' homology arm nucleotide sequence is a nucleotide having at least 94% sequence identity across the whole sequence of SEQ. ID NO: 10. In embodiments, the 3' homology arm nucleotide sequence is a nucleotide having at least 95% sequence identity across the whole sequence of SEQ. ID NO: 10. In embodiments, the 3' homology arm nucleotide sequence is a nucleotide having at least 96% sequence identity across the whole sequence of SEQ. ID NO: 10. In embodiments, the 3' homology arm nucleotide sequence is a nucleotide having at least 97% sequence identity across the whole sequence of SEQ. ID NO: 10. In embodiments, the 3' homology arm nucleotide sequence is a nucleotide having at least 98% sequence identity across the whole sequence of SEQ. ID NO: 10. In embodiments, the 3' homology arm nucleotide sequence is a nucleotide having at least 99% sequence identity across the whole sequence of SEQ. ID NO: 10. In embodiments, the 3' homology arm nucleotide sequence is a nucleotide has 100% sequence identity across the whole sequence of SEQ. ID NO: 10. In embodiments, the 3' homology arm nucleotide sequence is a nucleotide having at least 85-86% sequence identity across the whole sequence of SEQ. ID NO: 10. In embodiments, the 3' homology arm nucleotide sequence is a nucleotide having at least 86-87% sequence identity across the whole sequence of SEQ. ID NO: 10. In embodiments, the 3' homology arm nucleotide sequence is a nucleotide having at least 87-88% sequence identity across the whole sequence of SEQ. ID NO: 10. In embodiments, the 3' homology arm nucleotide sequence is a nucleotide having at least 88-89% sequence identity across the whole sequence of SEQ. ID NO: 10. In embodiments, the 3' homology arm nucleotide sequence is a nucleotide having at least 89-90% sequence identity across the whole sequence of SEQ. ID NO: 10. In embodiments, the 3' homology arm nucleotide sequence is a nucleotide having at least 90-91% sequence identity across the whole sequence of SEQ. ID NO: 10. In embodiments, the 3' homology arm nucleotide sequence is a nucleotide having at least 91-92% sequence identity across the whole sequence of SEQ. ID NO: 10. In embodiments, the 3' homology arm nucleotide sequence is a nucleotide having at least 92-93% sequence identity across the whole sequence of SEQ. ID NO: 10. In embodiments, the 3' homology arm nucleotide sequence is a nucleotide having at least 93-94% sequence identity across the whole sequence of SEQ. ID NO: 10. In embodiments, the 3' homology arm nucleotide sequence is a nucleotide having at least 94-95% sequence identity across the whole sequence of SEQ. ID NO: 10. In embodiments, the 3' homology arm nucleotide sequence is a nucleotide having at least 95-96% sequence identity across the whole sequence of SEQ. ID NO: 10. In embodiments, the 3' homology arm nucleotide sequence is a nucleotide having at least 96-97% sequence identity across the whole sequence of SEQ. ID NO: 10. In embodiments, the 3' homology arm nucleotide sequence is a nucleotide having at least 97-98% sequence identity across the whole sequence of SEQ. ID NO: 10. In embodiments, the 3' homology arm nucleotide sequence is a nucleotide having at least 98-99% sequence identity across the whole sequence of SEQ. ID NO: 10. In embodiments, the 3' homology arm nucleotide sequence is a nucleotide having at least 99-100% sequence identity across the whole sequence of SEQ. ID NO: 10. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 5' homology arm nucleotide sequence 5' to the editing element having homology to a first genomic region 5' to the target locus of SEQ. ID NO: 11. In embodiments, the 5' homology arm nucleotide sequence is SEQ. ID NO: 11. In embodiments, the 5' homology arm nucleotide sequence is a nucleotide having at least 85% sequence identity across the whole sequence of SEQ. ID NO: 11. In embodiments, the 5' homology arm nucleotide sequence is a nucleotide having at least 86% sequence identity across the whole sequence of SEQ. ID NO: 11. In embodiments, the 5' homology arm nucleotide sequence is a nucleotide having at least 87% sequence identity across the whole sequence of SEQ. ID NO: 11. In embodiments, the 5' homology arm nucleotide sequence is a nucleotide having at least 88% sequence identity across the whole sequence of SEQ. ID NO: 11. In embodiments, the 5' homology arm nucleotide sequence is a nucleotide having at least 89% sequence identity across the whole sequence of SEQ. ID NO: 11. In embodiments, the 5' homology arm nucleotide sequence is a nucleotide having at least 90% sequence identity across the whole sequence of SEQ. ID NO: 11. In embodiments, the 5' homology arm nucleotide sequence is a nucleotide having at least 91% sequence identity across the whole sequence of SEQ. ID NO: 11. In embodiments, the 5' homology arm nucleotide sequence is a nucleotide having at least 92% sequence identity across the whole sequence of SEQ. ID NO: 11. In embodiments, the 5' homology arm nucleotide sequence is a nucleotide having at least 93% sequence identity across the whole sequence of SEQ. ID NO: 11. In embodiments, the 5' homology arm nucleotide sequence is a nucleotide having at least 94% sequence identity across the whole sequence of SEQ. ID NO: 11. In embodiments, the 5' homology arm nucleotide sequence is a nucleotide having at least 95% sequence identity across the whole sequence of SEQ. ID NO: 11. In embodiments, the 5' homology arm nucleotide sequence is a nucleotide having at least 96% sequence identity across the whole sequence of SEQ. ID NO: 11. In embodiments, the 5' homology arm nucleotide sequence is a nucleotide having at least 97% sequence identity across the whole sequence of SEQ. ID NO: 11. In embodiments, the 5' homology arm nucleotide sequence is a nucleotide having at least 98% sequence identity across the whole sequence of SEQ. ID NO: 11. In embodiments, the 5' homology arm nucleotide sequence is a nucleotide having at least 99% sequence identity across the whole sequence of SEQ. ID NO: 11. In embodiments, the 5' homology arm nucleotide sequence is a nucleotide having 100% sequence identity across the whole sequence of SEQ. ID NO: 11. In embodiments, the 5' homology arm nucleotide sequence is a nucleotide having at least 85-86% sequence identity across the whole sequence of SEQ. ID NO: 11. In embodiments, the 5' homology arm nucleotide sequence is a nucleotide having at least 86-87% sequence identity across the whole sequence of SEQ. ID NO: 11. In embodiments, the 5' homology arm nucleotide sequence is a nucleotide having at least 87-88% sequence identity across the whole sequence of SEQ. ID NO: 11. In embodiments, the 5' homology arm nucleotide sequence is a nucleotide having at least 88-89% sequence identity across the whole sequence of SEQ. ID NO: 11. In embodiments, the 5' homology arm nucleotide sequence is a nucleotide having at least 89-90% sequence identity across the whole sequence of SEQ. ID NO: 11. In embodiments, the 5' homology arm nucleotide sequence is a nucleotide having at least 90-91% sequence identity across the whole sequence of SEQ. ID NO: 11. In embodiments, the 5' homology arm nucleotide sequence is a nucleotide having at least 91-92% sequence identity across the whole sequence of SEQ. ID NO: 11. In embodiments, the 5' homology arm nucleotide sequence is a nucleotide having at least 92-93% sequence identity across the whole sequence of SEQ. ID NO: 11. In embodiments, the 5' homology arm nucleotide sequence is a nucleotide having at least 93-94% sequence identity across the whole sequence of SEQ. ID NO: 11. In embodiments, the 5' homology arm nucleotide sequence is a nucleotide having at least 94-95% sequence identity across the whole sequence of SEQ. ID NO: 11. In embodiments, the 5' homology arm nucleotide sequence is a nucleotide having at least 95-96% sequence identity across the whole sequence of SEQ. ID NO: 11. In embodiments, the 5' homology arm nucleotide sequence is a nucleotide having at least 96-97% sequence identity across the whole sequence of SEQ. ID NO: 11. In embodiments, the 5' homology arm nucleotide sequence is a nucleotide having at least 97-98% sequence identity across the whole sequence of SEQ. ID NO: 11. In embodiments, the 5' homology arm nucleotide sequence is a nucleotide having at least 98-99% sequence identity across the whole sequence of SEQ. ID NO: 11. In embodiments, the 5' homology arm nucleotide sequence is a nucleotide having at least 99-100% sequence identity across the whole sequence of SEQ. ID NO: 11. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 3' homology arm nucleotide sequence 3' to the editing element having homology to a second genomic region 3' to the target locus of SEQ. ID NO: 12. In embodiments, the 3' homology arm nucleotide sequence is SEQ. ID NO: 12. In embodiments, the 3' homology arm nucleotide sequence is a nucleotide having at least 85% sequence identity across the whole sequence of SEQ. ID NO: 12. In embodiments, the 3' homology arm nucleotide sequence is a nucleotide having at least 86% sequence identity across the whole sequence of SEQ. ID NO: 12. In embodiments, the 3' homology arm nucleotide sequence is a nucleotide having at least 87% sequence identity across the whole sequence of SEQ. ID NO: 12. In embodiments, the 3' homology arm nucleotide sequence is a nucleotide having at least 88% sequence identity across the whole sequence of SEQ. ID NO: 12. In embodiments, the 3' homology arm nucleotide sequence is a nucleotide having at least 89% sequence identity across the whole sequence of SEQ. ID NO: 12. In embodiments, the 3' homology arm nucleotide sequence is a nucleotide having at least 90% sequence identity across the whole sequence of SEQ. ID NO: 12. In embodiments, the 3' homology arm nucleotide sequence is a nucleotide having at least 91% sequence identity across the whole sequence of SEQ. ID NO: 12. In embodiments, the 3' homology arm nucleotide sequence is a nucleotide having at least 92% sequence identity across the whole sequence of SEQ. ID NO: 12. In embodiments, the 3' homology arm nucleotide sequence is a nucleotide having at least 93% sequence identity across the whole sequence of SEQ. ID NO: 12. In embodiments, the 3' homology arm nucleotide sequence is a nucleotide having at least 94% sequence identity across the whole sequence of SEQ. ID NO: 12. In embodiments, the 3' homology arm nucleotide sequence is a nucleotide having at least 95% sequence identity across the whole sequence of SEQ. ID NO: 12. In embodiments, the 3' homology arm nucleotide sequence is a nucleotide having at least 96% sequence identity across the whole sequence of SEQ. ID NO: 12. In embodiments, the 3' homology arm nucleotide sequence is a nucleotide having at least 97% sequence identity across the whole sequence of SEQ. ID NO: 12. In embodiments, the 3' homology arm nucleotide sequence is a nucleotide having at least 98% sequence identity across the whole sequence of SEQ. ID NO: 12. In embodiments, the 3' homology arm nucleotide sequence is a nucleotide having at least 99% sequence identity across the whole sequence of SEQ. ID NO: 12. In embodiments, the 3' homology arm nucleotide sequence is a nucleotide has 100% sequence identity across the whole sequence of SEQ. ID NO: 12. In embodiments, the 3' homology arm nucleotide sequence is a nucleotide having at least 85-86% sequence identity across the whole sequence of SEQ. ID NO: 12. In embodiments, the 3' homology arm nucleotide sequence is a nucleotide having at least 86-87% sequence identity across the whole sequence of SEQ. ID NO: 12. In embodiments, the 3' homology arm nucleotide sequence is a nucleotide having at least 87-88% sequence identity across the whole sequence of SEQ. ID NO: 12. In embodiments, the 3' homology arm nucleotide sequence is a nucleotide having at least 88-89% sequence identity across the whole sequence of SEQ. ID NO: 12. In embodiments, the 3' homology arm nucleotide sequence is a nucleotide having at least 89-90% sequence identity across the whole sequence of SEQ. ID NO: 12. In embodiments, the 3' homology arm nucleotide sequence is a nucleotide having at least 90-91% sequence identity across the whole sequence of SEQ. ID NO: 12. In embodiments, the 3' homology arm nucleotide sequence is a nucleotide having at least 91-92% sequence identity across the whole sequence of SEQ. ID NO: 12. In embodiments, the 3' homology arm nucleotide sequence is a nucleotide having at least 92-93% sequence identity across the whole sequence of SEQ. ID NO: 12. In embodiments, the 3' homology arm nucleotide sequence is a nucleotide having at least 93-94% sequence identity across the whole sequence of SEQ. ID NO: 12. In embodiments, the 3' homology arm nucleotide sequence is a nucleotide having at least 94-95% sequence identity across the whole sequence of SEQ. ID NO: 12. In embodiments, the 3' homology arm nucleotide sequence is a nucleotide having at least 95-96% sequence identity across the whole sequence of SEQ. ID NO: 12. In embodiments, the 3' homology arm nucleotide sequence is a nucleotide having at least 96-97% sequence identity across the whole sequence of SEQ. ID NO: 12. In embodiments, the 3' homology arm nucleotide sequence is a nucleotide having at least 97-98% sequence identity across the whole sequence of SEQ. ID NO: 12. In embodiments, the 3' homology arm nucleotide sequence is a nucleotide having at least 98-99% sequence identity across the whole sequence of SEQ. ID NO: 12. In embodiments, the 3' homology arm nucleotide sequence is a nucleotide having at least 99-100% sequence identity across the whole sequence of SEQ. ID NO: 12. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 5' homology arm nucleotide sequence 5' to the editing element having homology to a first genomic region 5' to the target locus of SEQ. ID NO: 13. In embodiments, the 5' homology arm nucleotide sequence is SEQ. ID NO: 13. In embodiments, the 5' homology arm nucleotide sequence is a nucleotide having at least 85% sequence identity across the whole sequence of SEQ. ID NO: 13. In embodiments, the 5' homology arm nucleotide sequence is a nucleotide having at least 86% sequence identity across the whole sequence of SEQ. ID NO: 13. In embodiments, the 5' homology arm nucleotide sequence is a nucleotide having at least 87% sequence identity across the whole sequence of SEQ. ID NO: 13. In embodiments, the 5' homology arm nucleotide sequence is a nucleotide having at least 88% sequence identity across the whole sequence of SEQ. ID NO: 13. In embodiments, the 5' homology arm nucleotide sequence is a nucleotide having at least 89% sequence identity across the whole sequence of SEQ. ID NO: 13. In embodiments, the 5' homology arm nucleotide sequence is a nucleotide having at least 90% sequence identity across the whole sequence of SEQ. ID NO: 13. In embodiments, the 5' homology arm nucleotide sequence is a nucleotide having at least 91% sequence identity across the whole sequence of SEQ. ID NO: 13. In embodiments, the 5' homology arm nucleotide sequence is a nucleotide having at least 92% sequence identity across the whole sequence of SEQ. ID NO: 13. In embodiments, the 5' homology arm nucleotide sequence is a nucleotide having at least 93% sequence identity across the whole sequence of SEQ. ID NO: 13. In embodiments, the 5' homology arm nucleotide sequence is a nucleotide having at least 94% sequence identity across the whole sequence of SEQ. ID NO: 13. In embodiments, the 5' homology arm nucleotide sequence is a nucleotide having at least 95% sequence identity across the whole sequence of SEQ. ID NO: 13. In embodiments, the 5' homology arm nucleotide sequence is a nucleotide having at least 96% sequence identity across the whole sequence of SEQ. ID NO: 13. In embodiments, the 5' homology arm nucleotide sequence is a nucleotide having at least 97% sequence identity across the whole sequence of SEQ. ID NO: 13. In embodiments, the 5' homology arm nucleotide sequence is a nucleotide having at least 98% sequence identity across the whole sequence of SEQ. ID NO: 3. In embodiments, the 5' homology arm nucleotide sequence is a nucleotide having at least 99% sequence identity across the whole sequence of SEQ. ID NO: 3. In embodiments, the 5' homology arm nucleotide sequence is a nucleotide having 100% sequence identity across the whole sequence of SEQ. ID NO: 13. In embodiments, the 5' homology arm nucleotide sequence is a nucleotide having at least 85-86% sequence identity across the whole sequence of SEQ. ID NO: 13. In embodiments, the 5' homology arm nucleotide sequence is a nucleotide having at least 86-87% sequence identity across the whole sequence of SEQ. ID NO: 13. In embodiments, the 5' homology arm nucleotide sequence is a nucleotide having at least 87-88% sequence identity across the whole sequence of SEQ. ID NO: 13. In embodiments, the 5' homology arm nucleotide sequence is a nucleotide having at least 88-89% sequence identity across the whole sequence of SEQ. ID NO: 13. In embodiments, the 5' homology arm nucleotide sequence is a nucleotide having at least 89-90% sequence identity across the whole sequence of SEQ. ID NO: 13. In embodiments, the 5' homology arm nucleotide sequence is a nucleotide having at least 90-91% sequence identity across the whole sequence of SEQ. ID NO: 13. In embodiments, the 5' homology arm nucleotide sequence is a nucleotide having at least 91-92% sequence identity across the whole sequence of SEQ. ID NO: 13. In embodiments, the 5' homology arm nucleotide sequence is a nucleotide having at least 92-93% sequence identity across the whole sequence of SEQ. ID NO: 13. In embodiments, the 5' homology arm nucleotide sequence is a nucleotide having at least 93-94% sequence identity across the whole sequence of SEQ. ID NO: 13. In embodiments, the 5' homology arm nucleotide sequence is a nucleotide having at least 94-95% sequence identity across the whole sequence of SEQ. ID NO: 13. In embodiments, the 5' homology arm nucleotide sequence is a nucleotide having at least 95-96% sequence identity across the whole sequence of SEQ. ID NO: 13. In embodiments, the 5' homology arm nucleotide sequence is a nucleotide having at least 96-97% sequence identity across the whole sequence of SEQ. ID NO: 13. In embodiments, the 5' homology arm nucleotide sequence is a nucleotide having at least 97-98% sequence identity across the whole sequence of SEQ. ID NO: 13. In embodiments, the 5' homology arm nucleotide sequence is a nucleotide having at least 98-99% sequence identity across the whole sequence of SEQ. ID NO: 13. In embodiments, the 5' homology arm nucleotide sequence is a nucleotide having at least 99-100% sequence identity across the whole sequence of SEQ. ID NO: 13. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the correction genome includes the 3' homology arm nucleotide sequence 3' to the editing element having homology to a second genomic region 3' to the target locus of SEQ. ID NO: 14. In embodiments, the 3' homology arm nucleotide sequence is SEQ. ID NO: 14. In embodiments, the 3' homology arm nucleotide sequence is a nucleotide having at least 85% sequence identity across the whole sequence of SEQ. ID NO: 14. In embodiments, the 3' homology arm nucleotide sequence is a nucleotide having at least 86% sequence identity across the whole sequence of SEQ. ID NO: 14. In embodiments, the 3' homology arm nucleotide sequence is a nucleotide having at least 87% sequence identity across the whole sequence of SEQ. ID NO: 14. In embodiments, the 3' homology arm nucleotide sequence is a nucleotide having at least 88% sequence identity across the whole sequence of SEQ. ID NO: 14. In embodiments, the 3' homology arm nucleotide sequence is a nucleotide having at least 89% sequence identity across the whole sequence of SEQ. ID NO: 14. In embodiments, the 3' homology arm nucleotide sequence is a nucleotide having at least 90% sequence identity across the whole sequence of SEQ. ID NO: 14. In embodiments, the 3' homology arm nucleotide sequence is a nucleotide having at least 91% sequence identity across the whole sequence of SEQ. ID NO: 14. In embodiments, the 3' homology arm nucleotide sequence is a nucleotide having at least 92% sequence identity across the whole sequence of SEQ. ID NO: 14. In embodiments, the 3' homology arm nucleotide sequence is a nucleotide having at least 93% sequence identity across the whole sequence of SEQ. ID NO: 14. In embodiments, the 3' homology arm nucleotide sequence is a nucleotide having at least 94% sequence identity across the whole sequence of SEQ. ID NO: 14. In embodiments, the 3' homology arm nucleotide sequence is a nucleotide having at least 95% sequence identity across the whole sequence of SEQ. ID NO: 14. In embodiments, the 3' homology arm nucleotide sequence is a nucleotide having at least 96% sequence identity across the whole sequence of SEQ. ID NO: 14. In embodiments, the 3' homology arm nucleotide sequence is a nucleotide having at least 97% sequence identity across the whole sequence of SEQ. ID NO: 14. In embodiments, the 3' homology arm nucleotide sequence is a nucleotide having at least 98% sequence identity across the whole sequence of SEQ. ID NO: 14. In embodiments, the 3' homology arm nucleotide sequence is a nucleotide having at least 99% sequence identity across the whole sequence of SEQ. ID NO: 14. In embodiments, the 3' homology arm nucleotide sequence is a nucleotide has 100% sequence identity across the whole sequence of SEQ. ID NO: 14. In embodiments, the 3' homology arm nucleotide sequence is a nucleotide having at least 85-86% sequence identity across the whole sequence of SEQ. ID NO: 14. In embodiments, the 3' homology arm nucleotide sequence is a nucleotide having at least 86-87% sequence identity across the whole sequence of SEQ. ID NO: 14. In embodiments, the 3' homology arm nucleotide sequence is a nucleotide having at least 87-88% sequence identity across the whole sequence of SEQ. ID NO: 14. In embodiments, the 3' homology arm nucleotide sequence is a nucleotide having at least 88-89% sequence identity across the whole sequence of SEQ. ID NO: 14. In embodiments, the 3' homology arm nucleotide sequence is a nucleotide having at least 89-90% sequence identity across the whole sequence of SEQ. ID NO: 14. In embodiments, the 3' homology arm nucleotide sequence is a nucleotide having at least 90-91% sequence identity across the whole sequence of SEQ. ID NO: 14. In embodiments, the 3' homology arm nucleotide sequence is a nucleotide having at least 91-92% sequence identity across the whole sequence of SEQ. ID NO: 14. In embodiments, the 3' homology arm nucleotide sequence is a nucleotide having at least 92-93% sequence identity across the whole sequence of SEQ. ID NO: 14. In embodiments, the 3' homology arm nucleotide sequence is a nucleotide having at least 93-94% sequence identity across the whole sequence of SEQ. ID NO: 14. In embodiments, the 3' homology arm nucleotide sequence is a nucleotide having at least 94-95% sequence identity across the whole sequence of SEQ. ID NO: 14. In embodiments, the 3' homology arm nucleotide sequence is a nucleotide having at least 95-96% sequence identity across the whole sequence of SEQ. ID NO: 14. In embodiments, the 3' homology arm nucleotide sequence is a nucleotide having at least 96-97% sequence identity across the whole sequence of SEQ. ID NO: 14. In embodiments, the 3' homology arm nucleotide sequence is a nucleotide having at least 97-98% sequence identity across the whole sequence of SEQ. ID NO: 14. In embodiments, the 3' homology arm nucleotide sequence is a nucleotide having at least 98-99% sequence identity across the whole sequence of SEQ. ID NO: 14. In embodiments, the 3' homology arm nucleotide sequence is a nucleotide having at least 99-100% sequence identity across the whole sequence of SEQ. ID NO: 14. In embodiments, the correction genome does not include any F8 gene coding sequence other than the recited SEQ. ID NOS. herein for the editing element, the 5' homology arm, and the 3' homology arm. In embodiments, the replication-defective adeno-associated virus (AAV) comprising the AAV capsid and the correction genome, does not include any other F8 coding sequence other than the recited SEQ. ID NOS herein for the editing element, the 5' homology arm and the 3' homology arm.

In certain embodiments, the packaging system comprises a first vector comprising the Rep nucleotide sequence and the Cap nucleotide sequence, and a second vector comprising the correction genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.) Any AAV Rep protein can be employed in the packaging systems disclosed herein. In embodiments of the packaging system, the first, second, and/or third vector are contained within one or more transfecting plasmids.

As used herein, the packing system may further comprise a third vector, e.g., a helper virus vector. The third vector may be an independent third vector, integral with the first vector, or integral with the second vector. In certain embodiments, the third vector comprises genes encoding helper virus proteins. The helper virus may be selected from, but not limited to, adenovirus, herpes virus (including herpes simplex virus (HSV)), poxvirus (such as vaccinia virus), cytomegalovirus (CMV), and baculovirus.

III. Methods

In an aspect, provided herein is are methods for treating diseases associated with an F8 gene mutation.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism. Non-limiting examples include humans, other mammals, bovines, rats, mice, dogs, monkeys, goat, sheep, cows, and other non-mammalian animals. In aspects, a patient is human. In aspects, a patient is human that has cancer.

A "effective amount," as used herein, is an amount sufficient for a compound to accomplish a stated purpose relative to the absence of the compound (e.g. achieve the effect for which it is administered, treat a disease, reduce a signaling pathway, or reduce one or more symptoms of a disease or condition). In these methods, the effective amount of the active agent (e.g., oncolytic virus, viral vector) described herein is an amount effective to accomplish the stated purpose of the method. An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "therapeutically effective amount," as used herein, refers to that amount of the therapeutic agent sufficient to ameliorate the disorder, as described above. For example, for the given parameter, a therapeutically effective amount will show an increase or decrease of at least 1%, 2%, 3%, 4%, 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 0.01-fold, 0.02-fold, 0.03-fold, 0.04-fold, 0.05-fold, 0.06-fold, 0.07-fold, 0.08-fold, 0.09-fold, 0.10-fold, 0.20-fold, 0.30-fold, 0.40-fold, 0.50-fold, 0.60-fold, 0.70-fold, 0.80-fold 0.90-fold, 1.0-fold, 1.1-fold, 1.2-fold, 1.5-fold, 2-fold, 5-fold, or more effect over a control. For any compound described herein, the therapeutically effective amount can be initially determined from cell culture assays. Target concentrations will be those concentrations of active compound(s) that are capable of achieving the methods described herein, as measured using the methods described herein or known in the art. As is in the art, therapeutically effective amounts for use in humans can also be determined from animal models. For example, a dose for humans can be formulated to achieve a concentration that has been found to be effective in animals.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

The term "administering" refers to intranasal administration, inhalation administration, oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include the use of lipid nanoparticles, aerosols, liposomal formulations, intravenous infusion, transdermal patches, and the like. In aspects, administering does not include administration of any active agent other than the oncolytic virus or viral vector. In aspects, administration is intranasal. In aspects, administration is intravenous.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation).

EXAMPLES

The recombinant AAV vectors provided herein mediate highly efficient gene editing. Useful examples known in the art can also be found in International Application No. PCT/US2019/018502, herein incorporated by reference in its entirety.

Example 1

Approximately 45% of hemophilia A patients carry the I22I inversion in which exons 1-22 of the Factor VIII gene (F8) are inverted relative to exons 23-26. This inversion splits the full length FVIII protein into two truncated proteins which are transcribed in opposite directions. To correct the I22 inversion and restore the full length FVIII protein, AAVHSC-mediated targeted insertion of the cDNA of FVIII exons 23-26 at the end of exon22 of the FVIII gene was evaluated. AAVHSC editing vectors mediate homologous recombination-based genome editing without the need for prior nuclease-mediated cleavage of genomic DNA. The design of FVIII I22I editing vectors for the insertion of promoterless reporters downstream of exon 22 of the F8 gene was investigated. Flow cytometry and sequence analysis showed that AAVHSC editing vectors successfully inserted the promoterless mCherry open reading frame (ORF) at specified locations within the FVIII gene in both cell lines as well as primary human and canine liver sinusoidal endothelial cells (LSEC) in vitro. Editing vectors for FVIII gene correction were designed to insert codon optimized exon 23 to 26 cDNA and a reporter gene coding region. The homology arms were designed to insert the correction cassette at the end of exon 22 of the FVIII gene, such that successful correction of the I22 inversion would be dependent upon transcription from the chromosomal FVIII promoter. Specific mCherry expression in AAVHSC edited primary human LSEC indicated successful insertion of the correction sequence in the FVIII gene. The frequency of editing ranged from 7% to >30% in primary human LSEC and was dependent upon homology arm configurations. Editing was confirmed at the molecular level by targeted integration assays employing amplification of junction sequences using mCherry-specific and chromosome-specific primers. Sequence analysis revealed precise and seamless insertion of the exon 23-26 cassette into the FVIII gene and the absence of insertion/deletion mutations. Surprisingly, data confirmed expression of the correction cassette in primary human and canine endothelial cells.

Methods

Packaging of recombinant AAVHSC editing vectors was performed as essentially as described in US 2019/0276856 (herein incorporated by reference), Smith et al. Mol Ther 2014 and Smith et al. PNAS 2018.

Fusion of correction sequences (codon-optimized Exons 23-26) to a FLAG tag was performed to allow specific detection of the transgene insert (as opposed to wild type FVIII protein). Immunoprecipitation and Western blot analyses were performed either singly or sequentially to detect the protein FVIII-FLAG product made by AAVHSC edited cells.

Immunoprecipitation of FLAG-Tagged VIII

Serum free medium from transduced or untransduced human LSEC was concentrated prior to immunoprecipitation with a cocktail of monoclonal anti-FVIII antibodies and Protein A+G beads. Precipitated proteins were electrophoresed on reducing SDS-PAGE gels and transferred to PVDF membranes. Western blots were probed with monoclonal anti-FLAG antibodies and processed as per the standard protocol.

Western Blot Analysis of FVIII in Transduced Human Liver Endothelial Cells

Human LSEC were transduced with editing vectors at multiplicity of infection: 150,000. Untransduced cells were used as controls. After 24 hours, the medium was changed to serum free medium (SFM), collected after another 24 hours and concentrated using 10 KD concentrators. 30 μg protein per sample were electrophoresed on reducing SDS-Page and transferred to PVDF membrane at 4° C. Western blots were blocked with 5% nonfat dry milk and probed with 1 ug/ml of either an anti-F8 antibody (GMA-012) or and anti-FLAG antibody (Sigma #F1804) diluted in 3% nonfat dry milk overnight at 4° C. After washes, membranes were incubated with 1:5000 rabbit anti mouse-HRP antibodies at room temperature and developed with Pierce West Dura ECL solution for 5 minutes and imaged.

Assay of F8 Gene Expression in Primary Human Liver Endothelial Cells by qRT-PCR 1,00,000-2,00,000 cells (human LSECs) were seeded into wells of 24-well or 12-well plate, respectively with 750 ul complete medium (Cell Systems), one day before transduction and incubated at 37° C., 5% $CO_2$ The next day, the medium was replaced with fresh complete medium (750 μl) and cells were transduced at MOI 1,50,000. The plates were incubated at 37° C., 5% $CO_2$ for 48 h. After 48 h of transduction, cells were washed with ice-cold PBS and detached using RNA lysis buffer and cell scraper. RNA was extracted from cells using Qiagen RNeasy/MN nucleospin RNA plus kit as per manufacturer's instructions with following modification where an additional step of DNase I treatment was done on-column after wash with MDB buffer. DNase I reaction mix was added to the column and incubated at RT for 15 min. After 15 min, the column was washed with wash buffer and RNA was eluted. The concentration of RNA was estimated using Nanodrop followed by which it was reverse transcribed to cDNA using SuperScript™ IV First-Strand Synthesis System (Invitrogen). qPCR for FVIII and mCherry were then performed using 5 ng cDNA for each reaction.

Detection of FVIII and FLAG Secretion by Transduced Human LSECs by ELISA (FLAG and FVIII)

The recombinant FLAG-tagged FVIII was also identified by ELISA assays. 1,00,000-2,00,000 cells (human LSECs) were seeded into wells of 24-well or 12-well plate, respectively with 750 ul complete medium (Cell systems), a day before transduction and incubated at 37° C., 5% $CO_2$. 24 hours later the medium was replaced with fresh complete medium (750 μl) and cells were transduced at MOI.150,000. The plates were incubated at 37° C., 5% $CO_2$ for 24 h. After 24 h of transduction, the complete medium was replaced with serum-free medium (SFM) containing culture boost (750 μl) and incubated at 37° C., 5% $CO_2$ for another 24 h. Thereafter, the medium was collected in Eppendorf tubes and protease inhibitor was added. Medium from each well was then concentrated to $1/5^{th}$ of volume using 10 kDa concentrator. The total protein was estimated using Bradford assay and 20 μg of protein was used for FLAG-ELISA (Cayman chemical, USA) and FVIII-ELISA (Biomatik, USA LLC). ELISA's were performed as per manufacturer's instructions.

AAVHSC Editing of the Factor 8 Gene in I22I Patient-Derived Cells

Correction of the I22 inversion of the Factor 8 (F8) gene in immortalized B lymphoblasts derived from a patient with I22I hemophilia A was tested to evaluate AAVHSC editing of the F8 gene. The patient derived I22I cells were edited with AAVHSC vectors designed to insert a cDNA encoding the codon optimized F8 exons 23-26 at the end of F8 exon 22 (FIG. 15). The vectors also encoded a promoterless mCherry expression cassette consisting of a T2A sequence, the mCherry open reading frame and an SV40 polyadenylation (pA) signal. The two editing vectors tested encoded different homology arm (HA) combination. L800R800 encoded right and left HAs of 800 bp. L1900R800 encoded a left HA of 1900 bp and right HA of 800 bp (FIGS. 15 and 16). Upon successful editing, the codon optimized cDNA of exons 23-26 and the T2A-mCherry-pA would be inserted immediately downstream of exon 22 (FIG. 16). The vectors were packaged in AAVHSC15, purified and titered prior to use in experiments.

FIG. 17 shows AAVHSC editing of patient derived I22I B lymphoblasts after transduction with AAVHSC15 L800R800 and L1900R800 vectors. Since the promoterless mCherry cassette was inserted within the F8 gene, expression was directed by the chromosomal F8 promoter. Measurement of mCherry expression allowed quantitation of the editing efficiency. I22I cells were transduced with the AAVHSC F8 editing vectors at multiplicity of infection (MOI) of either 150,000 or 250,000. Flow cytometric analyses revealed that 14.67 to 22.27% of cells expressed mCherry was observed at MOI: 150,000. And, 32.97 to 37.17% editing was observed after transduction at MOI: 250,000. These results showed that AAVHSC successfully edited I22I patient derived cells. Editing efficiency of the F8 locus in I22I cells was observed to increase linearly with MOI (Table 1, FIG. 18), demonstrating that editing was a function of dose of AAVHSC editing vector used.

TABLE 1

Dose Response of Editing of the F8 Gene in I22I B-LCLs with the AAVHSC15 L800R800 and AAVHSC15 L1900R800 Editing Vectors

| Editing Vector | MOI | % Edited (Mean ± SEM) | N |
|---|---|---|---|
| AAVHSC15 L800R800 | 0 | 0.00 | — |
| AAVHSC15 L800R800 | 100000 | 17.65 ± 1.65 | 7 |
| AAVHSC15 L800R800 | 150000 | 26.84 ± 5.54 | 5 |
| AAVHSC15 L800R800 | 250000 | 33.64 ± 5.73 | 3 |
| AAVHSC15 L1900R800 | 0 | 0.00 | — |
| AAVHSC15 L1900R800 | 100000 | 10.83 ± 0.81 | 3 |
| AAVHSC15 L1900R800 | 150000 | 14.07 ± 4.61 | 3 |
| AAVHSC15 L1900R800 | 250000 | 21.77 ± 2.98 | 4 |

Evaluation of Editing at the Sequence Level

Liver sinusoidal endothelial cells (LSEC) were transduced with the AAVHSC L800R800 editing vector at MOI 150,000. Cells were harvested 48 hours post-transduction. Genomic DNA was isolated and amplified using an insert-specific primer complementary to the reporter gene and a primer complementary to chromosomal sequences external to the homology arms (FIGS. 19A-19C). Genomic DNA from untransduced LSEC was used as a negative control. Gel electrophoresis revealed the presence of bands of the expected sizes. FIGS. 20A-20B show gel electrophoretic analysis of the 5' and 3' TI amplicons of the chromosome-insert junctions of the edited F8 gene. Specific bands of 1.8 kb and 1.3 kb representing the 5' and 3' chromosome-insert junctions respectively were observed from edited but not from unedited cells. The bands were excised and cloned. Resulting colonies were screened and sequenced by Sanger sequencing.

FIG. 21 shows the sequences at the chromosome-homology arm and homology arm-insert junctions at the 5' and 3' ends of the edited F8 locus in wild type LSEC. Sequence analysis showed that editing resulted in the seamless insertion of the codon optimized exon 23-26 cDNA at the end of exon 22 of the F8 gene. No on target insertion/deletion mutations were observed following successful editing. Neither was any insertion of AAV sequences including ITRs observed. Neither was there any evidence of sequence alterations in edited cells within or around insertion site.

FIGS. 22A-22B show the TI analysis of the 5' and 3' junction regions of the edited hemophilia A patient derived I22I B lymphoblasts. The expected bands of 1.8 kb (5' junction) and 1.3 kb (3' junction) were observed only in edited but not unedited cells. The sequence of the entire edited region is depicted in the sequence file.

These data show that AAVHSC successfully mediates the precise targeted insertion of the codon optimized cDNA of exons 23-26 at the specified location, the end of exon 22 of the F8 gene without any associated on-target mutations.

Expression of the Corrected Factor VII Protein

Protein was extracted from edited and unedited hemophilia A (I22I) and wild type (Nor) lymphoblasts, electrophoresed on SDS-polyacrylamide gels and Western blots were analyzed by probing with an anti-Factor VIII antibody. The full length FVIII protein and the FVIII light chain, both of which are affected by the I22I inversion, were quantitated by measuring band intensity by ImageJ software and plotted. FIGS. 23A-23B show restoration of expression of both the light chain and the full length FVIII protein in edited I22I cells. Since the editing vector also encoded the FLAG peptide at the end of the exon 23-26 cDNA, we additionally probed Western blots for FLAG expression in edited I22I cells. Successful editing would result in appending the FLAG peptide to the full-length Factor VIII and the Factor VIII light chain. FIGS. 24A-24B show specific FLAG expression in edited I22I cells as compared with unedited and wild type controls. Specific FLAG expression was detected as part of both the full length FVIII protein and the FVIII light chain. Representative Western blot analyses showing expression of complete FVIII chains in edited I22I cell (FIGS. 25A and 25B). For FIG. 25C, I22I inverted patient B-LCLs were transduced with the AAVHSC15 L800R800 editing vector at MOI. 250,000. Cell lysates were immunoprecipitated using a cocktail of anti-FVIII antibodies followed by immunoblotting using a FVIII-specific monoclonal antibody. The single chain FVIII band in I22I cells edited with AAVHSC15 L800R800 showing expression levels higher than untransduced I22I cells. These results demonstrate that edited I22I cells express the FVIII chains of comparable size to wild type, suggesting that AAVHSC15 editing successfully restores protein expression.

Functional Activity of Edited F8 Gene

To evaluate the functional activity of the edited F8 gene, lysates from AAVHSC15 L800R800 edited and unedited cells were assayed for FVIII activity using a chromogenic Coatest assay. FIG. 26 shows that edited LSEC demonstrated higher activity than untransduced LSEC. Wild type LSEC are the natural source of FVIII in vivo. Thus, unedited LSEC are expected to show F8 activity. However, the codon optimized edited F8 gene is expressed more efficiently and therefore FVIII from edited cells has higher activity. These results demonstrate that editing of I22I cells restores functional FVIII expression in cells derived from an I22I hemophilia A patient.

As presented herein, the methods provide AAV correction vectors for editing the I22I inversion of the FVIII gene. These vectors were designed to insert a codon optimized (CO) cDNA of Exons 23-26 at the end of Exon 22 of the FVIII gene followed by a 3× FLAG tag fused to the 3' end. The correction sequence was followed by a T2A sequence and the coding region of mCherry/GFP reporter. The edited cells were designed to express mCherry/GFP from the chromosomal FVIII promoter contain the FLAG tag at the C terminus and was found to differ from the wild type. Accordingly, editing of primary LSEC as well as patient derived I22I B lymphoblasts with the AAVHSC15 L800R00 editing vector corrects the I22I inversion and therefore corrects I22I hemophilia A.

REFERENCES

1. Smith I J, Ul-Hasan T, Carvaines S K, Van Vliet K, Yang E, Wong K K Jr, Agbandje-McKenna M, Chatterjee S. Gene transfer properties and structural modeling of human stem cell-derived AAV. *Mol Ther.* 2014 September; 22(9):1625-34. doi: 10.1038/mt.2014.107. Epub 2014 Jun. 13. PMID: 24925207; PMCID: PMC4435483.
2. Smith L J, Wright J, Clark G, Ul-Hasan T, Jin X, Fong A, Chandra M, St Martin T, Rubin H, Knowlton D, Ellsworth J L, Fong Y, Wong K K Jr, Chatterjee S. Stem cell-derived clade F AAV's mediate high-efficiency homologous recombination-based genome editing. Proc Natl Acad Sci USA. 2018 Jul. 31; 115(31):E7379-E7388. doi: 10.1073/pnas.1802343115. Epub 2018 Jul. 17. Erratum in: Proc Natl Acad Sci USA. 2019 Jan. 2; 116(1):337 PMCID: 30018062; PMCID: PMC6077703.

Informal Sequence Listing

TABLE 2

Homology Pairs for correction of I22I inversion

| Name | Target region | Sequence | SEQ. ID NO |
|---|---|---|---|
| Homology Pair 1 | 5' homology arm 1 | 5'-GTTTCAGGAGGTAGCACATACATTTAAAA ATAGGTTAAAATAAAGTGTTATTTTAATTG GTAGGTGGATCTGTTGGCACCAATGATTAT TCACGGCATCAAGACCCAGGGTGCCCGTCA GAAGTTCTCCAGCCTCTACATCTCTCAGTTT ATCATCATGTATAGTCTTGATGGGAAGAAG TGGCAGACTTATCGAGGAAATTCCACTGGA ACCTTAATG-3' | 1 |
| | 3' homology arm 1 | 5'-GTATGTAATTAGTCATTTAAAGGGAATGC CTGAATACTTTAAAGAATTTTGGCAGATTTC AGATATTGGACAAACACTCTTAGCTTCCACA AACTTAATTCCAAAAAATAATTTTTCACTTA TGAGCAATAGAGTTATTACGGACATATCAGC AAAAATGTAGTAGTGTCAAGGCTCATAGATG ATAGAAATGAAGAGATGCTGTATTGATAGA AAATGTGATTCAGGACTGTGTGGATTGATGA TTGTGAGCTTGCTTATGGATATCCTAGGTTTG AGGTTATAGTAGGACAATCAGGTTGAAATGT CCAGCAGGCAGTAGGTGAAAGACAAGTTTA GGGGGCAAAACCATGGATGGAGATGAAGAT TCATGACTTCCACATAAAAGGATGGGTGAAA CTTTGGGAATTGATGAATTCTCTAGAGGTGA GCTCAAGACCCTTAAAGGCTTAAAACCTCAG CGTTATTGTCTACTCTTCCCTCATTTTTATGCC | 2 |

TABLE 2-continued

| Name | Target region | Sequence | SEQ. ID NO |
|---|---|---|---|
| Homology Pairs for correction of I22I inversion | | | |
| | | CACAAATCTGGTCAATCCTTTATTTGCAATGC CTCTCACATCTCTTTCTTCTGTTTCCATTTATA CCGCTGTTGCCACAGCCCAGGGTCCCATCACC TCACACTTGATCTATTGTATTACATTCCTAACT AGTCTTCCCCCGTTTCTAATCTGTTCTCCGATA AAAGCTGCACATCATTTTCAGGATAATCATCA GTCGCCTGCCTAAAACTTTTCAATGTCTTCCC ATTGTCTTTAGAATAAAGTTCAAAGTCTTCAA ATGACCCCAAGCAAGATAACTTTTGTTTGCC CCTTTAGATCCATTT-3' | |
| Homology Pair 2 | 5' homology arm 2 | 5'-CAGTCTAATAAGGAAAGCAGAAAAGCAAA GCAACCTTATAATATGGTGCAATAATTTGC TATAATGAAGTTATATACAAAGTGAAGTA GAAGCATAGAAGAAGCAGCACTAAATTT GTCTGGGTGAGTCAGAGAAGGCTAACCA GGAAAAATAGTTTCTGAACTAACACTTGA AGGAGGTGTAGCAGTTCATCACTGACAGT GATGTTGGGGTGGGTCTGGTTTCAGGAGA GGGGAGGAAATTGGCTTTGGTCTGAGGCT GAGGTGTGGGCAAAGCATTAGCTTATGTG GGTCCATTAGCTTATGTGAGTCCACAAAA GGTGTGTGTGTGTTTGTGTGTATGTGTGT GTGTGTGTGTGTGTGTGTGTACGAAAT GGGGGCTCAATGATTTGGTAGTGGTTTGG TTTGTCAAGAAGCAGGCTGGGAACTCAAT AAGCATCTTTCCATTCATTTCTACTGTGTA TCCCACAGCTTCACACACACATGCACATT TCAACATTGGTGACTGCTTCACTTGCACA CCTAAGGTAATGATGGACACACCTGTAGC AATGTAGATTCTTCCTAAGCTAATAATTA GTTTCAGGAGGTAGCACATACATTTAAAA ATAGGTTAAAATAAAGTGTTATTTTAATT GGTAGGTGGATCTGTTGGCACCAATGATT ATTCACGGCATCAAGACCCAGGGTGCCC GTCAGAAGTTCTCCAGCCTCTACATCTCT CAGTTTATCATCATGTATAGTCTTGATGG GAAGAAGTGGCAGACTTATCGAGGAAAT TCCACTGGAACCTTAATG-3' | 3 |
| | 3' homology arm 2 | 5'-GTATGTAATTAGTCATTTAAAGGGAATGC CTGAATACTTTAAAGAATTTTGGCAGATT TCAGATATTGGACAAACACTCTTAGCTTCC ACAAACTTAATTCCAAAAAATAATTTTTCA CTTATGAGCAATAGAGTTATTACGGACATA TCAGCAAAAATGTAGTAGTGTCAAGGCTC ATAGATGATAGAAATGAAGAGATGCTGTA TTGATAGAAATATGTGATTCAGGACTGTG TGGATTGATGATTGTGAGCTTGCTTATGG ATATCCTAGGTTTGAGGTTATAGTAGGAC AATCAGGTTGAAATGTCCAGCAGGCAGTA GGTGAAAGACAAGTTTAGGGGGCAAAAC CATGGATGGAGATGAAGATTCATGACTTC CACATAAAAGGATGGGTGAAACTTTGGGA ATTGATGAATTCTCTAGAGGTGAGCTCAA GACCCTTAAAGGCTTAAAACCTCAGCGTT ATTGTCTACTCTTCCCTCATTTTTATGCCC ACAAATCTGGTCAATCCTTTATTTGCAAT GCCTCTCACATCTCTTTCTTCTGTTTCCAT TTATACCGCTGTTGCCACAGCCCAGGGTCC CATCACCTCACACTTGATCTATTGTATTAC ATTCCTAACTAGTCTTCCCCCGTTTCTAAT CTGTTCTCCGATAAAAGCTGCACATCATTT TCAGGATAATCATCAGTCGCCTGCCTAAA ACTTTTCAATGTCTTCCCATTGTCTTTAGA ATAAAGTTCAAAGTCTTCAAATGACCCCA AGCAAGATAACTTTTGTTTGCCCCTTTAG ATCCATTT-3' | 4 |
| Homology Pair 3 | 5' homology arm 3 | 5'-CACCTGGCTGGGCACATAGGTGAAGCTGT TGAGTCTGTAATTGTCAAACTGCTCCCAG GTGCCAATTATAATGTAGAAGAGGCACAA GAAGATGAAGTGGATAAGCCTGGCAGTTT GTCAAGCATTCATCAGTTGTCAAGCATTT GTCAGTTGCAGAATGTAGGTAGGCTGCCA AGGCTTTATTGTAGCCTGGTTCTATTGCAG | 5 |

TABLE 2-continued

| Name | Target region | Sequence | SEQ. ID NO |
|---|---|---|---|
| Homology Pairs for correction of I22I inversion | | | |
| | | CTTTATTCTAGCAAGGCTGCTGGAAAATAC AATAATCACTGGTCCAAGAAAGAACTCTTA TACTCTATCTATATGAAGAAACAGTAAAAG TCAATTCAGTAGAAATCATGATTTTTGTGCC TGGTGCTTTCACTTTTTTATGCCACAATACC AAGAGGTTAAAATGAAGTGTCTTTGATTGG GAATACCATCTATCTGGGAAAAGACAGGGC TGCAACTTCTGAAGACCTTGACACTCTGTCC TGTTACCCTGCTTCATTTTTCTCCTGCGCTTA TCACTACTTGATGCTATAAACAAATAAAAA CATATATGATATAAGGTCTATTTCTCCTACT CAACTGTAAGTTCCATGAGGGCAGGGCTTT CTTTCTTGTTTACTACTCTATTCCCTGTATCT AAAACAGTGCTTGGCACATAGCAAGTGCTA AAAAATATTCTTTGAATGAGTGTATGAATG GAACTTACAGTCAGCTGAAGGAGACAGTTA TTAAGCATAAGAGTGATGACCAGTCCAATT GTGTGTGTCAGGCATGTGTGAAAACGTGCT AAATTTGACTTGCTTATTAGGACAGTAACT GATACTTCTAATGTTCTTGCAGCCCATGAC CTCTTCTTTAAGAAGTGTCCATTCTGTACTA CTTTCCCATTATTCACTCATTCATTCCAAAG CATTTGCTATACAGCAGTATTATACCAGATA CCATATTAGGTGCTGGGGCTAGAGAGAATA TAAAAGCTAACATTGATTGAGTGTTTAGTAT GCGCCAGGCCCTGAACTCAGCACATTACATG TATTAACTCTTTAACCCCTATGGCAGCCCTTT GAGATAAAAACTAATATTATCTTCACTTTACA GATAAGTTGAGACACAGAAAGTTAGGTGACT CAAATGGGTTCACTGCCTTAAGGATCTCAGTC TAATAAGGAAAGCAGAAAAGCAAAGCAACC TTATAATATGGTGCAATAATTTGCTATAATGA AGTTATATACAAAGTGAAGTAGAAGCATAGA AGAAGCAGCACTAAATTTGTCTGGGTGAGTC AGAGAAGGCTAACCAGGAAAAATAGTTTCT GAACTAACACTTGAAGGAGGTGTAGCAGTTC ATCACTGACAGTGATGTTGGGGTGGGTCTGG TTTCAGGAGAGGGGAGGAAATTGGCTTTGGT CTGAGGCTGAGGTGTGGGCAAAGCATTAGCT TATGTGGGTCCATTAGCTTATGTGAGTCCA CAAAAGGTGTGTGTGTGTTTGTGTGTATGT GTGTGTGTGTGTGTGTGTGTGTGTGTGTAC GAAATGGGGGCTCAATGATTTGGTAGTGGT TTGGTTTGTCAAGAAGCAGGCTGGGAACTC AATAAGCATCTTTCCATTCATTTCTACTGTG TATCCCACAGCTTCACACACACATGCACAT TTCAACATTGGTGACTGCTTCACTTGCACAC CTAAGGTAATGATGGACACACCTGTAGCAA TGTAGATTCTTCCTAAGCTAATAATTAGTTT CAGGAGGTAGCACATACATTTAAAAATAGG TTAAAATAAAGTGTTATTTTAATTGGTAGGT GGATCTGTTGGCACCAATGATTATTCACGGC ATCAAGACCCAGGGTGCCCGTCAGAAGTTCT CCAGCCTCTACATCTCTCAGTTTATCATCATG TATAGTCTTGATGGGAAGAAGTGGCAGACTT ATCGAGGAAATTCCACTGGAACCTTAATG-3' | |
| | 3' homology arm 3 | 5'-GTATGTAATTAGTCATTTAAAGGGAATGCC TGAATACTTTAAAGAATTTTGGCAGATTTCAG ATATTGGACAAACACTCTTAGCTTCCACAAA CTTAATTCCAAAAAATAATTTTTCACTTATGA GCAATAGAGTTATTACGGACATATCAGCAAA AATGTAGTAGTGTCAAGGCTCATAGATGATA GAAATGAAGAGATGCTGTATTGATAGAAATA TGTGATTCAGGACTGTGTGGATTGATGATTGT GAGCTTGCTTATGGATATCCTAGGTTTGAGGT TATAGTAGGACAATCAGGTTGAAATGTCCAG CAGGCAGTAGGTGAAAGACAAGTTTAGGGG GCAAAACCATGGATGGAGATGAAGATTCATG ACTTCCACATAAAAGGATGGGTGAAACTTTG GGAATTGATGAATTCTCTAGAGGTGAGCTCA AGACCCTTAAAGGCTTAAAACCTCAGCGTTA TTGTCTACTCTTCCCTCATTITTATGCCCACA AATCTGGTCAATCCTTTATTTGCAATGCCTC TCACATCTCTTTCTTCTGTTTCCATTTATACC GCTGTTGCCACAGCCCAGGGTCCCATCACCT | 6 |

TABLE 2-continued

Homology Pairs for correction of I22I inversion

| Name | Target region | Sequence | SEQ. ID NO |
|---|---|---|---|
| | | CACACTTGATCTATTGTATTACATTCCTAACT<br>AGTCTTCCCCCGTTTCTAATCTGTTCTCCGAT<br>AAAAGCTGCACATCATTTTCAGGATAATCAT<br>CAGTCGCCTGCCTAAAACTTTTCAATGTCTT<br>CCCATTGTCTTTAGAATAAAGTTCAAAGTCT<br>TCAAATGACCCCAAGCAAGATAACTTTTGTT<br>TGCCCCTTTAGATCCATTT-3' | |
| Homology Pair 4 | 5' homology arm 4 | 5'-TTGATCCTAGGACTCCAGGATCACGCCCTG<br>GGCCAAAGGCAGACGCTAAACCGCTGAGC<br>CACCCAGGCGTCCCCAAACCTTTGTTATAA<br>ACACCACGTTAGGTGACCCAGATTCACTGC<br>CGTGAGGGTCTCAGTGTAACAGGGACAGCA<br>GATGAGCAAAGACAGCTCTCCAATGTGGTG<br>CAGTAAGATGCTCTGATGCGCTCACATACG<br>AAATGAGGCAGAGACAGAGAAAGCCGCAC<br>TGAACTTGTCTGGGTGAGTCACGAAAGGCG<br>AACCAGGAGAAATAGCTTCTGAACTGACAC<br>TTGAAAGAGGGACAGCGGTTTATCATTGGC<br>AGTGATGTTGGGATGGGCGCTGGGCTGGGG<br>AGAGCGCGGGAAGTGGCTTGGCCGAGGCCG<br>AGGCTGAGGTTGGGCAAGGCACGAGGTTCC<br>GTGGCCCCTTGTGTGCAGCACATTGCTTTGA<br>GTGTCCCCTGGTTTGTGGGGAACTAGGCGGG<br>GAACCTAATAAGCACCTTTGCTTTTTGTTCCC<br>ATCACTCATCTCAGCGCCTCACACACACCCA<br>AGGTACTCCTGAGAATACCCGTCTTGATGCA<br>GGTCCTTCTCAAGCCAACAAGTAACCTCAGA<br>AGGTGGTACATTTACATGAAGTGTTGCTTTC<br>ATTGGCAGGTGGATCTCTTGGCACCGATGAT<br>TATTCACGGCATCATGACCCAGGGGGCCCGC<br>CAGAAGTTCTCCAGCCTCTACGTGTCTCAGTT<br>TATCATCATGTACAGTCTGGATGGCAACAAG<br>TGGCACAGTTACCGAGGGAATTCCACGGGGA<br>CCTTAATG-3' | 7 |
| | 3' homology arm 4 | 5'-GTATGTCATTAGTTCTTCTTTCAAGAGAATG<br>CATGAATCTTTTAAAGAGCTTTTGACAAAGA<br>TTTCAAATTCGGGACAGACACTCCTAGCTTC<br>TACGAGCTTAATTCTAAGAAAAGATTTTTCC<br>ACTTATGGGCAGTAGGAGTGATTGTGAACAT<br>ATGGACCAAAGGTAGGAGCATCAAAGATCT<br>CATAGATAACAGACATGAAGAGGTGCTCTGT<br>AGGCAGAGATAGGTGACGAGGACTCCATGGA<br>TGGATGACATTCGTTTGACGTGATGGCAGGG<br>CAATCAAGTCACATGTCCAGCAAACCGTCAA<br>TCACAGACTTGAGTTTAGGGGGGCAAATCAT<br>GAATGCAGGTTGAAGATTCCCGTCTTCCACAT<br>AAAGCGTTGGCTGAGACCTTGGGAAAGGGTC<br>ACAAGACCCTAAATTCAACAGGCTTGCAACCT<br>TAGCATCATTGTGTACCCTTCCCTCGTGTTCGT<br>GCCTCCTGCTGAATTGGTCCACACACCCCGCA<br>ATCCTCTCCTGTCTCTTCTGTGTCACCGCTACG<br>GCTGTTACTGTTTATTGCCTGAGGCCCGTCAAC<br>TCACATTCATCTACTCCGTTACATTCCTAACTA<br>GTTGTCTCCTGTTTCTAGTCTCCTCTCTGATAAA<br>AACTTTTTGGGGAGAATCATCTTATCAGCCCTG<br>TGCCTACAACCTTCCAGTGTCTGCCTCTCTCTT<br>CAGAACAAAGTTAAAAAAATCCTCCAGCGGC<br>TCCAGGCAAAATAACTCATTTTCCCCTTCAGA<br>TGCATTGCCCTGCTTCTGGTTCTGTGAGTCTGA<br>CTTAC-3' | 8 |
| Homology Pair 5 | 5' homology arm 5 | 5'-TTGATCCTAGGACTCCAGGATCACGCCCTG<br>GGCCAAAGGCAGACGCTAAACCGCTGAGCC<br>ACCCAGGCGTCCCCAAACCTTTGTTATAAAC<br>ACCACGTTAGGTGACCCAGATTCACTGCCGT<br>GAGGGTCTCAGTGTAACAGGGACAGCAGAT<br>GAGCAAAGACAGCTCTCCAATGTGGTGCAGT<br>AAGATGCTCTGATGCGCTCACATACGAAATG<br>AGGCAGAGACAGAGAAAGCCGCACTGAACTT<br>GTCTGGGTGAGTCACGAAAGGCGAACCAGGA<br>GAAATAGCTTCTGAACTGACACTTGAAAGAG<br>GGACAGCGGTTTATCATTGGCAGTGATGTTGG<br>GATGGGCGCTGGGCTGGGGAGAGCGCGGGAA<br>GTGGCTTGGCCGAGGCCGAGGCTGAGGTTGGG | 9 |

TABLE 2-continued

Homology Pairs for correction of I22I inversion

| Name | Target region | Sequence | SEQ. ID NO |
|---|---|---|---|
| | | CAAGGCACGAGGTTCCGTGGCCCCTTGTGTGC AGCACATTGCTTTGAGTGTCCCCTGGTTTGTGG GGAACTAGGCGGGGAACCTAATAAGCACCTTT GCTTTTTGTTCCCATCACTCATCTCAGCGCCTC ACACACACCCAAGGTACTCCTGAGAATACCCG TCTTGATGCAGGTCCTTCTCAAGCCAACAAGTA ACCTCAGAAGGTGGTACATTTACATGAAGTGTT GCTTTCATTGGCAG-3' | |
| | 3' homology arm 5 | 5'-GTATGTCATTAGTTCTTCTTTCAAGAGAATG CATGAATCTTTTAAAGAGCTTTTGACAAAGA TTTCAAATTCGGGACAGACACTCCTAGCTTC TACGAGCTTAATTCTAAGAAAAGATTTTTCC ACTTATGGGCAGTAGGAGTGATTGTGAACAT ATGGACCAAAGGTAGGAGCATCAAAGATCT CATAGATAACAGACATGAAGAGGTGCTCTGT AGGCAGAGATAGGTGACGAGGACTCCATGGA TGGATGACATTCGTTTGACGTGATGGCAGGG CAATCAAGTCACATGTCCAGCAAACCGTCAAT CACAGACTTGAGTTTAGGGGGGCAAATCATG AATGCAGGTTGAAGATTCCCGTCTTCCACATA AAGCGTTGGCTGAGACCTTGGGAAAGGGTCAC AAGACCCTAAATTCAACAGGCTTGCAACCTTA GCATCATTGTGTACCCTTCCCTCGTGTTCGTGC CTCCTGCTGAATTGGTCCACACACCCCGCAATC CTCTCCTGTCTCTTCTGTGTCACCGCTACGGCTG TTACTGTTTATTGCCTGAGGCCCGTCAACTCAC ATTCATCTACTCCGTTACATTCCTAACTAGTTGT CTCCTGTTTCTAGTCTCCTCTCTGATAAAAACTT TTTGGGGAGAATCATCTTATCAGCCCTGTGCCTA CAACCTTCCAGTGTCTGCCTCTCTCTTCAGAACA AAGTTAAAAAAATCCTCCAGCGGCTCCAGGCAA AATAACTCATTTTCCCCTTCAGATGCATTGCCCT GCTTCTGGTTCTGTGAGTCTGACTTAC-3' | 10 |
| Homology Pair 6 | 5' homology arm 6 | 5'-TTGATCCTAGGACTCCAGGATCACGCCCTG GGCCAAAGGCAGACGCTAAACCGCTGAGC CACCCAGGCGTCCCCAAACCTTTGTTATAA ACACCACGTTAGGTGACCCAGATTCACTGC CGTGAGGGTCTCAGTGTAACAGGGACAGCA GATGAGCAAAGACAGCTCTCCAATGTGGTG CAGTAAGATGCTCTGATGCGCTCACATACG AAATGAGGCAGAGACAGAGAAAGCCGCAC TGAACTTGTCTGGGTGAGTCACGAAAGGCG AACCAGGAGAAATAGCTTCTGAACTGACAC TTGAAAGAGGGACAGCGGTTTATCATTGGCA GTGATGTTGGGATGGGCGCTGGGCTGGGGA GAGCGCGGGAAGTGGCTTGGCCGAGGCCGA GGCTGAGGTTGGGCAAGGCACGAGGTTCCG TGGCCCCTTGTGTGCAGCACATTGCTTTGAG TGTCCCCTGGTTTGTGGGGAACTAGGCGGGG AACCTAATAAGCACCTTTGCTTTTTGTTCCCA TCACTCATCTCAGCGCCTCACACACACCCAAG GTACTCCTGAGAATACCCGTCTTGATGCAGGT CCTTCTCAAGCCAACAAGTAACCTCAGAAGGT GGTACATTTACATGAAGTGTTGCTTTCATTGG CAG-3' | 11 |
| | 3' homology arm 6 | 5'-GTATGTCATTAGTTCTTCTTTCAAGAGAATG CATGAATCTTTTAAAGAGCTTTTGACAAAGA TTTCAAATTCGGGACAGACACTCCTAGCTTC TACGAGCTTAATTCTAAGAAAAGATTTTTCC ACTTATGGGCAGTAGGAGTGATTGTGAACA TATGGACCAAAGGTAGGAGCATCAAAGAT CTCATAGATAACAGACATGAAGAGGTGCTC TGTAGGCAGAGATAGGTGACGAGGACTCCA TGGATGGATGACATTCGTTTGACGTGATGGC AGGGCAATCAAGTCACATGTCCAGCAAACC GTCAATCACAGACTTGAGTTTAGGGGGGCAA ATCATGAATGCAGGTTGAAGATTCCCGTCTT CCACATAAAGCGTTGGCTGAGACCTTGGGA AAGGGTCACAAGACCCTAAATTCAACAGGCT TGCAACCTTAGCATCATTGTGTACCCTTCCCTC GTGTTCGTGCCTCCTGCTGAATTGGTCCACAC ACCCCGCAATCCTCTCCTGTCTCTTCTGTGTCA CCGCTACGGCTGTTACTGTTTATTGCCTGAGGC CCGTCAACTCACATTCATCTACTCCGTTACATT | 12 |

TABLE 2-continued

Homology Pairs for correction of I22I inversion

| Name | Target region | Sequence | SEQ. ID NO |
|---|---|---|---|
| | | CCTAACTAGTTGTCTCCTGTTTCTAGTCTCCTCT CTGATAAAAACTTTTTGGGGAGAATCATCTTAT CAGCCCTGTGCCTACAACCTTCCAGTGTCTGCC TCTCTCTTCAGAACAAAGTTAAAAAAATCCTCC AGCGGCTCCAGGCAAAATAACTCATTTTCCCCT TCAGATGCATTGCCCTGCTTCTGGTTCTGTGAGT CTGACTTAC-3' | |
| Homology Pair 7 | 5' homology arm 7 | 5'-TTGATCCTAGGACTCCAGGATCACGCCCTG GGCCAAAGGCAGACGCTAAACCGCTGAGCC ACCCAGGCGTCCCCAAACCTTTGTTATAAA CACCACGTTAGGTGACCCAGATTCACTGCC GTGAGGGTCTCAGTGTAACAGGGACAGCAG ATGAGCAAAGACAGCTCTCCAATGTGGTGC AGTAAGATGCTCTGATGCGCTCACATACGAA ATGAGGCAGAGACAGAGAAAGCCGCACTGA ACTTGTCTGGGTGAGTCACGAAAGGCGAACC AGGAGAAATAGCTTCTGAACTGACACTTGAA AGAGGGACAGCGGTTTATCATTGGCAGTGAT GTTGGGATGGGCGCTGGGCTGGGGAGAGCGC GGGAAGTGGCTTGGCCGAGGCCGAGGCTGAG GTTGGGCAAGGCACGAGGTTCCGTGGCCCCTT GTGTGCAGCACATTGCTTTGAGTGTCCCCTGG TTTGTGGGGAACTAGGCGGGGAACCTAATAA GCACCTTTGCTTTTTGTTCCCATCACTCATCTC AGCGCCTCACACACACCCAAGGTACTCCTGA GAATACCCGTCTTGATGCAGGTCCTTCTCAAG CCAACAAGTAACCTCAGAAGGTGGTACATTTA CATGAAGTGTTGCTTTCATTGGCAG-3' | 13 |
| | 3' homology arm 7 | 5'-GTATGTCATTAGTTCTTCTTTCAAGAGAATG CATGAATCTTTTAAAGAGCTTTTGACAAAGA TTTCAAATTCGGGACAGACACTCCTAGCTTC TACGAGCTTAATTCTAAGAAAAGATTTTTCC ACTTATGGGCAGTAGGAGTGATTGTGAACAT ATGGACCAAAGGTAGGAGCATCAAAGATCT CATAGATAACAGACATGAAGAGGTGCTCTGT AGGCAGAGATAGGTGACGAGGACTCCATGGA TGGATGACATTCGTTTGACGTGATGGCAGGGC AATCAAGTCACATGTCCAGCAAACCGTCAATC ACAGACTTGAGTTTAGGGGGGCAAATCATGAA TGCAGGTTGAAGATTCCCGTCTTCCACATAAAG CGTTGGCTGAGACCTTGGGAAAGGGTCACAAG ACCCTAAATTCAACAGGCTTGCAACCTTAGCAT CATTGTGTACCCTTCCCTCGTGTTCGTGCCTCCT GCTGAATTGGTCCACACACCCCGCAATCCTCTC CTGTCTCTTCTGTGTCACCGCTACGGCTGTTACT GTTTATTGCCTGAGGCCCGTCAACTCACATTCA TCTACTCCGTTACATTCCTAACTAGTTGTCTCCT GTTTCTAGTCTCCTCTCTGATAAAAACTTTTTGG GGAGAATCATCTTATCAGCCCTGTGCCTACAAC CTTCCAGTGTCTGCCTCTCTCTTCAGAACAAAGT TAAAAAAATCCTCCAGCGGCTCCAGGCAAAATA ACTCATTTTCCCCTTCAGATGCATTGCCCTGCTT CTGGTTCTGTGAGTCTGACTTAC-3' | 14 |

TABLE 3

F8 codon optimized nucleotide sequences

| Codon optimized Insert | Sequence | SEQ. ID NO |
|---|---|---|
| Exon 23-Exon 24-Exon 25-Exon 26 (Human) | 5'-GTCTTCTTTGGGAACGTGGACTCAAGTGGAATT AAACATAACATCTTTAACCCACCCATAATCGCG CGATATATTCGGTTGCACCCGACCCATTACTCCA TCCGCTCAACACTCAGGATGGAACTGATGGGTT GTGATCTTAACTCATGTTCTATGCCTCTGGGTAT GGAGTCAAAGGCAATTAGTGATGCGCAGATTAC TGCTTCTTCTTACTTTACCAATATGTTCGCAACGT GGTCACCATCCAAAGCTCGGTTGCATCTTCAGGG AAGGTCAAACGCGTGGCGGCCCCAGGTCAACAAT | 15 |

TABLE 3-continued

| F8 codon optimized nucleotide sequences | | |
|---|---|---|
| Codon optimized Insert | Sequence | SEQ. ID NO |
| | CCTAAAGAGTGGTTGCAAGTTGACTTTCAAAAGAC TATGAAAGTGACAGGGGTCACGACTCAAGGCGTG AAGTCATTGCTCACTTCAATGTACGTTAAAGAATT CCTCATTAGCAGTTCACAGGATGGGCATCAGTGGA CTCTTTTCTTCCAAAATGGGAAAGTGAAGGTTTTTC AAGGTAATCAAGACAGTTTCACTCCGGTAGTCAAT AGTTTGGACCCCCCTCTTTTGACTAGATACCTGCGG ATTCACCCCCAGAGCTGGGTTCACCAAATTGCTCTG AGAATGGAGGTTCTGGGATGCGAAGCTCAAGACCT GTAC-3' | |
| Exon 23-Exon 24-Exon 25-Exon 26 (Canine) (Pair 4) | 5'-GTCTTCTTTGGTAACGTCGATTCTTCTGGGATCAA ACACAATATATTTAATCCTCCCATAATCGCACAATA CATTCGGCTCCACCCAACTCATTACTCCATTAGGTC TACCTTGAGGATGGAGTTGCTCGGATGCGACTTCAA CTCTTGCAGTATGCCGCTTGGAATGGAATCTAAAGC GATAAGCGATGCGCAAATTACTGCGTCCTCTTATCT TAGCTCTATGCTCGCTACCTGGTCCCCATCTCAGGC ACGATTGCATCTCCAAGGAAGAACGAACGCTTGGA GGCCGCAAGCGAATAACCCAAAAGAATGGCTTCAA GTCGATTTCAGGAAAACAATGAAGGTCACCGGCAT AACGACGCAGGGTGTTAAAAGTTTGTTGATAAGCAT GTATGTGAAGGAATTTCTTATCAGCAGCAGTCAGGA TGGTCACAACTGGACCCTTTTCCTCCAAAATGACAA AGTCAAAGTTTTCCAAGGCAACAGAGACAGTTCTAC TCCCGTGAGGAATGCGCTGGAACCCCCACTGGTGGC TCGCTACGTCAGATTGCATCCACAAAGCTGGGCTCA CCATATAGCTCTTCGCTTGGAGGTGCTTGGATGCGAT ACTCAGCAGCCGGCC-3' | 16 |
| Exon 23-Exon 24-Exon 25-Exon 26 (Canine) (Pair 7) | 5'-GTCTTCTTTGGTAACGTCGATTCTTCTGGGATCAA ACACAATATATTTAATCCTCCCATAATCGCACAAT ACATTCGGCTCCACCCAACTCATTACTCCATTAGG TCTACCTTGAGGATGGAGTTGCTCGGATGCGACTT CAACTCTTGCAGTATGCCGCTTGGAATGGAATCTA AAGCGATAAGCGATGCGCAAATTACTGCGTCCTCT TATCTTAGCTCTATGCTCGCTACCTGGTCCCCATCT CAGGCACGATTGCATCTCCAAGGAAGAACGAACG CTTGGAGGCCGCAAGCGAATAACCCAAAAGAATG GCTTCAAGTCGATTTCAGGAAAACAATGAAGGTCA CCGGCATAACGACGCAGGGTGTTAAAAGTTTGTTG ATAAGCATGTATGTGAAGGAATTTCTTATCAGCAG CAGTCAGGATGGTCACAACTGGACCCTTTTCCTCCA AAATGACAAAGTCAAAGTTTTCCAAGGCAACAGAG ACAGTTCTACTCCCGTGAGGAATGCGCTGGAACC CCCACTGGTGGCTCGCTACGTCAGATTGCATCCAC AAAGCTGGGCTCACCATATAGCTCTTCGCTTGGAG GTGCTTGGATGCGATACTCAGCAGCCGGCCTGA-3' | 17 |

TABLE 4

| Complete insertion sequence after editing in I22I patient B-LCL Cells | | |
|---|---|---|
| Name | Sequence | SEQ. ID NO |
| AAVHSC15 L800R800 transduced I22I cells | 5'-GCCCTGAACTCAGCACATTACATGTATTAACTCTT TAACCCCTATGGCAGCCCTTTGAGATAAAAACTAATA TTATCTTCACTTTACAGATAAGTTGAGACACAGAAAG TTAGGTGACTCAAATGGGTTCACTGCCTTAAGGATCT CAGTCTAATAAGGAAAGCAGAAAAGCAAAGCAACCT TATAATATGGTGCAATAATTTGCTATAATGAAGTTAT ATACAAAGTGAAGTAGAAGCATAGAAGAAGCAGCAC TAAATTTGTCTGGGTGAGTCAGAGAAGGCTAACCAGG AAAAATAGTTTCTGAACTAACACTTGAAGGAGGTGTA GCAGTTCATCACTGACAGTGATGTTGGGGTGGGTCTG GTTTCAGGAGAGGGGAGGAAATTGGCTTTGGTCTGA GGCTGAGGTGTGGGCAAAGCATTAGCTTATGTGGGTC CATTAGCTTATGTGAGTCCACAAAAGGTGTGTGTGTGT TTGTGTGTATGTGTGTGTGTGTGTGTGTGTGTGTGTGT ACGAAATGGGGGCTCAATGATTTGGTAGTGGTTTGGTT | 18 |

TABLE 4-continued

Complete insertion sequence after editing in I22I patient B-LCL Cells

| Name | Sequence | SEQ. ID NO |
|---|---|---|
| | TGTCAAGAAGCAGGCTGGGAACTCAATAAGCATCTTTC | |
| | CATTCATTTCTACTGTGTATCCCACAGCTTCACACACACA | |
| | TGCACATTTCAACATTGGTGACTGCTTCACTTGCACACC | |
| | TAAGGTAATGATGGACACACCTGTAGCAATGTAGATTC | |
| | TTCCTAAGCTAATAATTAGTTTCAGGAGGTAGCACATA | |
| | CATTTAAAAATAGGTTAAAATAAAGTGTTATTTTAATTG | |
| | GTAGGTGGATCTGTTGGCACCAATGATTATTCACGGCA | |
| | TCAAGACCCAGGGTGCCCGTCAGAAGTTCTCCAGCCTC | |
| | TACATCTCTCAGTTTATCATCATGTATAGTCTTGATGGG | |
| | AAGAAGTGGCAGACTTATCGAGGAAATTCCACTGGA | |
| | ACCTTAATGGTCTTCTTTGGGAACGTGGACTCAAGTGG | |
| | AATTAAACATAACATCTTTAACCCACCCATAATCGCGC | |
| | GATATATTCGGTTGCACCCGACCCATTACTCCATCCGC | |
| | TCAACACTCAGGATGGAACTGATGGGTTGTGATCTTAA | |
| | CTCATGTTCTATGCCTCTGGGTATGGAGTCAAAGGCAA | |
| | TTAGTGATGCGCAGATTACTGCTTCTTCTTACTTTACCA | |
| | ATATGTTCGCAACGTGGTCACCATCCAAAGCTCGGTTG | |
| | CATCTTCAGGGAAGGTCAAACGCGTGGCGGCCCCAG | |
| | GTCAACAATCCTAAAGAGTGGTTGCAAGTTGACTTTCA | |
| | AAAGACTATGAAAGTGACAGGGGTCACGACTCAAGG | |
| | CGTGAAGTCATTGCTCACTTCAATGTACGTTAAAGAAT | |
| | TCCTCATTAGCAGTTCACAGGATGGGCATCAGTGGACT | |
| | CTTTTCTTCCAAAATGGGAAAGTGAAGGTTTTTCAAG | |
| | GTAATCAAGACAGTTTCACTCCGGTAGTCAATAGTTT | |
| | GGACCCCCCTCTTTTGACTAGATACCTGCGGATTCACC | |
| | CCCAGAGCTGGGTTCACCAAATTGCTCTGAGAATGGA | |
| | GGTTCTGGGATGCGAAGCTCAAGACCTGTACGCGGCC | |
| | GCCGACTACAAAGACCATGACGGTGATTATAAAGATC | |
| | ATGACATCGATTACAAGGATGACGATGACAAGGCGGC | |
| | CGCCGGCAGCGGAGAGGGCAGAGGAAGTCTTCTAAC | |
| | ATGCGGTGACGTGGAGGAGAATCCCGGCCCTAGGGGT | |
| | ACCATGGTGAGCAAGGGCGAGGAGGATAACATGGCCA | |
| | TCATCAAGGAGTTCATGCGCTTCAAGGTGCACATGGAG | |
| | GGCTCCGTGAACGGCCACGAGTTCGAGATCGAGGGCG | |
| | AGGGCGAGGGCCGCCCCTACGAGGGCACCCAGACCGC | |
| | CAAGCTGAAGGTGACCAAGGGTGGCCCCCTGCCCTTCG | |
| | CCTGGGACATCCTGTCCCCTCAGTTCATGTACGGCTCCA | |
| | AGGCCTACGTGAAGCACCCCGCCGACATCCCCGACTAC | |
| | TTGAAGCTGTCCTTCCCCGAGGGCTTCAAGTGGGAGCG | |
| | CGTGATGAACTTCGAGGACGGCGGCGTGGTGACCGTG | |
| | ACCCAGGACTCCTCCCTGCAGGACGGCGAGTTCATCTA | |
| | CAAGGTGAAGCTGCGCGGCACCAACTTCCCCTCCGACG | |
| | GCCCCGTAATGCAGAAGAAGACCATGGGCTGGGAGGC | |
| | CTCCTCCGAGCGGATGTACCCCGAGGACGGCGCCCTG | |
| | AAGGGCGAGATCAAGCAGAGGCTGAAGCTGAAGGAC | |
| | GGCGGCCACTACGACGCTGAGGTCAAGACCACCTACA | |
| | AGGCCAAGAAGCCCGTGCAGCTGCCCGGCGCCTACAA | |
| | CGTCAACATCAAGTTGGACATCACCTCCCACAACGAGG | |
| | ACTACACCATCGTGGAACAGTACGAACGCGCCGAGGG | |
| | CCGCCACTCCACCGGCGGCATGGACGAGCTGTACAAG | |
| | TAACTCGAGCCTCTAGAACTATAGTGAGTCGTATTAC | |
| | GTAGATCCAGACATGATAAGATACATTGATGAGTTT | |
| | GGACAAACCACAACTAGAATGCAGTGAAAAAAATGC | |
| | TTTATTTGTGAAATTTGTGATGCTATTGCTTTATTTGT | |
| | AACCATTATAAGCTGCAATAAACAAGTTAACAACAA | |
| | CAATTGCATTCATTTTATGTTTCAGGTTCAGGGGGA | |
| | GGTGTGGGAGGTTTTTTAAAAAGCTTTACGTATGTA | |
| | ATTAGTCATTTAAAGGGAATGCCTGAATACTTTAAA | |
| | GAATTTTGGCAGATTTCAGATATTGGACAAACACTCT | |
| | TAGCTTCCACAAACTTAATTCCAAAAAATAATTTTTC | |
| | ACTTATGAGCAATAGAGTTATTACGGACATATCAGC | |
| | AAAAATGTAGTAGTGTCAAGGCTCATAGATGATAGA | |
| | AATGAAGAGATGCTGTATTGATAGAAATATGTGATT | |
| | CAGGACTGTGTGGATTGATGATTGTGAGCTTGCTTAT | |
| | GGATATCCTAGGTTTGAGGTTATAGTAGGACAATCA | |
| | GGTTGAAATGTCCAGCAGGCAGTAGGTGAAAGACA | |
| | AGTTTAGGGGGCAAAACCATGGATGGAGATGAAGAT | |
| | TCATGACTTCCACATAAAAGGATGGGTGAAACTTTGG | |
| | GAATTGATGAATTCTCTAGAGGTGAGCTCAAGACCCT | |
| | TAAAGGCTTAAAACCTCAGCGTTATTGTCTACTCTTCC | |
| | CTCATTTTTATGCCCACAAATCTGGTCAATCCTTTATTT | |
| | GCAATGCCTCTCACATCTCTTTCTTCTGTTTCCATTTATA | |
| | CCGCTGTTGCCACAGCCCAGGGTCCCATCACCTCACAC | |
| | TTGATCTATTGTATTACATTCCTAACTAGTCTTCCCCCG | |
| | TTTCTAATCTGTTCTCCGATAAAAGCTGCACATCATTTT | |

TABLE 4-continued

Complete insertion sequence after editing in I22I patient B-LCL Cells

| Name | Sequence | SEQ. ID NO |
|---|---|---|
| | CAGGATAATCATCAGTCGCCTGCCTAAAACTTTTCAAT GTCTTCCCATTGTCTTTAGAATAAAGTTCAAAGTCTTCA AATGACCCCAAGCAAGATAACTTTTGTTTGCCCCTTTA GATCCATTTTCCTGCTTCTCTACCCTGCTTCTTGTTCTG TGAGGTGAGCTTGTATAGAATACATCAACAGGTTACC TTGTCCTCCAGCTTTTGGTTGGATTTCACCAACAGGGA GCACTGGCAAAAGATTGGCATATTTATTCTTCTGACTT TCTCCTTGCAGAGGAGTTCACTGTATCTCCCCACTTAA GGTCACTGTT-3' | |
| FVIII intron 21 sequence external to the left Homology Arm | 5'-GCCCTGAACTCAGCACATTACATGTATTAACTCTTTAACCCCT ATGGCAGCCCTTTGAGATAAAAACTAATATTATCTTCACTTTACA GATAAGTTGAGACACAGAAAGTTAGGTGACTCAAATGGGTTCA CTGCCTTAAGGATCT-3' | 19 |
| HAL (Homology Arm Left Sequence from FVIII intron 21 and exon 22) | 5'-CAGTCTAATAAGGAAAGCAGAAAAGCAAAGCAACCTTATAAT ATGGTGCAATAATTTGCTATAATGAAGTTATATACAAAGTGAAG TAGAAGCATAGAAGAAGCAGCACTAAATTTGTCTGGGTGAGTC AGAGAAGGCTAACCAGGAAAAATAGTTTCTGAACTAACACTTG AAGGAGGTGTAGCAGTTCATCACTGACAGTGATGTTGGGGTG GGTCTGGTTTCAGGAGAGGGGAGGAAATTGGCTTTGGTCTGA GGCTGAGGTGTGGGCAAAGCATTAGCTTATGTGGGTCCATTA GCTTATGTGAGTCCACAAAAGGTGTGTGTGTGTTTGTGTGTAT GTGTGTGTGTGTGTGTGTGTGTGTGTGTACGAAATGGGGGCT CAATGATTTGGTAGTGGTTTGGTTTGTCAAGAAGCAGGCTGG GAACTCAATAAGCATCTTTCCATTCATTTCTACTGTGTATCCCA CAGCTTCACACACACATGCACATTTCAACATTGGTGACTGCTT CACTTGCACACCTAAGGTAATGATGGACACACCTGTAGCAAT GTAGATTCTTCCTAAGCTAATAATTAGTTTCAGGAGGTAGCA CATACATTTAAAAATAGGTTAAAATAAAGTGTTATTTTAATTG GTAGGTGGATCTGTTGGCACCAATGATTATTCACGGCATCAA GACCCAGGGTGCCCGTCAGAAGTTCTCCAGCCTCTACATCTC TCAGTTTATCATCATGTATAGTCTTGATGGGAAGAAGTGGC AGACTTATCGAGGAAATTCCACTGGAACCTTAATG-3' | 20 |
| Codon optimized exon 23-26 sequence | 5'-GTCTTCTTTGGGAACGTGGACTCAAGTGGAATTAAACA TAACATCTTTAACCCACCCATAATCGCGCGATATATTCGGT TGCACCCGACCCATTACTCCATCCGCTCAACACTCAGGAT GGAACTGATGGGTTGTGATCTTAACTCATGTTCTATGCCT CTGGGTATGGAGTCAAAGGCAATTAGTGATGCGCAGATT ACTGCTTCTTCTTACTTTACCAATATGTTCGCAACGTGGTC ACCATCCAAAGCTCGGTTGCATCTTCAGGGAAGGTCAAAC GCGTGGCGGCCCCAGGTCAACAATCCTAAAGAGTGGTTG CAAGTTGACTTTCAAAAGACTATGAAAGTGACAGGGGTCA CGACTCAAGGCGTGAAGTCATTGCTCACTTCAATGTACG TTAAAGAATTCCTCATTAGCAGTTCACAGGATGGGCATCA GTGGACTCTTTTCTTCCAAAATGGGAAAGTGAAGGTTTTT CAAGGTAATCAAGACAGTTTCACTCCGGTAGTCAATAGTT TGGACCCCCCTCTTTTGACTAGATACCTGCGGATTCACCCC CAGAGCTGGGTTCACCAAATTGCTCTGAGAATGGAGGTTC TGGGATGCGAAGCTCAAGACCTGTA-3' | 21 |
| Junction between HAL and codon optimized Exon23-26 | 5'-AACCTTAATGGTCTTCTTTG-3' | 22 |
| 3X Flag sequence | 5'-GACTACAAAGACCATGACGGTGATTATAAAGATCATGA CATCGATTACAAGGATGACGATGACAAG-3' | 23 |
| T2A-mCherry-PA reporter cassette | 5'-GGCAGCGGAGAGGGCAGAGGAAGTCTTCTAACATGCGG TGACGTGGAGGAGAATCCCGGCCCTAGGGGTACCATGGTG AGCAAGGGCGAGGAGGATAACATGGCCATCATCAAGGAGT TCATGCGCTTCAAGGTGCACATGGAGGGCTCCGTGAACGGC CACGAGTTCGAGATCGAGGGCGAGGGCGAGGGCCGCCCCT ACGAGGGCACCCAGACCGCCAAGCTGAAGGTGACCAAGGG TGGCCCCCTGCCCTTCGCCTGGGACATCCTGTCCCCTCAGTTC ATGTACGGCTCCAAGGCCTACGTGAAGCACCCCGCCGACATC CCCGACTACTTGAAGCTGTCCTTCCCCGAGGGCTTCAAGTGG GAGCGCGTGATGAACTTCGAGGACGGCGGCGTGGTGACCGT GACCCAGGACTCCTCCCTGCAGGACGGCGAGTTCATCTACAA GGTGAAGCTGCGCGGCACCAACTTCCCCTCCGACGGCCCCGT AATGCAGAAGAAGACCATGGGCTGGGAGGCCTCCTCCGAGC GGATGTACCCCGAGGACGGCGCCCTGAAGGGCGAGATCAAG CAGAGGCTGAAGCTGAAGGACGGCGGCCACTACGACGCTGA | 24 |

TABLE 4-continued

Complete insertion sequence after editing in I22I patient B-LCL Cells

| Name | Sequence | SEQ. ID NO |
|---|---|---|
| | GGTCAAGACCACCTACAAGGCCAAGAAGCCCGTGCAGCTGCC CGGCGCCTACAACGTCAACATCAAGTTGGACATCACCTCCCAC AACGAGGACTACACCATCGTGGAACAGTACGAACGCGCCGAG GGCCGCCACTCCACCGGCGGCATGGACGAGCTGTACAAGTAA CTCGAGCCTCTAGAACTATAGTGAGTCGTATTACGTAGATCCA GACATGATAAGATACATTGATGAGTTTGGACAAACCACAACTA GAATGCAGTGAAAAAAATGCTTTATTTGTGAAATTTGTGATGCT ATTGCTTTATTTGTAACCATTATAAGCTGCAATAAACAAGTTAA CAACAACAATTGCATTCATTTTATGTTTCAGGTTCAGGGGGAGG TGTGGGAGGTTTTTTAAAAAGCTTTAC-3' | |
| HAR (Homology Arm Right Sequence from FVIII intron 22) | 5'-GTATGTAATTAGTCATTTAAAGGGAATGCCTGAATACTTTA AAGAATTTTGGCAGATTTCAGATATTGGACAAACACTCTTAGC TTCCACAAACTTAATTCCAAAAAATAATTTTTCACTTATGAGCA ATAGAGTTATTACGGACATATCAGCAAAAATGTAGTAGTGTC AAGGCTCATAGATGATAGAAATGAAGAGATGCTGTATTGATA GAAATATGTGATTCAGGACTGTGTGGATTGATGATTGTGAGC TTGCTTATGGATATCCTAGGTTTGAGGTTATAGTAGGACAAT CAGGTTGAAATGTCCAGCAGGCAGTAGGTGAAAGACAAG TTTAGGGGGCAAAACCATGGATGGAGATGAAGATTCATGA CTTCCACATAAAAGGATGGGTGAAACTTTGGGAATTGATGA ATTCTCTAGAGGTGAGCTCAAGACCCTTAAAGGCTTAAAACC TCAGCGTTATTGTCTACTCTTCCCTCATTTTTATGCCCACAAAT CTGGTCAATCCTTTATTTGCAATGCCTCTCACATCTCTTTCTTC TGTTTCCATTTATACCGCTGTTGCCACAGCCCAGGGTCCCATC ACCTCACACTTGATCTATTGTATTACATTCCTAACTAGTCTTCC CCCGTTTCTAATCTGTTCTCCGATAAAAGCTGCACATCATTTTC AGGATAATCATCAGTCGCCTGCCTAAAACTTTTCAATGTCTTC CCATTGTCTTTAGAATAAAGTTCAAAGTCTTCAAATGACCCCA AGCAAGATAACTTTTGTTTGCCCCTTTAGATCCATTTT-3' | 25 |
| FVIII Intron 22 sequence external to the Right Homology Arm | 5'-CCTGCTTCTCTACCCTGCTTCTTGTTCTGTGAGGTGAGCT TGTATAGAATACATCAACAGGTTACCTTGTCCTCCAGCTTTT GGTTGGATTTCACCAACAGGGAGCACTGGCAAAAGATTGG CATATTTATTCTTCTGACTTTCTCCTTGCAGAGGAGTTCACT GTATCTCCCCACTTAAGGTCACTGTT-3' | 26 |

What is claimed is:

1. A method for correcting a mutation in an F8 gene in a cell, the method comprising transducing the cell with a replication-defective adeno-associated virus (AAV) comprising:

a) an AAV capsid; and b) a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus;

wherein:

(A) the 5' homology arm consists of the nucleotide sequence set forth in SEQ. ID NO: 1 and the 3' homology arm consists of the nucleotide sequence set forth in SEQ. ID NO: 2; or (B) the 5' homology arm consists of the nucleotide sequence set forth in SEQ. ID NO: 3 and the 3' homology arm consists of the nucleotide sequence set forth in SEQ. ID NO: 4; or (C) the 5' homology arm consists of the nucleotide sequence set forth in SEQ. ID NO: 5 and the 3' homology arm consists of the nucleotide sequence set forth in SEQ. ID NO: 6; or (D) the 5' homology arm consists of the nucleotide sequence set forth in SEQ. ID NO: 7 and the 3' homology arm consists of the nucleotide sequence set forth in SEQ. ID NO: 8; or (E) the 5' homology arm consists of the nucleotide sequence set forth in SEQ. ID NO: 9 and the 3' homology arm consists of the nucleotide sequence set forth in SEQ. ID NO: 10; or (F) the 5' homology arm consists of the nucleotide sequence set forth in SEQ. ID NO: 11 and the 3' homology arm consists of the nucleotide sequence set forth in SEQ. ID NO: 12; or (G) the 5' homology arm consists of the nucleotide sequence set forth in SEQ. ID NO: 13 and the 3' homology arm consists of the nucleotide sequence set forth in SEQ. ID NO: 14; and, wherein the cell is transduced without co-transducing or co-administering an exogenous nuclease or a nucleotide sequence that encodes an exogenous nuclease.

2. The method of claim 1, wherein the mutation is an I22I inversion.

3. The method of claim 1, wherein the AAV capsid is an AAVHSC capsid.

4. The method of claim 1, wherein the correction genome further comprises an F8 coding sequence.

5. The method of claim 4, wherein the F8 coding sequence is silently altered.

6. The method of claim 4, wherein the F8 coding sequence consists of the nucleotide sequences set forth in SEQ. ID NOS: 15, 16, or 17.

7. A method for treating a subject having a disease or disorder associated with a mutation in an F8 gene, the method comprising administering to the subject an effective amount of a replication-defective recombinant adeno-associated virus (AAV) comprising:

a) an AAV capsid; and b) a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus;

wherein:

(A) the 5' homology arm consists of the nucleotide sequence set forth in SEQ. ID NO: 1 and the 3' homology arm consists of the nucleotide sequence set forth in SEQ. ID NO: 2; or (B) the 5' homology arm consists of the nucleotide sequence set forth in SEQ. ID NO: 3 and the 3' homology arm consists of the nucleotide sequence set forth in SEQ. ID NO: 4; or (C) the 5' homology arm consists of the nucleotide sequence set forth in SEQ. ID NO: 5 and the 3' homology arm consists of the nucleotide sequence set forth in SEQ. ID NO: 6; or (D) the 5' homology arm consists of the nucleotide sequence set forth in SEQ. ID NO: 7 and the 3' homology arm consists of the nucleotide sequence set forth in SEQ. ID NO: 8; or (E) the 5' homology arm consists of the nucleotide sequence set forth in SEQ. ID NO: 9 and the 3' homology arm consists of the nucleotide sequence set forth in SEQ. ID NO: 10; or (F) the 5' homology arm consists of the nucleotide sequence set forth in SEQ. ID NO: 11 and the 3' homology arm consists of the nucleotide sequence set forth in SEQ. ID NO: 12; or (G) the 5' homology arm consists of the nucleotide sequence set forth in SEQ. ID NO: 13 and the 3' homology arm consists of the nucleotide sequence set forth in SEQ. ID NO: 14; and, wherein an exogenous nuclease or a nucleotide sequence that encodes an exogenous nuclease is not co-administered to the subject.

8. The method of claim 7, wherein the mutation is an I22I inversion.

9. The method of claim 7, wherein the AAV capsid is an AAVHSC capsid.

10. The method of claim 7, wherein the correction genome further comprises an F8 coding sequence.

11. The method of claim 7, wherein the disease or disorder is associated with blood coagulation.

12. The method of claim 7, wherein the disease or disorder is hemophilia A.

13. A replication-defective adeno-associated virus (AAV) comprising:

a) an AAV capsid; and b) a correction genome comprising: (i) an editing element for editing a target locus in the F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus;

wherein:

(A) the 5' homology arm consists of the nucleotide sequence set forth in SEQ. ID NO: 1 and the 3' homology arm consists of the nucleotide sequence set forth in SEQ. ID NO: 2; or (B) the 5' homology arm consists of the nucleotide sequence set forth in SEQ. ID NO: 3 and the 3' homology arm consists of the nucleotide sequence set forth in SEQ. ID NO: 4; or (C) the 5' homology arm consists of the nucleotide sequence set forth in SEQ. ID NO: 5 and the 3' homology arm consists of the nucleotide sequence set forth in SEQ. ID NO: 6; or (D) the 5' homology arm consists of the nucleotide sequence set forth in SEQ. ID NO: 7 and the 3' homology arm consists of the nucleotide sequence set forth in SEQ. ID NO: 8; or (E) the 5' homology arm consists of the nucleotide sequence set forth in SEQ. ID NO: 9 and the 3' homology arm consists of the nucleotide sequence set forth in SEQ. ID NO: 10; or (F) the 5' homology arm consists of the nucleotide sequence set forth in SEQ. ID NO: 11 and the 3' homology arm consists of the nucleotide sequence set forth in SEQ. ID NO: 12; or (G) the 5' homology arm consists of the nucleotide sequence set forth in SEQ. ID NO: 13 and the 3' homology arm consists of the nucleotide sequence set forth in SEQ. ID NO: 14.

14. A nucleic acid comprising:

(i) an editing element for editing a target locus in an F8 gene; (ii) a 5' homology arm nucleotide sequence 5' to the editing element having homology to a first genomic region 5' to the target locus; and (iii) a 3' homology arm nucleotide sequence 3' to the editing element having homology to a second genomic region 3' to the target locus;

wherein:

(A) the 5' homology arm consists of the nucleotide sequence set forth in SEQ. ID NO: 1 and the 3' homology arm consists of the nucleotide sequence set forth in SEQ. ID NO: 2; or (B) the 5' homology arm consists of the nucleotide sequence set forth in SEQ. ID NO: 3 and the 3' homology arm consists of the nucleotide sequence set forth in SEQ. ID NO: 4; or (C) the 5' homology arm consists of the nucleotide sequence set forth in SEQ. ID NO: 5 and the 3' homology arm consists of the nucleotide sequence set forth in SEQ. ID NO: 6; or (D) the 5' homology arm consists of the nucleotide sequence set forth in SEQ. ID NO: 7 and the 3' homology arm consists of the nucleotide sequence set forth in SEQ. ID NO: 8; or (E) the 5' homology arm consists of the nucleotide sequence set forth in SEQ. ID NO: 9 and the 3' homology arm consists of the nucleotide sequence set forth in SEQ. ID NO: 10; or (F) the 5' homology arm consists of the nucleotide sequence set forth in SEQ. ID NO: 11 and the 3' homology arm consists of the nucleotide sequence set forth in SEQ. ID NO: 12; or (G) the 5' homology arm consists of the nucleotide sequence set forth in SEQ. ID NO: 13 and the 3' homology arm consists of the nucleotide sequence set forth in SEQ. ID NO: 14.

* * * * *

SEQUENCE LISTING

<160> NUMBER OF SEQ ID NOS: 26

<210> SEQ ID NO 1
<211> LENGTH: 219
<212> TYPE: DNA
<213> ORGANISM: Artificial Sequence
<220> FEATURE:
<223> OTHER INFORMATION: Synthetic Polynucleotide

<400> SEQUENCE: 1
gtttcaggag gtagcacata catttaaaaa taggttaaaa taaagtgtta ttttaattgg 60
taggtggatc tgttggcacc aatgattatt cacggcatca agacccaggg tgcccgtcag 120
aagttctcca gcctctacat ctctcagttt atcatcatgt atagtcttga tgggaagaag 180
tggcagactt atcgaggaaa ttccactgga accttaatg 219

<210> SEQ ID NO 2
<211> LENGTH: 799
<212> TYPE: DNA
<213> ORGANISM: Artificial Sequence
<220> FEATURE:
<223> OTHER INFORMATION: Synthetic Polynucleotide

<400> SEQUENCE: 2
gtatgtaatt agtcatttaa agggaatgcc tgaatacttt aaagaatttt ggcagatttc 60

-continued

```
agatattgga caaacactct tagcttccac aaacttaatt ccaaaaaata atttttcact    120

tatgagcaat agagttatta cggacatatc agcaaaaatg tagtagtgtc aaggctcata    180

gatgatagaa atgaagagat gctgtattga tagaaaatgt gattcaggac tgtgtggatt    240

gatgattgtg agcttgctta tggatatcct aggtttgagg ttatagtagg acaatcaggt    300

tgaaatgtcc agcaggcagt aggtgaaaga caagtttagg gggcaaaacc atggatggag    360

atgaagattc atgacttcca cataaaagga tgggtgaaac tttgggaatt gatgaattct    420

ctagaggtga gctcaagacc cttaaaggct taaaacctca gcgttattgt ctactcttcc    480

ctcattttta tgcccacaaa tctggtcaat cctttatttg caatgcctct cacatctctt    540

tcttctgttt ccatttatac cgctgttgcc acagcccagg gtcccatcac ctcacacttg    600

atctattgta ttacattcct aactagtctt cccccgtttc taatctgttc tccgataaaa    660

gctgcacatc attttcagga taatcatcag tcgcctgcct aaaacttttc aatgtcttcc    720

cattgtcttt agaataaagt tcaaagtctt caaatgaccc caagcaagat aacttttgtt    780

tgccccttta gatccattt                                                 799
```

```
<210> SEQ ID NO 3
<211> LENGTH: 799
<212> TYPE: DNA
<213> ORGANISM: Artificial Sequence
<220> FEATURE:
<223> OTHER INFORMATION: Synthetic Polynucleotide

<400> SEQUENCE: 3

cagtctaata aggaaagcag aaaagcaaag caaccttata atatggtgca ataatttgct     60

ataatgaagt tatatacaaa gtgaagtaga agcatagaag aagcagcact aaatttgtct    120

gggtgagtca gagaaggcta accaggaaaa atagtttctg aactaacact tgaaggaggt    180

gtagcagttc atcactgaca gtgatgttgg ggtgggtctg gtttcaggag aggggaggaa    240

attggctttg gtctgaggct gaggtgtggg caaagcatta gcttatgtgg gtccattagc    300

ttatgtgagt ccacaaaagg tgtgtgtgtg tttgtgtgta tgtgtgtgtg tgtgtgtgtg    360

tgtgtgtgta cgaaatgggg gctcaatgat ttggtagtgg tttggtttgt caagaagcag    420

gctgggaact caataagcat ctttccattc atttctactg tgtatcccac agcttcacac    480

acacatgcac atttcaacat tggtgactgc ttcacttgca cacctaaggt aatgatggac    540

acacctgtag caatgtagat tcttcctaag ctaataatta gtttcaggag gtagcacata    600

catttaaaaa taggttaaaa taaagtgtta ttttaattgg taggtggatc tgttggcacc    660

aatgattatt cacggcatca agacccaggg tgcccgtcag aagttctcca gcctctacat    720

ctctcagttt atcatcatgt atagtcttga tgggaagaag tggcagactt atcgaggaaa    780

ttccactgga accttaatg                                                 799
```

```
<210> SEQ ID NO 4
<211> LENGTH: 800
<212> TYPE: DNA
<213> ORGANISM: Artificial Sequence
<220> FEATURE:
<223> OTHER INFORMATION: Synthetic Polynucleotide

<400> SEQUENCE: 4

gtatgtaatt agtcatttaa agggaatgcc tgaatacttt aaagaatttt ggcagatttc     60

agatattgga caaacactct tagcttccac aaacttaatt ccaaaaaata atttttcact    120

tatgagcaat agagttatta cggacatatc agcaaaaatg tagtagtgtc aaggctcata    180
```

```
gatgatagaa atgaagagat gctgtattga tagaaatatg tgattcagga ctgtgtggat    240

tgatgattgt gagcttgctt atggatatcc taggtttgag gttatagtag gacaatcagg    300

ttgaaatgtc cagcaggcag taggtgaaag acaagtttag gggcaaaac catggatgga     360

gatgaagatt catgacttcc acataaaagg atgggtgaaa ctttgggaat tgatgaattc    420

tctagaggtg agctcaagac ccttaaaggc ttaaaacctc agcgttattg tctactcttc    480

cctcattttt atgcccacaa atctggtcaa tcctttattt gcaatgcctc tcacatctct    540

ttcttctgtt tccatttata ccgctgttgc cacagcccag ggtcccatca cctcacactt    600

gatctattgt attacattcc taactagtct tcccccgttt ctaatctgtt ctccgataaa    660

agctgcacat cattttcagg ataatcatca gtcgcctgcc taaaactttt caatgtcttc    720

ccattgtctt tagaataaag ttcaaagtct tcaaatgacc ccaagcaaga taacttttgt    780

ttgcccttt agatccattt                                                  800
```

<210> SEQ ID NO 5
<211> LENGTH: 1920
<212> TYPE: DNA
<213> ORGANISM: Artificial Sequence
<220> FEATURE:
<223> OTHER INFORMATION: Synthetic Polynucleotide

<400> SEQUENCE: 5

```
cacctggctg ggcacatagg tgaagctgtt gagtctgtaa ttgtcaaact gctcccaggt     60

gccaattata atgtagaaga ggcacaagaa gatgaagtgg ataagcctgg cagtttgtca    120

agcattcatc agttgtcaag catttgtcag ttgcagaatg taggtaggct gccaaggctt    180

tattgtagcc tggttctatt gcagctttat tctagcaagg ctgctggaaa atacaataat    240

cactggtcca agaaagaact cttatactct atctatatga agaaacagta aaagtcaatt    300

cagtagaaat catgattttt gtgcctggtg ctttcacttt tttatgccac aataccaaga    360

ggttaaaatg aagtgtcttt gattgggaat accatctatc tgggaaaaga cagggctgca    420

acttctgaag accttgacac tctgtcctgt taccctgctt catttttctc ctgcgcttat    480

cactacttga tgctataaac aaataaaaac atatatgata taaggtctat ttctcctact    540

caactgtaag ttccatgagg gcagggcttt ctttcttgtt tactactcta ttccctgtat    600

ctaaaacagt gcttggcaca tagcaagtgc taaaaaaatat tctttgaatg agtgtatgaa   660

tggaacttac agtcagctga aggagacagt tattaagcat aagagtgatg accagtccaa    720

ttgtgtgtgt caggcatgtg tgaaaacgtg ctaaatttga cttgcttatt aggacagtaa    780

ctgatacttc taatgttctt gcagcccatg acctcttctt taagaagtgt ccattctgta    840

ctactttccc attattcact cattcattcc aaagcatttg ctatacagca gtattatacc    900

agataccata ttaggtgctg gggctagaga gaatataaaa gctaacattg attgagtgtt    960

tagtatgcgc caggccctga actcagcaca ttacatgtat taactcttta acccctatgg   1020

cagccctttg agataaaaac taatattatc ttcactttac agataagttg agacacagaa   1080

agttaggtga ctcaaatggg ttcactgcct taaggatctc agtctaataa ggaaagcaga   1140

aaagcaaagc aaccttataa tatggtgcaa taatttgcta taatgaagtt atatacaaag   1200

tgaagtagaa gcatagaaga agcagcacta aatttgtctg ggtgagtcag agaaggctaa   1260

ccaggaaaaa tagtttctga actaacactt gaaggaggtg tagcagttca tcactgacag   1320

tgatgttggg gtgggtctgg tttcaggaga ggggaggaaa ttggctttgg tctgaggctg   1380
```

aggtgtgggc aaagcattag cttatgtggg tccattagct tatgtgagtc cacaaaaggt 1440
gtgtgtgtgt ttgtgtgtat gtgtgtgtgt gtgtgtgtgt gtgtgtgtgt acgaaatggg 1500
ggctcaatga tttggtagtg gtttggtttg tcaagaagca ggctgggaac tcaataagca 1560
tctttccatt catttctact gtgtatccca cagcttcaca cacacatgca catttcaaca 1620
ttggtgactg cttcacttgc acacctaagg taatgatgga cacacctgta gcaatgtaga 1680
ttcttcctaa gctaataatt agtttcagga ggtagcacat acatttaaaa ataggttaaa 1740
ataaagtgtt attttaattg gtaggtggat ctgttggcac caatgattat tcacggcatc 1800
aagacccagg gtgcccgtca gaagttctcc agcctctaca tctctcagtt tatcatcatg 1860
tatagtcttg atgggaagaa gtggcagact tatcgaggaa attccactgg aaccttaatg 1920

<210> SEQ ID NO 6
<211> LENGTH: 800
<212> TYPE: DNA
<213> ORGANISM: Artificial Sequence
<220> FEATURE:
<223> OTHER INFORMATION: Synthetic Polynucleotide

<400> SEQUENCE: 6
gtatgtaatt agtcatttaa agggaatgcc tgaatacttt aaagaatttt ggcagatttc 60
agatattgga caaacactct tagcttccac aaacttaatt ccaaaaaata atttttcact 120
tatgagcaat agagttatta cggacatatc agcaaaaatg tagtagtgtc aaggctcata 180
gatgatagaa atgaagagat gctgtattga tagaaatatg tgattcagga ctgtgtggat 240
tgatgattgt gagcttgctt atggatatcc taggtttgag gttatagtag gacaatcagg 300
ttgaaatgtc cagcaggcag taggtgaaag acaagtttag ggggcaaaac catggatgga 360
gatgaagatt catgacttcc acataaaagg atgggtgaaa ctttgggaat tgatgaattc 420
tctagaggtg agctcaagac ccttaaaggc ttaaaacctc agcgttattg tctactcttc 480
cctcattttt atgcccacaa atctggtcaa tcctttattt gcaatgcctc tcacatctct 540
ttcttctgtt tccatttata ccgctgttgc cacagcccag ggtcccatca cctcacactt 600
gatctattgt attacattcc taactagtct tcccccgttt ctaatctgtt ctccgataaa 660
agctgcacat cattttcagg ataatcatca gtcgcctgcc taaaactttt caatgtcttc 720
ccattgtctt tagaataaag ttcaaagtct tcaaatgacc ccaagcaaga taacttttgt 780
ttgccccttt agatccattt 800

<210> SEQ ID NO 7
<211> LENGTH: 800
<212> TYPE: DNA
<213> ORGANISM: Artificial Sequence
<220> FEATURE:
<223> OTHER INFORMATION: Synthetic Polynucleotide

<400> SEQUENCE: 7
ttgatcctag gactccagga tcacgccctg ggccaaaggc agacgctaaa ccgctgagcc 60
acccaggcgt ccccaaacct ttgttataaa caccacgtta ggtgacccag attcactgcc 120
gtgagggtct cagtgtaaca gggacagcag atgagcaaag acagctctcc aatgtggtgc 180
agtaagatgc tctgatgcgc tcacatacga aatgaggcag agacagagaa agccgcactg 240
aacttgtctg ggtgagtcac gaaaggcgaa ccaggagaaa tagcttctga actgacactt 300
gaaagaggga cagcggttta tcattggcag tgatgttggg atgggcgctg ggctggggag 360
agcgcgggaa gtggcttggc cgaggccgag gctgaggttg ggcaaggcac gaggttccgt 420
ggccccttgt gtgcagcaca ttgctttgag tgtcccctgg tttgtgggga actaggcggg 480
gaacctaata agcacctttg ctttttgttc ccatcactca tctcagcgcc tcacacacac 540
ccaaggtact cctgagaata cccgtcttga tgcaggtcct tctcaagcca acaagtaacc 600
tcagaaggtg gtacatttac atgaagtgtt gctttcattg gcaggtggat ctcttggcac 660
cgatgattat tcacggcatc atgacccagg gggcccgcca gaagttctcc agcctctacg 720
tgtctcagtt tatcatcatg tacagtctgg atggcaacaa gtggcacagt taccgaggga 780
attccacggg gaccttaatg 800

<210> SEQ ID NO 8
<211> LENGTH: 800
<212> TYPE: DNA
<213> ORGANISM: Artificial Sequence
<220> FEATURE:
<223> OTHER INFORMATION: Synthetic Polynucleotide

<400> SEQUENCE: 8
gtatgtcatt agttcttctt tcaagagaat gcatgaatct tttaaagagc ttttgacaaa 60
gatttcaaat tcgggacaga cactcctagc ttctacgagc ttaattctaa gaaaagattt 120
ttccacttat gggcagtagg agtgattgtg aacatatgga ccaaaggtag gagcatcaaa 180
gatctcatag ataacagaca tgaagaggtg ctctgtaggc agagataggt gacgaggact 240
ccatggatgg atgacattcg tttgacgtga tggcagggca atcaagtcac atgtccagca 300
aaccgtcaat cacagacttg agtttagggg ggcaaatcat gaatgcaggt tgaagattcc 360
cgtcttccac ataaagcgtt ggctgagacc ttgggaaagg gtcacaagac cctaaattca 420
acaggcttgc aaccttagca tcattgtgta cccttccctc gtgttcgtgc ctcctgctga 480
attggtccac acaccccgca atcctctcct gtctcttctg tgtcaccgct acggctgtta 540
ctgtttattg cctgaggccc gtcaactcac attcatctac tccgttacat tcctaactag 600
ttgtctcctg tttctagtct cctctctgat aaaaactttt tggggagaat catcttatca 660
gccctgtgcc tacaaccttc cagtgtctgc ctctctcttc agaacaaagt taaaaaaatc 720
ctccagcggc tccaggcaaa ataactcatt ttccccttca gatgcattgc cctgcttctg 780
gttctgtgag tctgacttac 800

<210> SEQ ID NO 9
<211> LENGTH: 644
<212> TYPE: DNA
<213> ORGANISM: Artificial Sequence
<220> FEATURE:
<223> OTHER INFORMATION: Synthetic Polynucleotide

<400> SEQUENCE: 9
ttgatcctag gactccagga tcacgccctg ggccaaaggc agacgctaaa ccgctgagcc 60
acccaggcgt ccccaaacct ttgttataaa caccacgtta ggtgacccag attcactgcc 120
gtgagggtct cagtgtaaca gggacagcag atgagcaaag acagctctcc aatgtggtgc 180
agtaagatgc tctgatgcgc tcacatacga aatgaggcag agacagagaa agccgcactg 240
aacttgtctg ggtgagtcac gaaaggcgaa ccaggagaaa tagcttctga actgacactt 300
gaaagaggga cagcggttta tcattggcag tgatgttggg atgggcgctg ggctggggag 360
agcgcgggaa gtggcttggc cgaggccgag gctgaggttg ggcaaggcac gaggttccgt 420
ggccccttgt gtgcagcaca ttgctttgag tgtcccctgg tttgtgggga actaggcggg 480

-continued gaacctaata agcacctttg ctttttgttc ccatcactca tctcagcgcc tcacacacac 540
ccaaggtact cctgagaata cccgtcttga tgcaggtcct tctcaagcca acaagtaacc 600
tcagaaggtg gtacatttac atgaagtgtt gctttcattg gcag 644

<210> SEQ ID NO 10
<211> LENGTH: 800
<212> TYPE: DNA
<213> ORGANISM: Artificial Sequence
<220> FEATURE:
<223> OTHER INFORMATION: Synthetic Polynucleotide

<400> SEQUENCE: 10
gtatgtcatt agttcttctt tcaagagaat gcatgaatct tttaaagagc ttttgacaaa 60
gatttcaaat tcgggacaga cactcctagc ttctacgagc ttaattctaa gaaaagattt 120
ttccacttat gggcagtagg agtgattgtg aacatatgga ccaaaggtag gagcatcaaa 180
gatctcatag ataacagaca tgaagaggtg ctctgtaggc agagataggt gacgaggact 240
ccatggatgg atgacattcg tttgacgtga tggcagggca atcaagtcac atgtccagca 300
aaccgtcaat cacagacttg agtttagggg ggcaaatcat gaatgcaggt tgaagattcc 360
cgtcttccac ataaagcgtt ggctgagacc ttgggaaagg gtcacaagac cctaaattca 420
acaggcttgc aaccttagca tcattgtgta cccttccctc gtgttcgtgc ctcctgctga 480
attggtccac acaccccgca atcctctcct gtctcttctg tgtcaccgct acggctgtta 540
ctgtttattg cctgaggccc gtcaactcac attcatctac tccgttacat tcctaactag 600
ttgtctcctg tttctagtct cctctctgat aaaaactttt tggggagaat catcttatca 660
gccctgtgcc tacaaccttc cagtgtctgc ctctctcttc agaacaaagt taaaaaaatc 720
ctccagcggc tccaggcaaa ataactcatt ttccccttca gatgcattgc cctgcttctg 780
gttctgtgag tctgacttac 800

<210> SEQ ID NO 11
<211> LENGTH: 644
<212> TYPE: DNA
<213> ORGANISM: Artificial Sequence
<220> FEATURE:
<223> OTHER INFORMATION: Synthetic Polynucleotide

<400> SEQUENCE: 11
ttgatcctag gactccagga tcacgccctg ggccaaaggc agacgctaaa ccgctgagcc 60
acccaggcgt ccccaaacct ttgttataaa caccacgtta ggtgacccag attcactgcc 120
gtgagggtct cagtgtaaca gggacagcag atgagcaaag acagctctcc aatgtggtgc 180
agtaagatgc tctgatgcgc tcacatacga aatgaggcag agacagagaa agccgcactg 240
aacttgtctg ggtgagtcac gaaaggcgaa ccaggagaaa tagcttctga actgacactt 300
gaaagaggga cagcggttta tcattggcag tgatgttggg atgggcgctg ggctggggag 360
agcgcgggaa gtggcttggc cgaggccgag gctgaggttg ggcaaggcac gaggttccgt 420
ggccccttgt gtgcagcaca ttgctttgag tgtcccctgg tttgtgggga actaggcggg 480
gaacctaata agcacctttg ctttttgttc ccatcactca tctcagcgcc tcacacacac 540
ccaaggtact cctgagaata cccgtcttga tgcaggtcct tctcaagcca acaagtaacc 600
tcagaaggtg gtacatttac atgaagtgtt gctttcattg gcag 644

<210> SEQ ID NO 12
<211> LENGTH: 800

<212> TYPE: DNA
<213> ORGANISM: Artificial Sequence
<220> FEATURE:
<223> OTHER INFORMATION: Synthetic Polynucleotide

<400> SEQUENCE: 12
gtatgtcatt agttcttctt tcaagagaat gcatgaatct tttaaagagc ttttgacaaa 60
gatttcaaat tcgggacaga cactcctagc ttctacgagc ttaattctaa gaaaagattt 120
ttccacttat gggcagtagg agtgattgtg aacatatgga ccaaaggtag gagcatcaaa 180
gatctcatag ataacagaca tgaagaggtg ctctgtaggc agagataggt gacgaggact 240
ccatggatgg atgacattcg tttgacgtga tggcagggca atcaagtcac atgtccagca 300
aaccgtcaat cacagacttg agtttagggg ggcaaatcat gaatgcaggt tgaagattcc 360
cgtcttccac ataaagcgtt ggctgagacc ttgggaaagg gtcacaagac cctaaattca 420
acaggcttgc aaccttagca tcattgtgta cccttccctc gtgttcgtgc ctcctgctga 480
attggtccac acaccccgca atcctctcct gtctcttctg tgtcaccgct acggctgtta 540
ctgtttattg cctgaggccc gtcaactcac attcatctac tccgttacat tcctaactag 600
ttgtctcctg tttctagtct cctctctgat aaaaactttt tggggagaat catcttatca 660
gccctgtgcc tacaaccttc cagtgtctgc ctctctcttc agaacaaagt taaaaaaatc 720
ctccagcggc tccaggcaaa ataactcatt ttccccttca gatgcattgc cctgcttctg 780
gttctgtgag tctgacttac 800

<210> SEQ ID NO 13
<211> LENGTH: 644
<212> TYPE: DNA
<213> ORGANISM: Artificial Sequence
<220> FEATURE:
<223> OTHER INFORMATION: Synthetic Polynucleotide

<400> SEQUENCE: 13
ttgatcctag gactccagga tcacgccctg ggccaaaggc agacgctaaa ccgctgagcc 60
acccaggcgt ccccaaacct ttgttataaa caccacgtta ggtgacccag attcactgcc 120
gtgagggtct cagtgtaaca gggacagcag atgagcaaag acagctctcc aatgtggtgc 180
agtaagatgc tctgatgcgc tcacatacga aatgaggcag agacagagaa agccgcactg 240
aacttgtctg ggtgagtcac gaaaggcgaa ccaggagaaa tagcttctga actgacactt 300
gaaagaggga cagcggttta tcattggcag tgatgttggg atgggcgctg ggctggggag 360
agcgcgggaa gtggcttggc cgaggccgag gctgaggttg ggcaaggcac gaggttccgt 420
ggccccttgt gtgcagcaca ttgctttgag tgtcccctgg tttgtgggga actaggcggg 480
gaacctaata agcacctttg ctttttgttc ccatcactca tctcagcgcc tcacacacac 540
ccaaggtact cctgagaata cccgtcttga tgcaggtcct tctcaagcca acaagtaacc 600
tcagaaggtg gtacatttac atgaagtgtt gctttcattg gcag 644

<210> SEQ ID NO 14
<211> LENGTH: 800
<212> TYPE: DNA
<213> ORGANISM: Artificial Sequence
<220> FEATURE:
<223> OTHER INFORMATION: Synthetic Polynucleotide

<400> SEQUENCE: 14
gtatgtcatt agttcttctt tcaagagaat gcatgaatct tttaaagagc ttttgacaaa 60

-continued gatttcaaat tcgggacaga cactcctagc ttctacgagc ttaattctaa gaaaagattt 120
ttccacttat gggcagtagg agtgattgtg aacatatgga ccaaaggtag gagcatcaaa 180
gatctcatag ataacagaca tgaagaggtg ctctgtaggc agagataggt gacgaggact 240
ccatggatgg atgacattcg tttgacgtga tggcagggca atcaagtcac atgtccagca 300
aaccgtcaat cacagacttg agtttagggg ggcaaatcat gaatgcaggt tgaagattcc 360
cgtcttccac ataaagcgtt ggctgagacc ttgggaaagg gtcacaagac cctaaattca 420
acaggcttgc aaccttagca tcattgtgta cccttccctc gtgttcgtgc ctcctgctga 480
attggtccac acaccccgca atcctctcct gtctcttctg tgtcaccgct acggctgtta 540
ctgtttattg cctgaggccc gtcaactcac attcatctac tccgttacat tcctaactag 600
ttgtctcctg tttctagtct cctctctgat aaaaactttt tggggagaat catcttatca 660
gccctgtgcc tacaaccttc cagtgtctgc ctctctcttc agaacaaagt taaaaaaatc 720
ctccagcggc tccaggcaaa ataactcatt ttccccttca gatgcattgc cctgcttctg 780
gttctgtgag tctgacttac 800

<210> SEQ ID NO 15
<211> LENGTH: 624
<212> TYPE: DNA
<213> ORGANISM: Artificial Sequence
<220> FEATURE:
<223> OTHER INFORMATION: Synthetic Polynucleotide

<400> SEQUENCE: 15
gtcttctttg ggaacgtgga ctcaagtgga attaaacata acatctttaa cccacccata 60
atcgcgcgat atattcggtt gcacccgacc cattactcca tccgctcaac actcaggatg 120
gaactgatgg gttgtgatct taactcatgt tctatgcctc tgggtatgga gtcaaaggca 180
attagtgatg cgcagattac tgcttcttct tactttacca atatgttcgc aacgtggtca 240
ccatccaaag ctcggttgca tcttcaggga aggtcaaacg cgtggcggcc ccaggtcaac 300
aatcctaaag agtggttgca agttgacttt caaaagacta tgaaagtgac aggggtcacg 360
actcaaggcg tgaagtcatt gctcacttca atgtacgtta aagaattcct cattagcagt 420
tcacaggatg ggcatcagtg gactcttttc ttccaaaatg ggaaagtgaa ggtttttcaa 480
ggtaatcaag acagtttcac tccggtagtc aatagtttgg acccccctct tttgactaga 540
tacctgcgga ttcaccccca gagctgggtt caccaaattg ctctgagaat ggaggttctg 600
ggatgcgaag ctcaagacct gtac 624

<210> SEQ ID NO 16
<211> LENGTH: 624
<212> TYPE: DNA
<213> ORGANISM: Artificial Sequence
<220> FEATURE:
<223> OTHER INFORMATION: Synthetic Polynucleotide

<400> SEQUENCE: 16
gtcttctttg gtaacgtcga ttcttctggg atcaaacaca atatatttaa tcctcccata 60
atcgcacaat acattcggct ccacccaact cattactcca ttaggtctac cttgaggatg 120
gagttgctcg gatgcgactt caactcttgc agtatgccgc ttggaatgga atctaaagcg 180
ataagcgatg cgcaaattac tgcgtcctct tatcttagct ctatgctcgc tacctggtcc 240
ccatctcagg cacgattgca tctccaagga agaacgaacg cttggaggcc gcaagcgaat 300
aacccaaaag aatggcttca agtcgatttc aggaaaacaa tgaaggtcac cggcataacg 360
acgcagggtg ttaaaagttt gttgataagc atgtatgtga aggaatttct tatcagcagc 420
agtcaggatg gtcacaactg gaccctttc ctccaaaatg acaaagtcaa agttttccaa 480
ggcaacagag acagttctac tcccgtgagg aatgcgctgg aacccccact ggtggctcgc 540
tacgtcagat tgcatccaca aagctgggct caccatatag ctcttcgctt ggaggtgctt 600
ggatgcgata ctcagcagcc ggcc 624

<210> SEQ ID NO 17
<211> LENGTH: 627
<212> TYPE: DNA
<213> ORGANISM: Artificial Sequence
<220> FEATURE:
<223> OTHER INFORMATION: Synthetic Polynucleotide

<400> SEQUENCE: 17
gtcttctttg gtaacgtcga ttcttctggg atcaaacaca atatatttaa tcctcccata 60
atcgcacaat acattcggct ccacccaact cattactcca ttaggtctac cttgaggatg 120
gagttgctcg gatgcgactt caactcttgc agtatgccgc ttggaatgga atctaaagcg 180
ataagcgatg cgcaaattac tgcgtcctct tatcttagct ctatgctcgc tacctggtcc 240
ccatctcagg cacgattgca tctccaagga agaacgaacg cttggaggcc gcaagcgaat 300
aacccaaaag aatggcttca agtcgatttc aggaaaacaa tgaaggtcac cggcataacg 360
acgcagggtg ttaaaagttt gttgataagc atgtatgtga aggaatttct tatcagcagc 420
agtcaggatg gtcacaactg gaccctttc ctccaaaatg acaaagtcaa agttttccaa 480
ggcaacagag acagttctac tcccgtgagg aatgcgctgg aacccccact ggtggctcgc 540
tacgtcagat tgcatccaca aagctgggct caccatatag ctcttcgctt ggaggtgctt 600
ggatgcgata ctcagcagcc ggcctga 627

<210> SEQ ID NO 18
<211> LENGTH: 3672
<212> TYPE: DNA
<213> ORGANISM: Artificial Sequence
<220> FEATURE:
<223> OTHER INFORMATION: Synthetic Polynucleotide

<400> SEQUENCE: 18
gccctgaact cagcacatta catgtattaa ctctttaacc cctatggcag ccctttgaga 60
taaaaactaa tattatcttc actttacaga taagttgaga cacagaaagt taggtgactc 120
aaatgggttc actgccttaa ggatctcagt ctaataagga aagcagaaaa gcaaagcaac 180
cttataatat ggtgcaataa tttgctataa tgaagttata tacaaagtga agtagaagca 240
tagaagaagc agcactaaat ttgtctgggt gagtcagaga aggctaacca ggaaaaatag 300
tttctgaact aacacttgaa ggaggtgtag cagttcatca ctgacagtga tgttggggtg 360
ggtctggttt caggagaggg gaggaaattg gctttggtct gaggctgagg tgtgggcaaa 420
gcattagctt atgtgggtcc attagcttat gtgagtccac aaaaggtgtg tgtgtgtttg 480
tgtgtatgtg tgtgtgtgtg tgtgtgtgtg tgtgtacgaa atgggggctc aatgatttgg 540
tagtggtttg gtttgtcaag aagcaggctg ggaactcaat aagcatcttt ccattcattt 600
ctactgtgta tcccacagct tcacacacac atgcacattt caacattggt gactgcttca 660
cttgcacacc taaggtaatg atggacacac ctgtagcaat gtagattctt cctaagctaa 720
taattagttt caggaggtag cacatacatt taaaaatagg ttaaaataaa gtgttatttt 780

-continued

```
aattggtagg tggatctgtt ggcaccaatg attattcacg gcatcaagac ccagggtgcc    840
cgtcagaagt tctccagcct ctacatctct cagtttatca tcatgtatag tcttgatggg    900
aagaagtggc agacttatcg aggaaattcc actggaacct taatggtctt ctttgggaac    960
gtggactcaa gtggaattaa acataacatc tttaacccac ccataatcgc gcgatatatt   1020
cggttgcacc cgacccatta ctccatccgc tcaacactca ggatggaact gatgggttgt   1080
gatcttaact catgttctat gcctctgggt atggagtcaa aggcaattag tgatgcgcag   1140
attactgctt cttcttactt taccaatatg ttcgcaacgt ggtcaccatc caaagctcgg   1200
ttgcatcttc agggaaggtc aaacgcgtgg cggccccagg tcaacaatcc taaagagtgg   1260
ttgcaagttg actttcaaaa gactatgaaa gtgacagggg tcacgactca aggcgtgaag   1320
tcattgctca cttcaatgta cgttaaagaa ttcctcatta gcagttcaca ggatgggcat   1380
cagtggactc ttttcttcca aaatgggaaa gtgaaggttt ttcaaggtaa tcaagacagt   1440
ttcactccgg tagtcaatag tttggacccc cctcttttga ctagatacct gcggattcac   1500
ccccagagct gggttcacca aattgctctg agaatggagg ttctgggatg cgaagctcaa   1560
gacctgtacg cggccgccga ctacaaagac catgacggtg attataaaga tcatgacatc   1620
gattacaagg atgacgatga caaggcggcc gccggcagcg gagagggcag aggaagtctt   1680
ctaacatgcg gtgacgtgga ggagaatccc ggccctaggg gtaccatggt gagcaagggc   1740
gaggaggata acatggccat catcaaggag ttcatgcgct tcaaggtgca catggagggc   1800
tccgtgaacg gccacgagtt cgagatcgag ggcgagggcg agggccgccc ctacgagggc   1860
acccagaccg ccaagctgaa ggtgaccaag ggtggccccc tgcccttcgc ctgggacatc   1920
ctgtcccctc agttcatgta cggctccaag gcctacgtga agcaccccgc cgacatcccc   1980
gactacttga agctgtcctt ccccgagggc ttcaagtggg agcgcgtgat gaacttcgag   2040
gacggcggcg tggtgaccgt gacccaggac tcctccctgc aggacggcga gttcatctac   2100
aaggtgaagc tgcgcggcac caacttcccc tccgacggcc ccgtaatgca gaagaagacc   2160
atgggctggg aggcctcctc cgagcggatg taccccgagg acggcgccct gaagggcgag   2220
atcaagcaga ggctgaagct gaaggacggc ggccactacg acgctgaggt caagaccacc   2280
tacaaggcca agaagcccgt gcagctgccc ggcgcctaca acgtcaacat caagttggac   2340
atcacctccc acaacgagga ctacaccatc gtggaacagt acgaacgcgc cgagggccgc   2400
cactccaccg gcggcatgga cgagctgtac aagtaactcg agcctctaga actatagtga   2460
gtcgtattac gtagatccag acatgataag atacattgat gagtttggac aaaccacaac   2520
tagaatgcag tgaaaaaaat gctttatttg tgaaatttgt gatgctattg ctttatttgt   2580
aaccattata agctgcaata aacaagttaa caacaacaat tgcattcatt ttatgtttca   2640
ggttcagggg gaggtgtggg aggtttttta aaaagcttta cgtatgtaat tagtcattta   2700
aagggaatgc ctgaatactt taaagaattt tggcagattt cagatattgg acaaacactc   2760
ttagcttcca caaacttaat tccaaaaaat aatttttcac ttatgagcaa tagagttatt   2820
acggacatat cagcaaaaat gtagtagtgt caaggctcat agatgataga aatgaagaga   2880
tgctgtattg atagaaatat gtgattcagg actgtgtgga ttgatgattg tgagcttgct   2940
tatggatatc ctaggtttga ggttatagta ggacaatcag gttgaaatgt ccagcaggca   3000
gtaggtgaaa gacaagttta gggggcaaaa ccatggatgg agatgaagat tcatgacttc   3060
cacataaaag gatgggtgaa actttgggaa ttgatgaatt ctctagaggt gagctcaaga   3120
cccttaaagg cttaaaacct cagcgttatt gtctactctt ccctcatttt tatgcccaca   3180
```

aatctggtca atcctttatt tgcaatgcct ctcacatctc tttcttctgt ttccatttat 3240
accgctgttg ccacagccca gggtcccatc acctcacact tgatctattg tattacattc 3300
ctaactagtc ttcccccgtt tctaatctgt tctccgataa aagctgcaca tcattttcag 3360
gataatcatc agtcgcctgc ctaaaacttt tcaatgtctt cccattgtct ttagaataaa 3420
gttcaaagtc ttcaaatgac cccaagcaag ataacttttg tttgcccctt tagatccatt 3480
ttcctgcttc tctaccctgc ttcttgttct gtgaggtgag cttgtataga atacatcaac 3540
aggttacctt gtcctccagc ttttggttgg atttcaccaa cagggagcac tggcaaaaga 3600
ttggcatatt tattcttctg actttctcct tgcagaggag ttcactgtat ctccccactt 3660
aaggtcactg tt 3672

<210> SEQ ID NO 19
<211> LENGTH: 146
<212> TYPE: DNA
<213> ORGANISM: Artificial Sequence
<220> FEATURE:
<223> OTHER INFORMATION: Synthetic Polynucleotide

<400> SEQUENCE: 19
gccctgaact cagcacatta catgtattaa ctctttaacc cctatggcag ccctttgaga 60
taaaaactaa tattatcttc actttacaga taagttgaga cacagaaagt taggtgactc 120
aaatgggttc actgccttaa ggatct 146

<210> SEQ ID NO 20
<211> LENGTH: 799
<212> TYPE: DNA
<213> ORGANISM: Artificial Sequence
<220> FEATURE:
<223> OTHER INFORMATION: Synthetic Polynucleotide

<400> SEQUENCE: 20
cagtctaata aggaaagcag aaaagcaaag caaccttata atatggtgca ataatttgct 60
ataatgaagt tatatacaaa gtgaagtaga agcatagaag aagcagcact aaatttgtct 120
gggtgagtca gagaaggcta accaggaaaa atagtttctg aactaacact tgaaggaggt 180
gtagcagttc atcactgaca gtgatgttgg ggtgggtctg gtttcaggag aggggaggaa 240
attggctttg gtctgaggct gaggtgtggg caaagcatta gcttatgtgg gtccattagc 300
ttatgtgagt ccacaaaagg tgtgtgtgtg tttgtgtgta tgtgtgtgtg tgtgtgtgtg 360
tgtgtgtgta cgaaatgggg gctcaatgat ttggtagtgg tttggtttgt caagaagcag 420
gctgggaact caataagcat ctttccattc atttctactg tgtatcccac agcttcacac 480
acacatgcac atttcaacat tggtgactgc ttcacttgca cacctaaggt aatgatggac 540
acacctgtag caatgtagat tcttcctaag ctaataatta gtttcaggag gtagcacata 600
catttaaaaa taggttaaaa taaagtgtta ttttaattgg taggtggatc tgttggcacc 660
aatgattatt cacggcatca agacccaggg tgcccgtcag aagttctcca gcctctacat 720
ctctcagttt atcatcatgt atagtcttga tgggaagaag tggcagactt atcgaggaaa 780
ttccactgga accttaatg 799

<210> SEQ ID NO 21
<211> LENGTH: 623
<212> TYPE: DNA
<213> ORGANISM: Artificial Sequence
<220> FEATURE:

-continued

<223> OTHER INFORMATION: Synthetic Polynucleotide

<400> SEQUENCE: 21
gtcttctttg ggaacgtgga ctcaagtgga attaaacata acatctttaa cccacccata 60
atcgcgcgat atattcggtt gcacccgacc cattactcca tccgctcaac actcaggatg 120
gaactgatgg gttgtgatct taactcatgt tctatgcctc tgggtatgga gtcaaaggca 180
attagtgatg cgcagattac tgcttcttct tactttacca atatgttcgc aacgtggtca 240
ccatccaaag ctcggttgca tcttcaggga aggtcaaacg cgtggcggcc ccaggtcaac 300
aatcctaaag agtggttgca agttgacttt caaaagacta tgaaagtgac aggggtcacg 360
actcaaggcg tgaagtcatt gctcacttca atgtacgtta aagaattcct cattagcagt 420
tcacaggatg ggcatcagtg gactcttttc ttccaaaatg ggaaagtgaa ggtttttcaa 480
ggtaatcaag acagtttcac tccggtagtc aatagtttgg accccccctct tttgactaga 540 tacctgcgga ttcaccccca gagctgggtt caccaaattg ctctgagaat ggaggttctg 600
ggatgcgaag ctcaagacct gta 623

<210> SEQ ID NO 22
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 22
aaccttaatg gtcttctttg 20

<210> SEQ ID NO 23
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 23
gactacaaag accatgacgg tgattataaa gatcatgaca tcgattacaa ggatgacgat 60
gacaag 66

<210> SEQ ID NO 24
<211> LENGTH: 1028
<212> TYPE: DNA
<213> ORGANISM: Artificial Sequence
<220> FEATURE:
<223> OTHER INFORMATION: Synthetic Polynucleotide

<400> SEQUENCE: 24
ggcagcggag agggcagagg aagtcttcta acatgcggtg acgtggagga gaatcccggc 60
cctaggggta ccatggtgag caagggcgag gaggataaca tggccatcat caaggagttc 120
atgcgcttca aggtgcacat ggagggctcc gtgaacggcc acgagttcga gatcgagggc 180
gagggcgagg gccgccccta cgagggcacc cagaccgcca agctgaaggt gaccaagggt 240
ggccccctgc ccttcgcctg ggacatcctg tcccctcagt tcatgtacgg ctccaaggcc 300
tacgtgaagc accccgccga catccccgac tacttgaagc tgtccttccc cgagggcttc 360
aagtgggagc gcgtgatgaa cttcgaggac ggcggcgtgg tgaccgtgac ccaggactcc 420
tccctgcagg acggcgagtt catctacaag gtgaagctgc gcggcaccaa cttcccctcc 480
gacggccccg taatgcagaa gaagaccatg ggctgggagg cctcctccga gcggatgtac 540
cccgaggacg gcgccctgaa gggcgagatc aagcagaggc tgaagctgaa ggacggcggc 600
cactacgacg ctgaggtcaa gaccacctac aaggccaaga agcccgtgca gctgcccggc 660
gcctacaacg tcaacatcaa gttggacatc acctcccaca acgaggacta caccatcgtg 720
gaacagtacg aacgcgccga gggccgccac tccaccggcg gcatggacga gctgtacaag 780
taactcgagc ctctagaact atagtgagtc gtattacgta gatccagaca tgataagata 840
cattgatgag tttggacaaa ccacaactag aatgcagtga aaaaaatgct ttatttgtga 900
aatttgtgat gctattgctt tatttgtaac cattataagc tgcaataaac aagttaacaa 960
caacaattgc attcatttta tgtttcaggt tcagggggag gtgtgggagg ttttttaaaa 1020
agctttac 1028

<210> SEQ ID NO 25
<211> LENGTH: 801
<212> TYPE: DNA
<213> ORGANISM: Artificial Sequence
<220> FEATURE:
<223> OTHER INFORMATION: Synthetic Polynucleotide

<400> SEQUENCE: 25
gtatgtaatt agtcatttaa agggaatgcc tgaatacttt aaagaatttt ggcagatttc 60
agatattgga caaacactct tagcttccac aaacttaatt ccaaaaaata atttttcact 120
tatgagcaat agagttatta cggacatatc agcaaaaatg tagtagtgtc aaggctcata 180
gatgatagaa atgaagagat gctgtattga tagaaatatg tgattcagga ctgtgtggat 240
tgatgattgt gagcttgctt atggatatcc taggtttgag gttatagtag gacaatcagg 300
ttgaaatgtc cagcaggcag taggtgaaag acaagtttag ggggcaaaac catggatgga 360
gatgaagatt catgacttcc acataaaagg atgggtgaaa ctttgggaat tgatgaattc 420
tctagaggtg agctcaagac ccttaaaggc ttaaaacctc agcgttattg tctactcttc 480
cctcattttt atgcccacaa atctggtcaa tcctttattt gcaatgcctc tcacatctct 540
ttcttctgtt tccatttata ccgctgttgc cacagcccag ggtcccatca cctcacactt 600
gatctattgt attacattcc taactagtct tcccccgttt ctaatctgtt ctccgataaa 660
agctgcacat cattttcagg ataatcatca gtcgcctgcc taaaactttt caatgtcttc 720
ccattgtctt tagaataaag ttcaaagtct tcaaatgacc ccaagcaaga taacttttgt 780
ttgccccttt agatccattt t 801

<210> SEQ ID NO 26
<211> LENGTH: 190
<212> TYPE: DNA
<213> ORGANISM: Artificial Sequence
<220> FEATURE:
<223> OTHER INFORMATION: Synthetic Polynucleotide

<400> SEQUENCE: 26
cctgcttctc taccctgctt cttgttctgt gaggtgagct tgtatagaat acatcaacag 60
gttaccttgt cctccagctt ttggttggat ttcaccaaca gggagcactg gcaaaagatt 120
ggcatattta ttcttctgac tttctccttg cagaggagtt cactgtatct ccccacttaa 180
ggtcactgtt 190